(12) United States Patent
Thrasher et al.

(10) Patent No.: US 10,583,180 B2
(45) Date of Patent: Mar. 10, 2020

(54) METHOD FOR TREATING ADENOSINE DEAMINASE SEVERE COMBINED IMUNODEFICIENCY

(71) Applicants: UCL Business PLC, London (GB); The Regents of the University of California, Oakland, CA (US)

(72) Inventors: Adrian Thrasher, London (GB); Donald Kohn, East Los Angeles, CA (US); Bobby Gaspar, London (GB)

(73) Assignees: UCL Business LTD, London (GB); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/383,030

(22) Filed: Dec. 19, 2016

(65) Prior Publication Data

US 2017/0173124 A1    Jun. 22, 2017

Related U.S. Application Data

(63) Continuation-in-part of application No. PCT/GB2016/053970, filed on Dec. 16, 2016.

(60) Provisional application No. 62/269,655, filed on Dec. 18, 2015.

(51) Int. Cl.
| | | |
|---|---|---|
| A61K 48/00 | (2006.01) | |
| A61K 38/50 | (2006.01) | |
| C07K 14/47 | (2006.01) | |
| A61K 35/28 | (2015.01) | |
| C12N 7/00 | (2006.01) | |
| C12N 9/78 | (2006.01) | |
| C12N 15/86 | (2006.01) | |

(52) U.S. Cl.
CPC .............. *A61K 38/50* (2013.01); *A61K 35/28* (2013.01); *A61K 48/0008* (2013.01); *A61K 48/0066* (2013.01); *C07K 14/4705* (2013.01); *C12N 7/00* (2013.01); *C12N 9/78* (2013.01); *C12N 15/86* (2013.01); *C12Y 305/04004* (2013.01); *C12N 2740/16032* (2013.01); *C12N 2740/16043* (2013.01); *C12N 2740/16062* (2013.01); *C12N 2740/16071* (2013.01)

(58) Field of Classification Search
CPC ........................... A61K 35/38; A61K 48/0066
See application file for complete search history.

(56) References Cited

U.S. PATENT DOCUMENTS

2014/0093485 A1    4/2014    Medin et al.

OTHER PUBLICATIONS

Aiut et al. EMBO Mol Med 9(6):737-740, 2017 (Year: 2017).*
Adagen Gene therapy. www.adagen.com/gene_therapy.html. Printed Nov. 8, 2018 pp. 1-3. (Year: 2018).*
Braid et al. Cytotherapy 20:232-244, 2018 (Year: 2018).*
Adams et al., "Adenosine deaminase activity in thymus and other human tissues" Clin Exp Immunol. 26(3):647-649 (1976).
Aiuti et al., "Gene therapy for immunodeficiency due to adenosine deaminase deficiency" N Engl J Med. 360(5):447-458 (2009).
Aiuti et al., "Multilineage hematopoietic reconstitution without clonal selection in ADA-SCID patients treated with stem cell gene therapy" J Clin Invest. 117(8):2233-2240 (2007).
Antoine et al., "Long-term survival and transplantation of haemopoietic stem cells for immunodeficiencies: report of the European experience 1968-99," Lancet. 361(9357):553-560 (2003).
Apasov et al., "Adenosine deaminase deficiency increases thymic apoptosis and causes defective T cell receptor signalling" J Clin Invest. 108(1):131-141 (2001).
Ariga et al., "T-cell lines from 2 patients with adenosine deaminase (ADA) deficiency showed the restoration of ADA activity resulted from the reversion of an inherited mutation" Blood. 97(9):2896-2899 (2001).
Arredondo-Vega et al., "Adenosine deaminase deficiency: genotype-phenotype correlations based on expressed activity of 29 mutant alleles," Am J Hum Genet. 63(4):1049-1059 (1998).
Bartelink et al.,"Body weight-dependent pharmacokinetics of busulfan in paediatric haematopoietic stem cell transplantation patients: towards individualized dosing" Clin Pharmacokinet. 51(5):331-45 (2012).
Benveniste et al., "Interference with thymocyte differentiation by an inhibitor of S-adenosylhomocysteine hydrolase," J Immunol. 155(2):536-544 (1995).
Benveniste et al., "p53 expression is required for thymocyte apoptosis induced by adenosine deaminase deficiency" Proc Natl Acad Sci U. S. A. 92(18):8373-8377 (1995).
Blackburn et al., "Adenosine deaminase-deficient mice generated using a two-stage genetic engineering strategy exhibit a combined immunodeficiency" J Biol Chem. 273(9):5093-5100 (1998).
Blaese et al., "T lymphocyte-directed gene therapy for ADA-SCID: initial trial results after 4 years" Science. 270(5235):475-480 (1995).
Bollinger et al.,"Brief report: hepatic dysfunction as a complication of adenosine deaminase deficiency" N Engl J Med. 334(21):1367-1371 (1996).
Booth et al., "Management options for adenosine deaminase deficiency; proceedings of the EBMT satellite workshop (Hamburg, Mar. 2006)" Clin Immunol. 123(2):139-147 (2007).
Bordignon et al., "Gene therapy in peripheral blood lymphocytes and bone marrow for ADA-immunodeficient patients" Science. 270(5235): 470-475 (1995).
Borkowsky et al., "Adenosine deaminase deficiency without immunodeficiency: clinical and metabolic studies" Pediatr Res. 14(7): 885-889 (1980).
Boztug et al., "Stem-cell gene therapy for the Wiskott-Aldrich syndrome" N Engl J Med. 363(20):1918-1927 (2010).
Candotti et al., "Gene therapy for adenosine deaminase-deficient severe combined immune deficiency: clinical comparison of retroviral vectors and treatment plans" Blood. 120(18):3635-3646 (2012).

(Continued)

*Primary Examiner* — Marcia S Noble
(74) *Attorney, Agent, or Firm* — Clark & Elbing LLP

(57) ABSTRACT

The present invention relates to the prevention and/or treatment of ADA-SCID, in a patient.

23 Claims, 24 Drawing Sheets

Specification includes a Sequence Listing.

(56) References Cited

OTHER PUBLICATIONS

Carbonaro et al., "Preclinical Demonstration of Lentiviral Vector-mediated Correction of Immunological and Metabolic Abnormalities in Models of Adenosine Deaminase Deficiency," Mol Ther. 22(3):607-622 (2014).
Carson et al., "Lymphospecific toxicity in adenosine deaminase deficiency and purine nucleoside phosphorylase deficiency: possible role of nucleoside kinase(s)," Proc. Natl. Acad. Sci. U S A. 74(12):5677-5681 (1977).
Chaffee et al., "IgG antibody response to polyethylene glycol-modified adenosine deaminase in patients with adenosine deaminase deficiency" J Clin Invest. 89(5): 1643-1651 (1992).
Chan et al., "Long-term efficacy of enzyme replacement therapy for adenosine deaminase (ADA)-deficient Severe Combined Immunodeficiency (SCID)," Clin Immunol. 117(2): 133-143 (2005).
Daddona et al., "Adenosine deaminase deficiency with normal immune function: An acidic enzyme mutation," J Clin Invest. 72(2):483-492 (1983).
Dinjens et al., "Distribution of adenosine deaminase complexing protein (ADCP) in human tissues," J Histochem Cytochem. 37(12):1869-1875 (1989).
Dong et al., "Determination of adenosine deaminase binding domain on CD26 and its immunoregulatory effect on T cell activation," J Immunol. 159(12): 6070-6076 (1997).
Dooley et al., "First trimester diagnosis of adenosine deaminase deficiency," Prenat Diagn. 7(8):561-565 (1987).
Dull et al., "A third-generation lentivirus vector with a conditional packaging system" J Virol. 72(11):8463-8471 (1998).
Fischer et al., "Naturally occurring primary deficiencies of the immune system" Annu Rev Immunol. 15:93-124 (1997).
Fox et al., "Ta1, a novel 105 KD human T cell activation antigen defined by a monoclonal antibody," J Immunol. 133(3):1250-1256 (1984).
Gaspar et al., "Hematopoietic stem cell gene therapy for adenosine deaminase-deficient severe combined immunodeficiency leads to long-term immunological recovery and metabolic correction," Sci Transl Med. 3(97):97ra80 (2011) (9 pages).
Gaspar et al., "How I treat ADA deficiency" Blood. 114(17):3524-3532 (2009).
Gaspar et al., "Successful reconstitution of immunity in ADA-SCID by stem cell gene therapy following cessation of PEG-ADA and use of mild preconditioning," Mol Ther. 14(4):505-513 (2006).
Giblett et al., "Adenosine-deaminase deficiency in two patients with severely impaired cellular immunity," Lancet. 2(7786):1067-1069 (1972).
Hacein-Bey-Abina et al., "Insertional oncogenesis in 4 patients after retrovirus-mediated gene therapy of SCID-X1," J Clin Invest. 118(9):3132-3142 (2008).
Hacein-Bey-Abina et al., "LMO2-associated clonal T cell proliferation in two patients after gene therapy for SCID-X1" Science. 302(5644):415-419 (2003).
Hershfield, M.H., "Adenosine deaminase deficiency," GeneReviews[Internet], NCBI Bookshelf, posted Oct. 3, 2006 (36 pages).
Hershfield et al., "In vivo inactivation of erythrocyte S-adenosylhomocysteine hydrolase by 2'-deoxyadenosine in adenosine deaminase-deficient patients" J Clin Invest. 63(4):807-811 (1979).
Hirschhorn et al., "Amelioration of neurologic abnormalities after "enzyme replacement" in adenosine deaminase deficiency" N Engl J Med. 303(7):377-380 (1980).
Hirschhorn et al., "Spontaneous in vivo reversion to normal of an inherited mutation in a patient with adenosine deaminase deficiency" Nat. Genet. 13:290-295 (1996).
Hirschhorn, R., "Overview of biochemical abnormalities and molecular genetics of adenosine deaminase deficiency" Pediatr. Res. 33, S35-41 (1993).

Howe et al., "Insertional mutagenesis combined with acquired somatic mutations causes leukemogenesis following gene therapy of SCID-X1 patients" J Clin Invest. 118(9):3143-3150 (2008).
Husain et al., "Burkitt's lymphoma in a patient with adenosine deaminase deficiency—severe combined immunodeficiency treated with polyethylene glycol-adenosine deaminase" J Pediatr. 151(1): 93-95 (2007).
Ingolia et al., "Molecular cloning of the murine adenosine deaminase gene from a genetically enriched source: identification and characterization of the promoter region," Mol Cell Biol. 6(12): 4458-4466 (1986).
International Search Report and Written Opinion for International Patent Application No. PCT/GB2016/053970, dated Feb. 24, 2017 (14 pages).
Kadonaga et al., "Isolation of cDNA encoding transcription factor Sp1 and functional analysis of the DNA binding domain," Cell. 51(6):1079-1090 (1987).
Kaufman et al., "Cerebral lymphoma in an adenosine deaminase-deficient patient with severe combined immunodeficiency receiving polyethylene glycol-conjugated adenosine deaminase" Pediatrics 116(6):e876-e879 (2005).
Kohn et al., "T lymphocytes with a normal ADA gene accumulate after transplantation of transduced autologous umbilical cord blood CD34+ cells in ADA-deficient SCID neonates," available in PMC Sep. 19, 2013, published in final edited form as: Nat Med. 4(7):775-780 (1998) (13 pages).
Lee et al., "Mechanisms of deoxyadenosine toxicity in human lymphoid cells in vitro: relevance to the therapeutic use of inhibitors of adenosine deaminase," Br J Haematol. 56(1):107-119 (1984).
Macchi et al., "Mutations of Jak-3 gene in patients with autosomal severe combined immune deficiency (SCID)" Nature. 377(6544): 65-68 (1995).
Markert et al., "Adenosine deaminase (ADA) deficiency due to deletion of the ADA gene promoter and first exon by homologous recombination between two Alu elements," J Clin Invest. 81(5):1323-1327 (1988).
Marwaha et al., "Extreme thrombocytosis in response to PEG-ADA: early therapeutic and risk indicator," Clin Pediatr (Phila). 39(3):183-186 (2000).
Migchielsen et al., "Adenosine-deaminase-deficient mice die perinatally and exhibit liver-cell degeneration, atelectasis and small intestinal cell death," Nat. Genet. 10: 279-287 (1995).
Montiel-Equihua et al., "The beta-Globin Locus Control Region in Combination With the EF1(alpha) Short Promoter Allows Enhanced Lentiviral Vector-mediated Erythroid Gene Expression With Conserved Multilineage Activity," Mol Ther. 20(7):1400-1409 (2012).
Morgan et al., "Heterogeneity of biochemical, clinical and immunological parameters in severe combined immunodeficiency due to adenosine deaminase deficiency" Clin Exp Immunol. 70(3):491-499 (1987).
Morrison et al., "A marker for neoplastic progression of human melanocytes is a cell surface ectopeptidase," J Exp Med. 177(4):1135-1143 (1993).
Moshous et al., "Artemis, a novel DNA double-strand break repair/ V(D)J recombination protein, is mutated in human severe combined immune deficiency," Cell. 105(2):177-186 (2001).
Noguchi et al., "Interleukin-2 receptor gamma chain mutation results in X-linked severe combined immunodeficiency in humans," Cell. 73(1):147-57 (1993).
Ott et al., "Correction of X-linked chronic granulomatous disease by gene therapy, augmented by insertional activation of MDS1-EVI1, PRDM16 or SETBP1," Nat Med. 12(4):401-409 (2006).
Ozsahin et al., "Adenosine deaminase deficiency in adults," Blood. 89(8):2849-2855 (1997).
Petersen et al., "New assignment of the adenosine deaminase gene locus to chromosome 20q13 X 11 by study of a patient with interstitial deletion 20q," J Med Genet. 24(2):93-96 (1987).
Philip et al., "Regional assignment of the ADA locus on 20q13.2 leads to qter by gene dosage studies," Cytogenet Cell Genet. 27(2-3):187-189 (1980).
Puel et al., "Defective IL7R expression in T(-)B(+)Nk(+) severe combined immunodeficiency," Nat Genet. 20(4):394-397 (1998).

(56) References Cited

OTHER PUBLICATIONS

Ratech et al., "Pathologic findings in adenosine deaminase-deficient severe combined immunodeficiency. I. Kidney, adrenal, and chondro—osseous tissue alterations," Am J Pathol. 120(1):157-169 (1985).
Revy et al. "Cernunnos-XLF, a recently identified non-homologous end-joining factor required for the development of the immune system," Curr. Opin. Allergy Clin. Immunol. 6(6):416-420 (2006).
Richard et al., "The binding site of human adenosine deaminase for CD26/Dipeptidyl peptidase IV: the Arg142Gln mutation impairs binding to CD26 but does not cause immune deficiency," J Exp Med. 192(9):1223-35 (2000).
Rieux-Laucat et al., "Inherited and somatic CD3zeta mutations in a patient with T-cell deficiency," N Engl J Med. 354(18):1913-1921 (2006).
Sanchez et al., "Carrier frequency of a nonsense mutation in the adenosine deaminase (ADA) gene implies a high incidence of ADA-deficient severe combined immunodeficiency (SCID) in Somalia and a single, common haplotype indicates common ancestry," Ann Hum Genet. 71(Pt 3):336-347 (2007).
Schambach et al., "Woodchuck hepatitis virus post-transcriptional regulatory element deleted from X protein and promoter sequences enhances retroviral vector titer and expression," Gene Ther. 13(7):641-645 (2006).
Schambach et al., "Context dependence of different modules for posttranscriptional enhancement of gene expression from retroviral vectors," Mol Ther. 2(5): 435-445 (2000).
Schrader et al., "Characterization of the adenosine deaminase-adenosine deaminase complexing protein binding reaction," J. Biol. Chem. 265(31): 19312-19318 (1990).
SenGupta et al.,"A flow cytometric method for the detection of adenosine deaminase in mononuclear cells," J Immunol Methods. 80(2): 155-162 (1985).
Shovlin et al., "Adult onset immunodeficiency caused by inherited adenosine deaminase deficiency," J Immunol. 153(5):2331-2339 (1994).
Shultz et al., "Human lymphoid and myeloid cell development in NOD/LtSz-scid IL2R gamma null mice engrafted with mobilized human hemopoietic stem cells," J Immunol. 174(10):6477-6489 (2005).
Soudais et al., "Independent mutations of the human CD3-epsilon gene resulting in a T cell receptor/CD3 complex immunodeficiency" Nat. Genet. 3:77-81 (1993).
Stein et al., "Genomic instability and myelodysplasia with monosomy 7 consequent to EVI1 activation after gene therapy for chronic granulomatous disease," Nat Med. 16(2):198-204 (2010).
Stephan et al., "Atypical X-linked severe combined immunodeficiency due to possible spontaneous reversion of the genetic defect in T cells," N Engl J Med. 335(21):1563-1567 (1996).
Tanaka et al., "Sensorineural deafness in siblings with adenosine deaminase deficiency," Brain Dev. 18(4):304-306 (1996).
Thrasher et al., "Failure of SCID-X1 gene therapy in older patients," Blood. 105(11):4255-4257 (2005).
Tischfield et al., "Assignment of a gene for adenosine deaminase to human chromosome 20," Hum Hered. 24(1):1-11 (1974).
Titman et al., "Cognitive and behavioural abnormalities in children after hematopoietic stem cell transplantation for severe congenital immunodeficiencies," Blood. 112(9):3907-3913 (2008).
Trotta, "Identification of a membrane adenosine deaminase binding protein from human placenta," Biochemistry. 21(17):4014-4023 (1982).
Valerio et al., "Isolation of cDNA clones for human adenosine deaminase" Gene. 25(2-3):231-240 (1983).
Van der Weyden et al., "Human adenosine deaminase. Distribution and properties," J Biol Chem. 251(18):5448-5456 (1976).
Van Lunzen et al., "Transfer of autologous gene-modified T cells in HIV-infected patients with advanced immunodeficiency and drug-resistant virus" Mol Ther. 15(5):1024-1033 (2007).
Zychlinski et al., "Physiological promoters reduce the genotoxic risk of integrating gene vectors," Mol. Ther. 16(4):718-25 (2008).

* cited by examiner

FIG. 1A
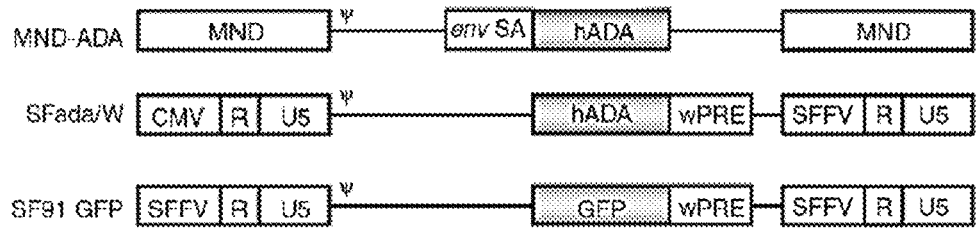
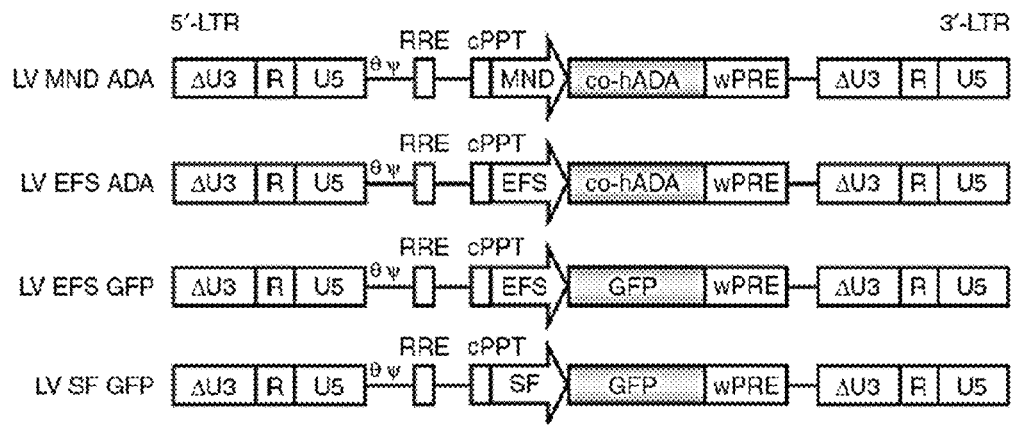
FIG. 1B
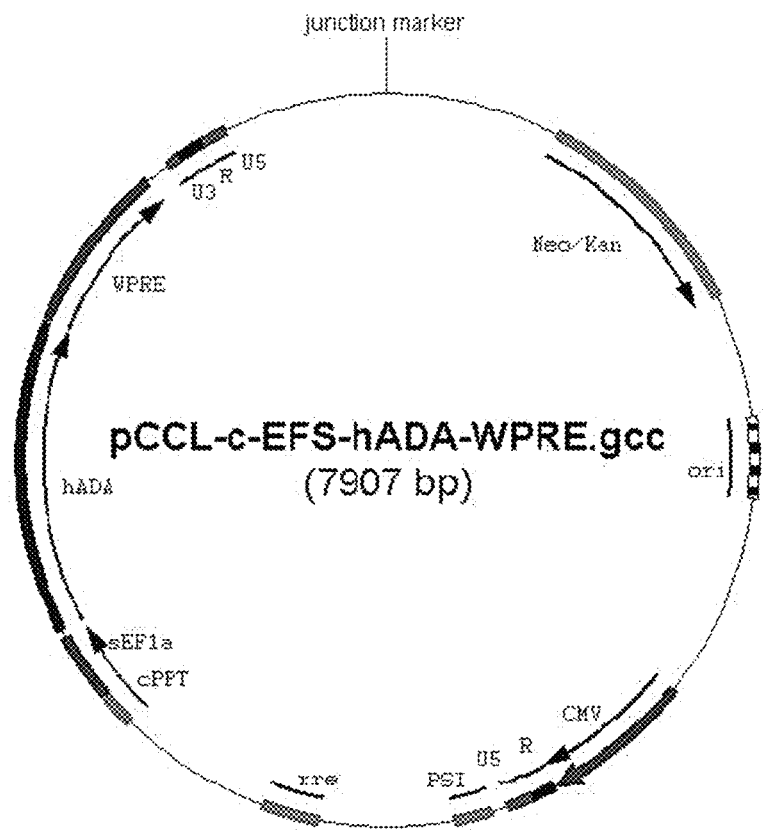

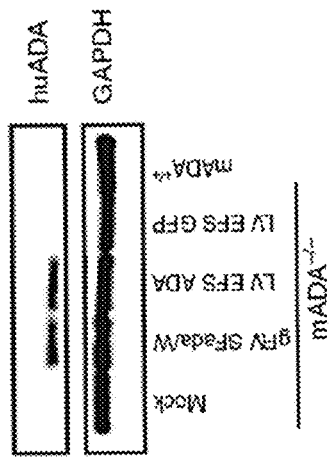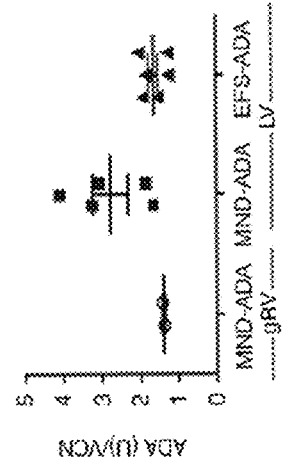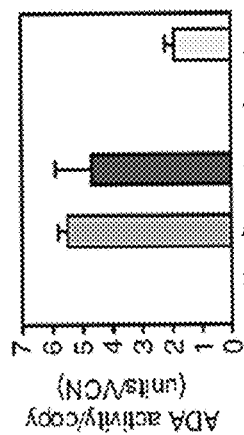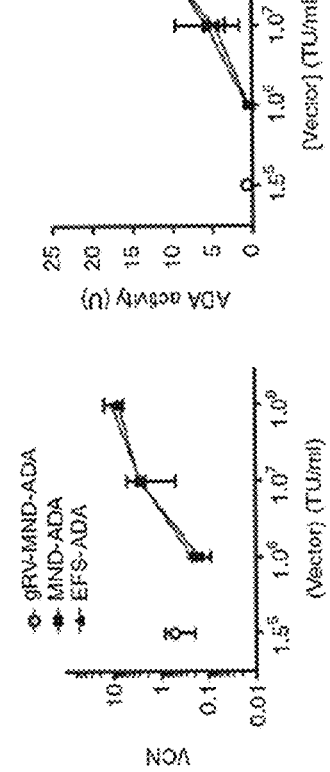
FIG. 2A
FIG. 2B
FIG. 2C
FIG. 2D
FIG. 2E
FIG. 2F FIG. 3A
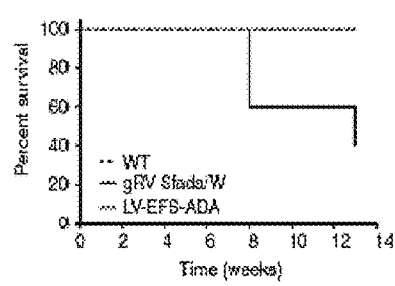
FIG. 3D
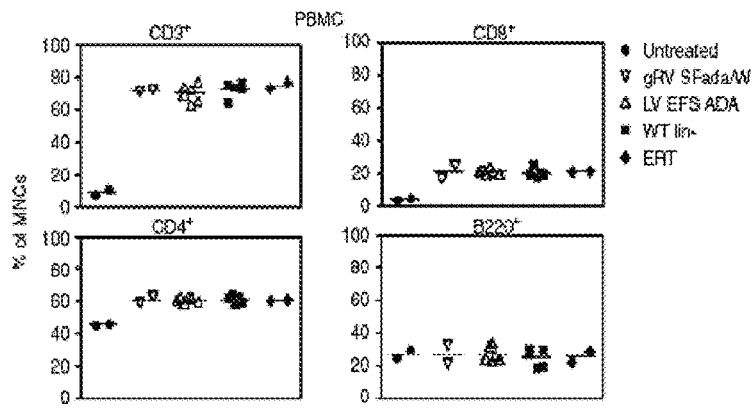
FIG. 3B
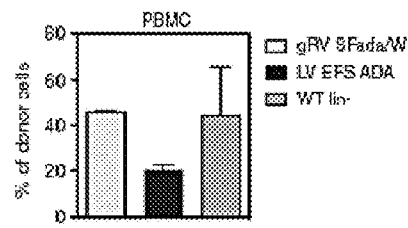
FIG. 3E
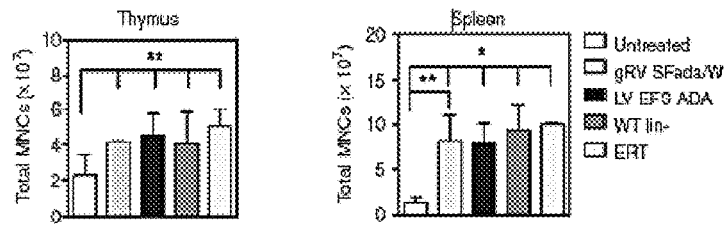
FIG. 3C
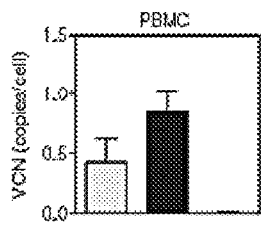
FIG. 3F
FIG. 3G
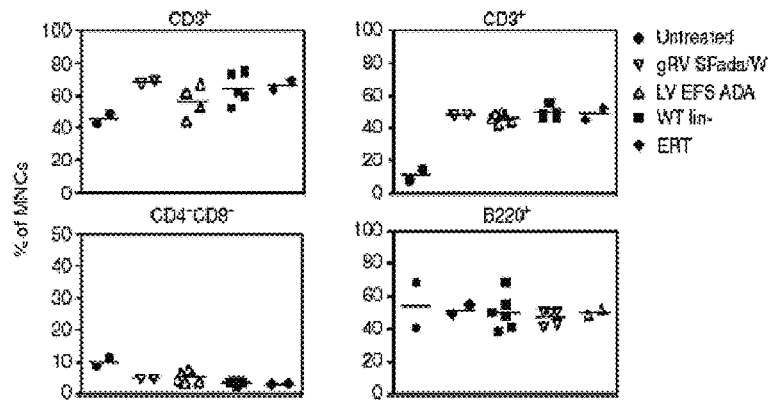

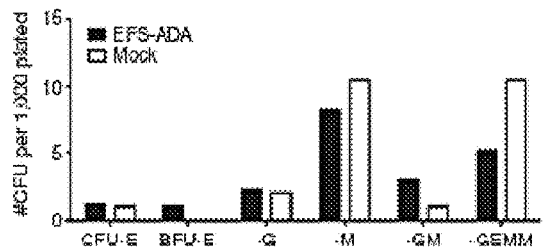
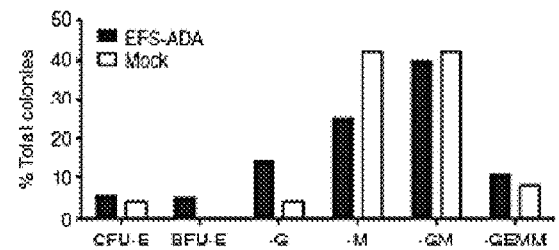
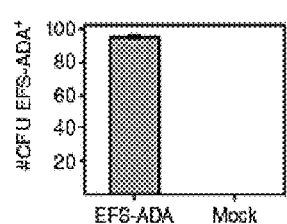
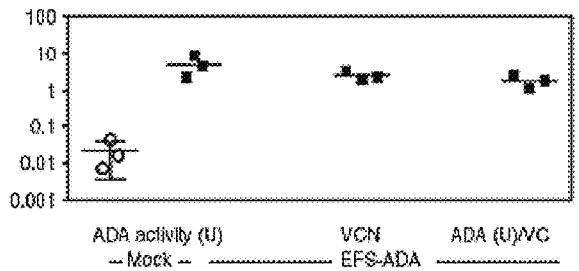
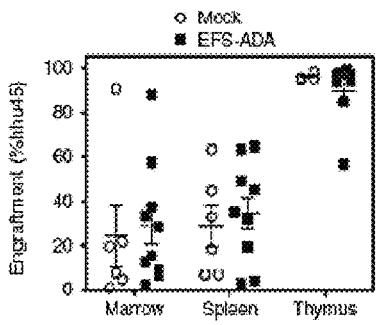
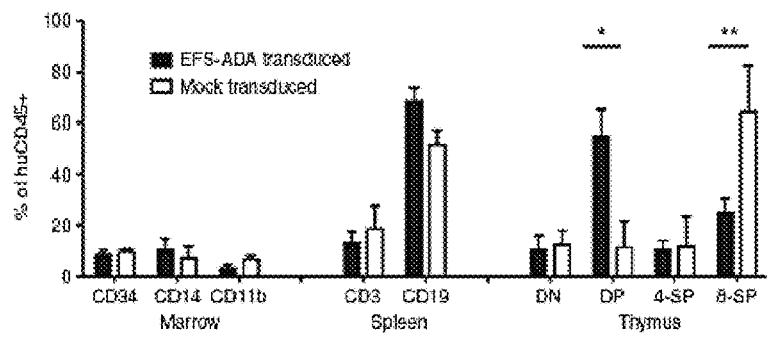
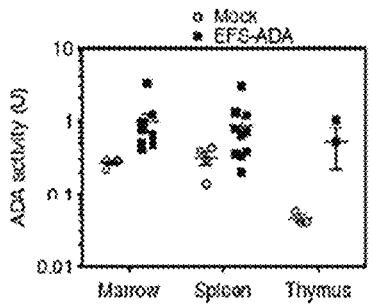
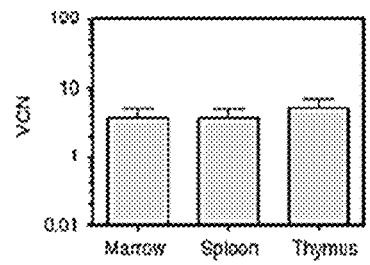
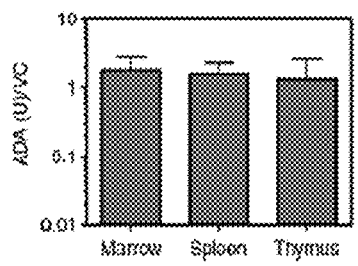

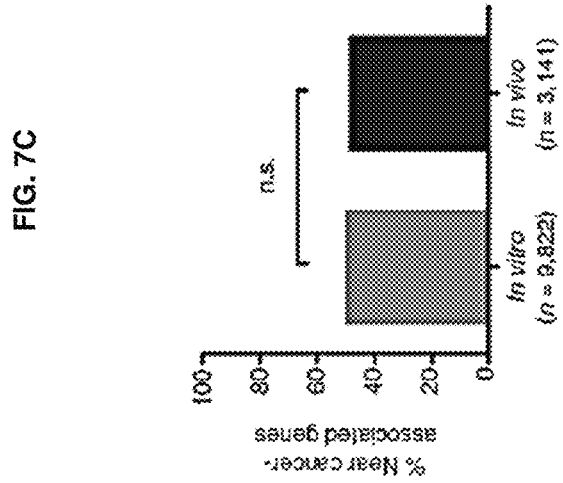
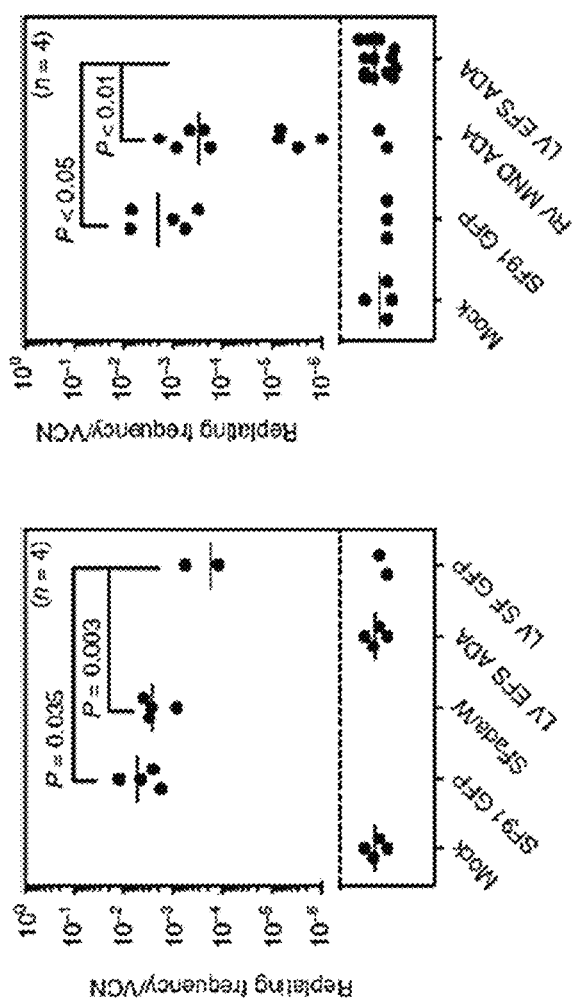
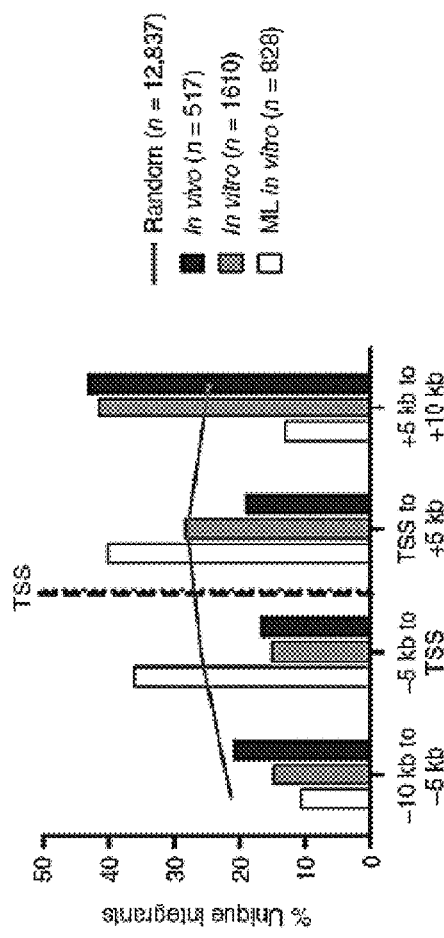

FIG. 10A
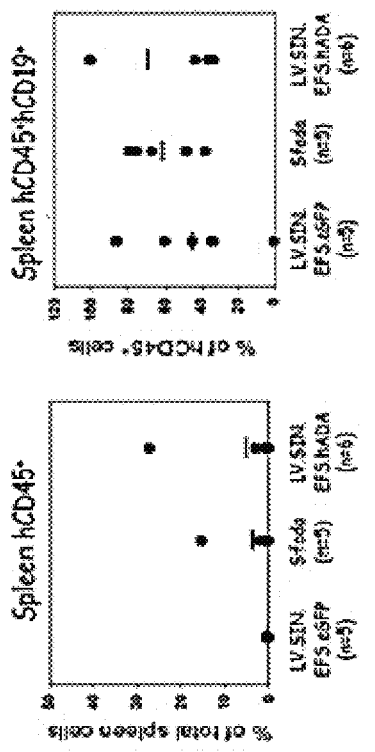
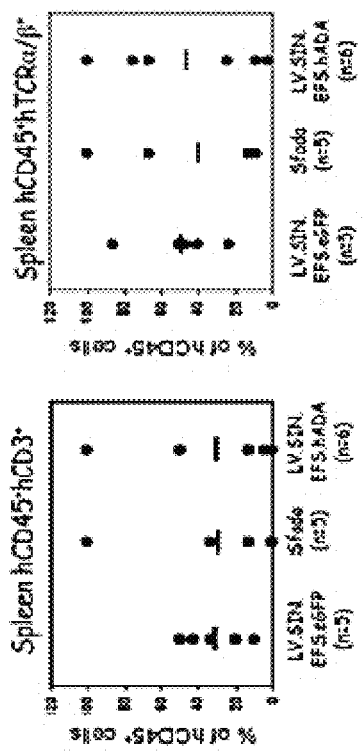
FIG. 10B
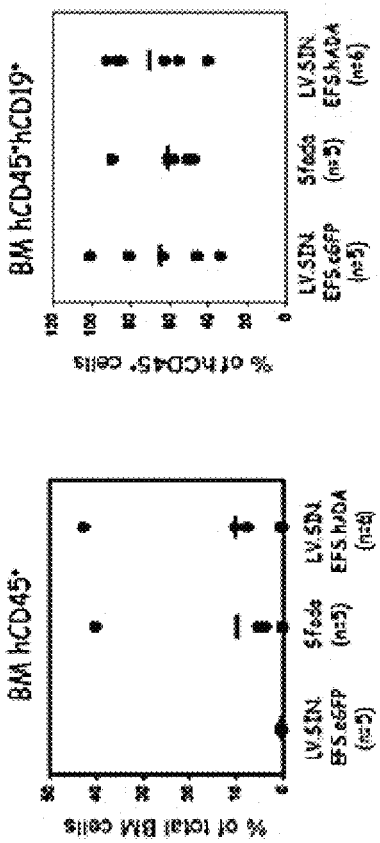
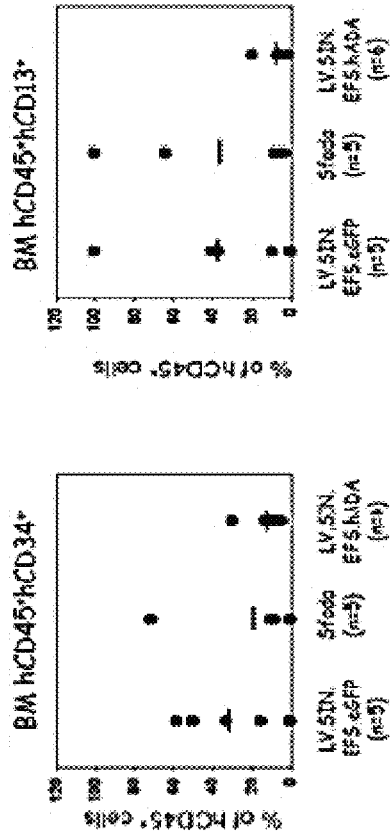

| Vector | Replating clone number (100 cells/well) | Normalized Replating clone number (100 cells/well) | VCN per cell | Replating frequency | Replating index |
|---|---|---|---|---|---|
| Mock | 9 | 0 | 0.007 | 0 | 0 |
| | 11 | 0 | 0.008 | 0 | 0 |
| | 5 | 0 | 0.000 | 0 | 0 |
| SF91.dsRED | 17 | 8 | 4.0 | 0.00087 | 0.00019 |
| | 17 | 6 | 4.7 | 0.00065 | 0.00014 |
| | 17 | 7 | 0.9 | 0.00076 | 0.00084 |
| SF91.dsRED | 27 | 18 | 5.4 | 0.00208 | 0.00039 |
| | 33 | 22 | 4.6 | 0.00250 | 0.00054 |
| | 16 | 4 | 1.4 | 0.00043 | 0.00031 |
| SF91.GFP | 65 | 56 | 1.3 | 0.00875 | 0.00684 |
| | 24 | 11 | 1.4 | 0.00122 | 0.00089 |
| | 34 | 8 | 0.2 | 0.00208 | 0.01225 |
| LV.SIN.EFS.hADA | 3 | 0 | 5.3 | 0 | 0 |
| | 6 | 0 | 4.2 | 0 | 0 |
| | 3 | 0 | 2.7 | 0 | 0 |

FIG. 16A

| Test | Result | Specification |
|---|---|---|
| Total cell dose | 1x10^8: 1.78 x10⁶<br>5x10^7: 1.78 x10⁶ | N/A |
| Gram stain | N.D. scale up in R&D lab | No organisms seen |
| Culture D1 | N.D. scale up in R&D lab | No organisms seen |
| Transduction efficiency (mean copies/cell) | 1x10^8: 1.34 copy/cell<br>5x10^7: 0.96 copy/cell | >0.3 copies/cell |

FIG. 16B

| Day | Culture Conditions | Total CD34+ | True stem cells |
|---|---|---|---|
| D0 | Untransduced | 94% | 55% |
| D3 | Untransduced | 89% | 51% |
| D3 | 1 x 10^8 Ig/ml | 92% | 58% |
| D3 | 5 x 10^7 Ig/ml | 91% | 58% |

*P1,2,4,5 were treated off trial
** P4 had S.Aureus infection of transduced cells and was taken off trial
*** P8 transduction efficiency fell below the 0.5VCN criteria for transduction efficiency. All others were above this threshold FIG. 21A Lymphocytes
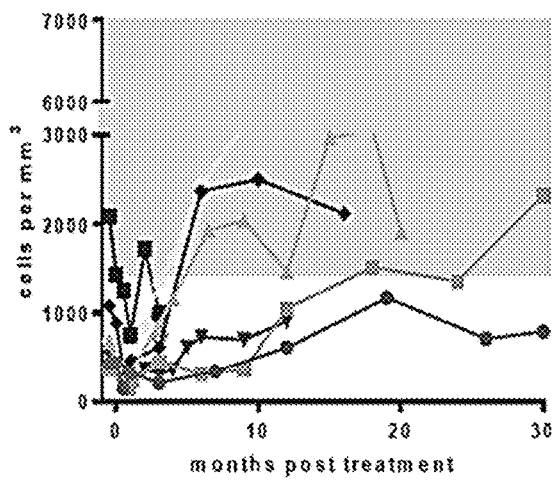
FIG. 21B CD3
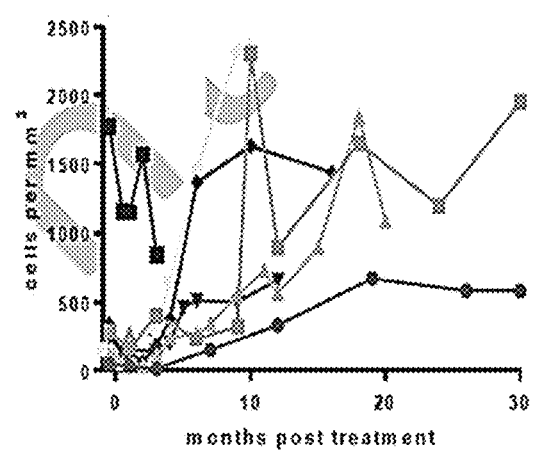
FIG. 21C CD4
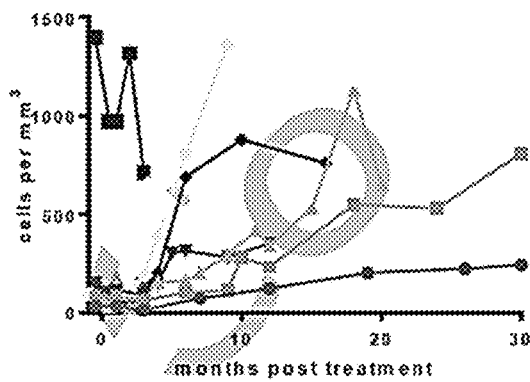
FIG. 21D CD8
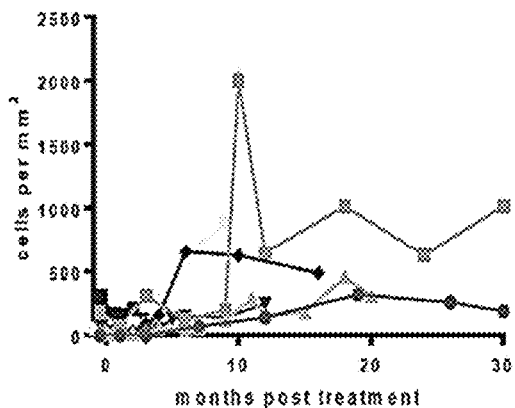

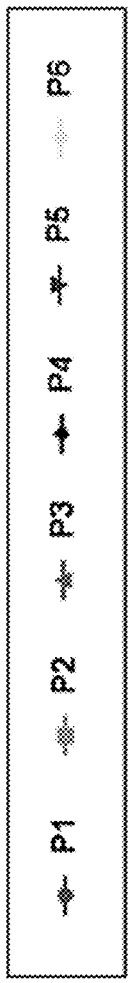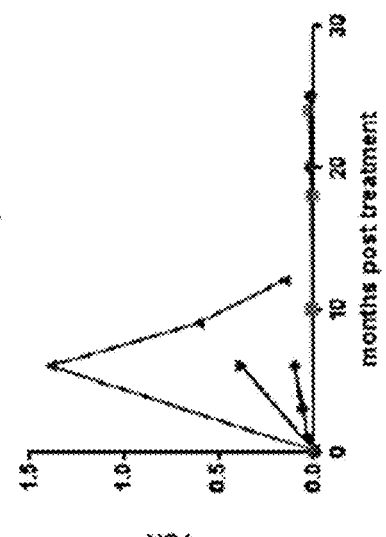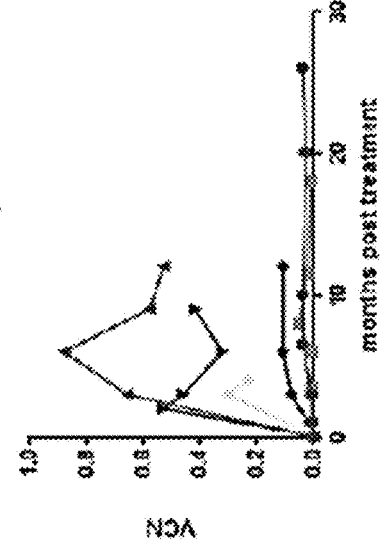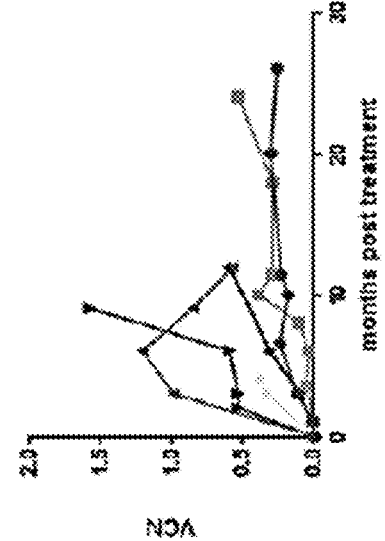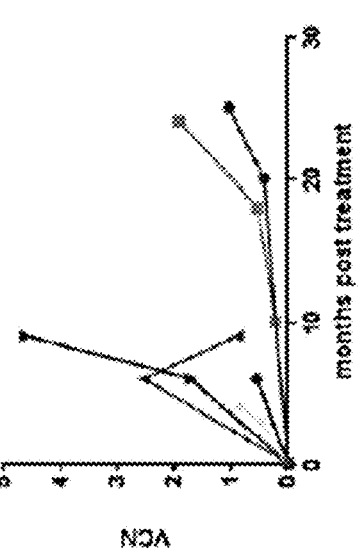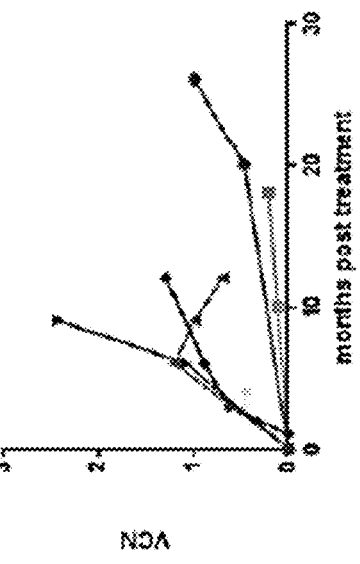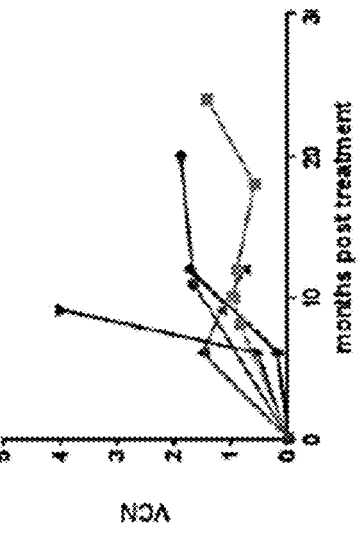
FIG. 22A, FIG. 22B, FIG. 22C, FIG. 22D, FIG. 22E, FIG. 22F

METHOD FOR TREATING ADENOSINE DEAMINASE SEVERE COMBINED IMUNODEFICIENCY

STATEMENT REGARDING FEDERALLY SPONSORED RESEARCH OR DEVELOPMENT

This invention was made with government support under Grant Numbers AI100801 and HL073104,awarded by the National Institutes of Health. The government has certain rights in the invention.

FIELD OF THE INVENTION

The present invention relates to gene therapy (GT) for the treatment and/or prevention of adenosine deaminase-deficient severe combined immunodeficiency (ADA-SCID).

BACKGROUND OF THE INVENTION

Adenosine deaminase-deficient severe combined immunodeficiency (ADA-SCID) is a severe rare primary immunodeficiency characterized by impaired T-, B-, and NK-cell development and accounts for 10-15% of all cases of SCID (Hershfield et al. 1998). Typically, ADA-SCID is an autosomal recessive monogenic metabolic condition that causes immunodeficiency. It is caused by deficiency in the enzyme adenosine deaminase (ADA). The enzyme (ADA) catalyses the deamination of deoxyadenosine and adenosine to deoxyinosine and inosine respectively, and the lack of normal levels of ADA leads to increased intracellular conversion of deoxyadenosine to deoxyadenosine triphosphate (dATP) thus expanding the dATP pool. High levels of dATP affect lymphocyte development, viability, and function causing the immune defects seen in this condition (Apasov et al. 2001).

Clinically, patients present with failure to thrive, recurrent and opportunistic infections and death in the first year of life if left untreated (Albuquerque and Gaspar 2004; Ratech et al. 1985). A murine model recapitulates the human disease with similar metabolic and immunological abnormalities and untreated mice die after 3 weeks from pulmonary insufficiency, which results from the metabolic consequences of the disease (Blackburn et al. 1998).

Treatment options for ADA-SCID are limited and the mainstay of treatment is allogeneic hematopoietic stem cell transplant (HSCT). However, survival following HSCT from matched unrelated donors (67%), mismatched unrelated donors (29%), or parental donors (43%) is poor (Booth et al. 2006). Enzyme replacement therapy (ERT) with pegylated bovine ADA (PEG-ADA) results in metabolic detoxification, but long-term immune recovery is suboptimal and very poor in some cases (Gaspar et al. 2009). A further limitation to PEG-ADA therapy is the cost. As an orphan drug, the cost is high and treatment of a small child may cost between £150,000 to £300,000 per year. With increase in age and size, these costs will increase, since ADA therapy is palliative and not curative, treatment must be continued throughout the life of the patient. Thus, there is a clear need for effective and sustained alternative treatment options.

Early trials of GT using γ-retroviral vectors (gRVs) targeting correction of peripheral blood (PB) lymphocytes or autologous hematopoietic stem cells (HSCs) or a combination of the two showed only limited success, and any observed immune recovery could not be attributed to the GT, since ERT was continued after the GT procedure (Blaese et al. 1995). Indeed, in the three studies so far undertaken, immune reconstitution remains suboptimal with T-cell numbers at the lower limit of the normal range and approximately half of the patients remaining on immunoglobulin replacement therapy due to incomplete B-cell reconstitution (Aiuti et al. 2009; Candotti et al. 2012; Gaspar et al. 2011).

Further, the ongoing use of gRVs has raised concerns, as GT for monogenic diseases has often been complicated by the development of adverse effects. In clinical trials of gRV-mediated autologous HSC GT for SCID-X1, X-CGD and Wiskott-Aldrich syndrome, there has been a high incidence of gRV-mediated insertional mutagenesis (Bortug et al. 2010; Hacein-Bey-Abina et al. 2008; Hacein-Bey-Abina et al. 2003; Howe et al. 2008; Ott et al. 2006; Stein et al. 2010). Upon vector integration, the strong enhancer elements that reside in the long terminal repeat (LTR) promoter elements of gRVs can transactivate adjacent genes to initiate the transformation process. In ADA gRV studies, vector insertions near known oncogenes have also been reported (Aiuti et al. 2007).

Thus, although HSCT and ERT are used clinically to try and manage the progression of ADA-SCID, and trials with gRVs have taken place, effectiveness of these treatment options is limited by the availability of suitable donor tissue, adverse immune responses such as Graft versus Host Disease (GvHD), poor efficacy such as poor gene marking and/or poor immune recovery, and/or safety concerns.

SUMMARY OF THE INVENTION

We have designed self-inactivating (SIN) vectors, based on the human immunodeficiency virus 1 (HIV-1) lentiviral vector (LV), in which the HIV LTR is deleted and transgene expression placed under the control of a regulatory region, and in particular the EFS short form of the elongation factor alpha promoter (EFS). More specifically, we have designed a SIN LV for the treatment of ADA-SCID. The advantages of this vector are that following correction of haematopoietic stem cells (HSCs) and/or peripheral blood stem cells (PBSCs), the promoter drives expression of the transgene in lymphoid and myeloid cells. This leads to expression of the transgene in lymphoid and myeloid cells. This provides a very effective systemic delivery system, since lymphoid and myeloid cells can circulate around the body and are generally not confined to any one tissue. In addition, the advantages of a SIN LV include the improved ability of the LV to transduce long-term engrafting HSCs and/or PBSCs, which may allow improved immune recovery but also the significantly decreased potential for insertional mutagenesis.

A vector design of this nature can provide high levels of systemic therapeutic gene delivery for correction of diseases where the gene needs to be expressed in many different parts of the body and not just in haematopoietic cells. This pertains to many metabolic diseases where there are often numerous different tissue abnormalities. We have already carried out in vitro comparative studies using LVs expressing human ADA under the transcriptional control of either the phosphoglycerate kinase promoter, the MND retroviral vector LTR, or the EFS promoter (Carbonaro et al. 2014).

However, in a series of gene therapy experiments in a murine model of ADA deficiency, we have now also shown that the LV EFS ADA vector promotes immune recovery. We have also shown that the LV EFS ADA is capable of effective and consistent ADA gene transfer and expression that is equivalent or greater than the currently used gRV, while at the same time having a significantly lower capacity for inducing clonal outgrowth for example of myeloid cells. This is true even when the vector copy number (VCN) is the same in the gRV- and LV-containing cells. This is surprising, as it was previously thought that due to the very strong promoter present in the gRV vectors previously used, expression from a gRV would be stronger.

Further, we have generated clinical data demonstrating that the LV EFS ADA vector is effective at treating patients with ADA-SCID. In particular, we have shown impressive and surprising immune recovery in treated patients, and metabolic recovery over time in treated patients. Treated patients remained metabolically detoxified and have remained off ERT. Additionally, in contrast with vectors used previously, such as those based on gRVs, the expression of transgenes from SIN LV vectors, and in particular expression of ADA from the LV EFS ADA vector of the present invention, is such that the risk of genomic disruption is minimised and the risk of transactivation of adjacent genes at the integration site associated with gRV vectors can be reduced.

Accordingly, the invention provides the following aspects:

[1] a method of treating or preventing adenosine deaminase severe combined immunodeficiency (ADA-SCID) in a patient in need thereof, comprising administering a therapeutically effective amount of a host cell or cell population, wherein said host cell or cell population contains a vector or expression cassette comprising a regulatory region, wherein said regulatory region comprises an elongation factor 1-alpha short isoform (EFS) promoter; and wherein said regulatory region regulates the expression of an adenosine deaminase (ADA) transgene operably linked to said regulatory region;

[2] use of a host cell or cell population that contains a vector or expression cassette comprising a regulatory region, wherein said regulatory region comprises an EFS promoter, and wherein said regulatory region regulates the expression of an ADA transgene operably linked to said regulatory region, for the manufacture of a medicament for treating or preventing ADA-SCID in a patient in need thereof;

[3] a host cell or cell population that contains a vector or expression cassette comprising a regulatory region, wherein said regulatory region comprises an EFS promoter; and wherein said regulatory region regulates the expression of an ADA transgene operably linked to said regulatory region, for use in a method of preventing or treating ADA-SCID;

[4] the host cell for use, cell population for use, method or use of any one of the previous aspects, wherein:
  (a) the vector or expression cassette is present at a copy number of 1, 2, 3, 4, 5, 6, 7, 8, 9 or 10 copies per single cell; or
  (b) the vector or expression cassette is present at a median copy number of from 0.5 to 6 in said cell population;

[5] the host cell for use, cell population for use, method or use of any one of the previous aspects, wherein said vector is a self-inactivating lentiviral vector comprising said transgene operably linked to an EFS promoter, wherein said vector further comprises a the woodchuck hepatitis post-transcriptional regulatory element (wPRE) element;

[6] the host cell for use, cell population for use, method or use of any one of the previous aspects, wherein said transgene is codon-optimised for expression a human cell;

[7] the host cell for use, cell population for use, method or use of any one of the previous aspects, wherein the vector is a self-inactivating vector based on the human immunodeficiency virus 1 (HIV-1) lentiviral vector;

[8] the host cell for use, cell population for use, method or use of any one of the previous aspects, wherein the transgene is SEQ ID NO: 1, or fragment thereof, or variant thereof having at least 90% sequence identity to SEQ ID NO: 1;

[9] the host cell for use, cell population for use, method or use of any one of the previous aspects, wherein the cell is a human cell or the population is a population of human cells;

[10] the host cell for use, cell population for use, method or use of any one of the previous aspects, wherein:
  (a) the cell is a bone marrow cell or the cell population comprises bone marrow cells; and/or
  (b) the cell is isolated from peripheral blood or the cell population is isolated from peripheral blood; and/or
  (c) the cell is derived from cells obtained by leukopheresis following G-CSF stimulation;

[11] the host cell for use, cell population for use, method or use of any one of the previous aspects, wherein:
  (a) the cell is an haematopoietic stem cell (HSC) and/or a peripheral blood stem cell (PBSC); or
  (b) the cell population comprises HSCs and/or PBSCs;

[12] the host cell for use, cell population for use, method or use of any one of the previous aspects, wherein the cell or cell population expresses CD34 and/or the cell population is enriched for CD34 expressing cells;

[13] the host cell for use, cell population for use, method or use according to [12], wherein cells expressing CD34 and/or cell populations enriched for cells expressing CD34 are isolated after pre-stimulation in medium supplemented with Flt3L, IL-3, TPO and SCF;

[14] the host cell for use, cell population for use, method or use of any one the previous aspects, wherein expression of ADA and/or the metabolic activity of ADA is corrected to wild type or above wild type levels;

[15] the host cell for use, cell population for use, method or use of any one of the previous aspects, wherein expression of ADA and/or activity of ADA higher than the equivalent expression and/or activity associated with a gamma retroviral vector present at the same average vector copy number as the lentiviral vector;

[16] the host cell for use, cell population for use, method or use according to [14] or [15], wherein expression of ADA and/or activity of ADA is corrected in PBMCs and/or RBCs;

[17] the host cell for use, cell population for use, method or use of any one of the previous aspects, wherein immunological defects are corrected;

[18] the host cell for use, cell population for use, method or use according to [17], wherein the CD3 count, CD4 count, CD8 count, naïve T cell count, T-cell receptor excision circles (TREC) levels and/or immunoglobulin levels are corrected;

[19] the host cell for use, population for use, method or use of according to any one of the previous aspects, wherein correction is sustained for at least 1 month post-administration, at least 3 months post-administration, at least 6 months post-administration, at least 12 months post-administration, at least 24 months post-administration or at least 48 months post-administration;

[20] the host cell for use, cell population for use, method or use of any one of the previous aspects, wherein the host cell of cell population is derived from the same patient, an individual who is related to the patient, or an individual who is a tissue type match for the patient;

[21] the host cell for use, cell population for use, method or use of any one of the previous aspects, wherein the host cell of cell population is derived from an individual with a different genetic background from the patient to which it is administered;

[22] the host cell for use, cell population for use, method or use of any one of the previous aspects, wherein the host cell or cell population is introduced into the blood and/or the bone marrow;

[23] the host cell for use, cell population for use, method or use according to any of the previous aspects, wherein:

(a) the vector or expression cassette is a lentivirus vector or expression cassette comprising a lentivirus genome or a derivative thereof, further wherein the vector or expression cassette is based on a third generation backbone; and (b) the transgene is flanked by a long terminal repeat (LTR) and a central polypurine tract (cPPT) at the 5' end, and a wPRE sequence and a LTR lacking the U3 region at the 3' end;

[24] the host cell for use, cell population for use, method or use according to any of the previous aspects, wherein said cell is not derived from embryonic or foetal tissue;

[25] a host cell or cell population as defined in any one of the previous aspects;

[26] the cell population according to [25], wherein the cell population is cryopreserved;

[27] a kit comprising the host cell or cell population according to any one of the previous aspects, wherein the kit further comprises a pharmaceutically acceptable excipient;

[28] a method of making the host cell or cell population of any one of the previous aspects comprising introducing into said cell or cell population a self-inactivating vector based on the HIV-1 vector, wherein said vector encodes ADA under the control of an EFS promoter, and wherein said vector comprises a wPRE element;

[29] a method of making the host cell or cell population of any one of the previous aspects comprising introducing into said cell or cell population a self-inactivating vector based on the HIV-1 lentiviral vector comprising the sequence of SEQ ID NO: 2, or a fragment thereof, or a variant thereof having at least 90% sequence identity to SEQ ID NO: 2;

[30] the method according to [28] or [29], comprising isolating a cell or cell population from a human;

[31] the method according to any one of [28] to [30], further comprising culturing the isolated cell or cell population;

[32] the method of any one of [28] to [31], further comprising introducing the isolated or cultured cell or cell population into:

(a) the first organism;

(b) a second organism that is related to the first organism;

(c) a second organism that is a tissue type match for the first organism; or (d) a second organism with a different genetic background to the first organism;

[33] a nucleic acid sequence for correction of metabolic activity and/or immunological defects comprising, in operable linkage in the 5' to 3' direction, cPPT, the EFS nucleic acid sequence, a transgene, and the wPRE; or a variant thereof having at least 90% sequence identity, a fragment thereof, or a complement thereof; wherein the transgene is SEQ ID NO: 1, or a fragment thereof, or a variant thereof having at least 90% sequence identity to SEQ ID NO: 1; and

[34] the nucleic acid sequence of [33], wherein said nucleic acid sequence is:

(a) flanked at the 5' end by a LTR lacking the U3 region; and (b) flanked at the 3' end by a LTR.

BRIEF DESCRIPTION OF THE DRAWINGS

FIG. 1A is a schematic representation of retroviral vectors (gRV) (top): the γ-retroviral vector, MND-MFG-ADA (gRV MND ADA) contains the MND retroviral long terminal repeats (LTRs) flanking the wild-type human adenosine deaminase cDNA (hADA) with the Moloney murine leukemia virus packaging region (Ψ) and env splice acceptor fragment (env SA). The RVSFada/W vector contains hADA driven by SFFV LTR. Lentiviral vectors (LV) (bottom): All LVs contain the enhancer-deleted "SIN" LTR (indicated by the X in the U3 region), the primer binding site (θ), the human immunodeficiency virus 1 (HIV-1) packaging signal (Ψ), the central polypurine tract (cPPT), the rev-responsive element (RRE). LV MND ADA contains the MND LTR U3 region enhancer/promoter (MND) driving expression of the hADA cDNA. LV EFS ADA contains the human elongation factor-α gene "short" promoter (EFS) driving expression of the codon-optimized human ADA cDNA (co-hADA) and a woodchuck hepatitis virus post-transcriptional regulatory element (wPRE). The LV EFS GFP vector contains the EFS promoter and green fluorescent protein (GFP).

FIG. 1B is a schematic of the structure of the EFS-ADA lentiviral vector. The pCCL self-inactivating ("SIN") lentiviral vector is derived from HIV-1 (Dull et al. 1998). All open-reading frames of HIV-1 genes have been deleted from the vector, leaving only 2007 bp (20.65% of HIV-1 genome) from HIV-1 consisting of: the "SIN" LTRs, the packaging sequences (Ψ), the RRE and the cPPT. The 400 bp SIN deletion from the LTRs removes the promoter and enhancer (from −418 to −18 relative to the U3/R border), leaving only 53 bp with the attachment sequences for chromosomal integration and the polyadenylation signal. A "short" promoter fragment (239 bp) from the human EF1α gene, lacking intronic or enhancer sequences (EFS), drives transcription of a normal human ADA cDNA (Zychlinski et al. 2008). The transcriptionally disabled wPRE is downstream. The wPRE sequence used here is devoid of the hepadnaviral X-protein open reading frame and contains a point mutation that destroys the largest residual open reading frame of this element (Schambach et al. 2006). The same wPRE sequence has previously been used without evidence of side effects in a phase-I-clinical trial in HIV-infected patients receiving autologous T cells transduced with an anti-HIV γ-retroviral LTR vector containing this element (Van et al. 2007).

FIG. 2A is a graph of ADA activity in murine ADA−/− bone marrow lineage negative (Lin−) progenitors 72 hours after transduction with lentiviral or retroviral vectors at a multiplicity of infection (MOI) of 20.

FIG. 2B is a photograph of a Western blot for ADA expression with whole cell lysates of murine ADA−/− bone marrow lineage negative (Lin−) progenitors 72 hours after transduction with lentiviral or retroviral vectors at a multiplicity of infection (MOI) of 20.

FIG. 2C is a graph of an assay for vector copy number (VCN) by quantitative polymerase chain reaction (qPCR) in human cord blood CD34+ cells transduced with the vectors at the indicated vector concentration and grown for 2 weeks in myeloid differentiation culture. Mean and standard deviation of ADA activities were calculated from experiments performed with cells obtained from three different ADA−/− donors.

FIG. 2D is a graph of ADA enzyme activity measured by colorimetric assay in human cord blood CD34+ cells transduced with the vectors at the indicated vector concentration and grown for 2 weeks in myeloid differentiation culture. Mean and standard deviation of ADA activities were calculated from experiments performed with cells obtained from three different ADA−/− donors.

FIG. 2E is a graph of the ADA enzyme activity present per VC in human cord blood CD34+ cells transduced with the vectors at the indicated vector concentration and grown for 2 weeks in myeloid differentiation culture. Mean and standard deviation of ADA activities were calculated from experiments performed with cells obtained from three different ADA−/− donors. Horizontal bars indicate mean±SEM.

FIG. 2F is a table displaying ADA enzyme activity after a 2-week in vitro myeloid culture: endogenous in human hematopoietic cells and expressed by EFS-ADA after CD34+ cell transduction. ADA, adenosine deaminase; SCID, severe combined immunodeficiency.

FIG. 3A is a graph of the survival rate indicated by Kaplan-Meier curves of ADA−/− recipients were transplanted with transduced ADA−/− BM Lin− cells (LV EFS ADA, n=6) and gRVSFada/W (SFada/W, n=5), respectively, at a multiplicity of infection (MOI) of 20. Control mice were injected with untransduced BM Lin− cells from ADA+/+ donors (WT Lin−, n=5). All LV EFS ADA and WT mice were alive at 13 weeks compared to gRVSFada/W group, where two mice died at 7 weeks and one died at 12 weeks with the remaining two alive at 13 weeks (P=0.02). All surviving mice were euthanized for analysis unless otherwise indicated.

FIG. 3B is a graph of the percentage of donor cells in total PB mononuclear cells (PBMCs) measured by quantitative PCR (qPCR).

FIG. 3C is a graph of the vector copy number (VCN) in PBMCs of transplanted ADA−/− mice. Percentage of DNA with Y chromosome were evaluated in sex-mismatched transplants indicated in FIG. 1A (Mean±SD).

FIG. 3D is a series of plots of FACS analyses of circulating mature T and B cells in peripheral blood of ADA−/− transplants. Untreated ADA−/− mice (untreated, 18 days old, n=2) and 4-5 months old PEG-ADA treated ADA−/− mice (ERT, n=2) were analyzed as controls. Data are displayed as percentage of CD3+, CD4+, CD8+, and B220+ cells in PBMCs. Horizontal bars indicate the average values.

FIG. 3E is a series of graphs of total mononucleated cell counts in thymi and spleens (*P<0.001; **P<0.05). Results are given as mean±SD.

FIG. 3F is a series of plots of FACS analyses of thymocytes of ADA−/− recipients and control mice. Data are presented as percentage of total CD3+ and CD4−CD8− cells in mononucleated cells. Horizontal bars indicate the average values.

FIG. 3G is a series of plots of FACS analyses of splenocytes in ADA−/− recipients and control mice. Data are presented as percentage of CD3+ and B220+ cells in total mononucleated cells. Horizontal bars indicate the average values.

FIG. 6A is a graph representing the enumeration of lineage committed progenitors from ADA-deficient severe combined immunodeficiency (SCID) bone marrow CD34+ cells from two donors in three separate experiments were isolated and transduced with the EFS-ADA vector at $3 \times 10^7$ TU/ml or mock-transduced, cultured in short-term myeloid culture for 2 weeks and then harvested and analyzed.

FIG. 6B is a graph representing the frequency of colonies of different lineages from EFS-ADA transduction of ADA-deficient SCID bone marrow CD34+ cells from two donors in three separate experiments were isolated and transduced with the EFS-ADA vector at $3 \times 10^7$ TU/ml or mock-transduced, cultured in short-term myeloid culture for 2 weeks and then harvested and analyzed.

FIG. 6C is a graph representing the transduction efficiency determined by the presence of vector sequence in DNA from isolated colonies from EFS-ADA transduction of ADA-deficient SCID bone marrow CD34+ cells from two donors in three separate experiments were isolated and transduced with the EFS-ADA vector at 3×10$^7$ TU/ml or mock-transduced, cultured in short-term myeloid culture for 2 weeks and then harvested and analyzed.

FIG. 6D is a graph of in vitro ADA activity (U) measured in mock-transduced and in EFS-ADA transduced bone marrow CD34+ cells and the VCN and expressed ADA activity (U)/VC measured in the EFS-ADA transduced cultures.

FIG. 6E is a graph representing the engraftment of human (% hCD45+) cells in the bone marrow, thymus, and spleen of NSG mice 4 months after transplantation with mock-transduced or EFS-ADA-transduced human ADA-deficient SCID bone marrow CD34+ cells.

FIG. 6F is a graph of human CD45+ leukocyte populations in bone marrow, thymus, and spleens from NSG mice in cells isolated from the bone marrow (huCD45-selected), thymus (total thymocytes), and spleen (huCD45-selected).

FIG. 6G is a graph of human CD45+ leukocyte populations immunophenotyped in bone marrow, thymus, and spleens from NSG mice by ADA enzyme activity (U) in cells isolated from the bone marrow (huCD45-selected), thymus (total thymocytes), and spleen (huCD45-selected).

FIG. 6H is a graph of human CD45+ leukocyte populations immunophenotyped in bone marrow, thymus, and spleens from NSG mice by EFS-ADA VCN in cells isolated from the bone marrow (huCD45-selected), thymus (total thymocytes), and spleen (huCD45-selected).

FIG. 6I is a graph of human CD45+ leukocyte populations immunophenotyped in bone marrow, thymus, and spleens from NSG mice by ADA activity (U/VC) in cells isolated from the bone marrow (huCD45-selected), thymus (total thymocytes), and spleen (huCD45-selected).

FIG. 7A is a graph of the replating frequency corrected for VCN group by investigators at Great Ormond Street Hospital (GOSH), UK.

FIG. 7B is a graph of the replating frequency corrected for VCN group by investigators at University of California, Los Angeles, USA.

FIG. 7C is a graph of vector integration site analysis in human ADA-deficient bone marrow in vitro. The percentages of unique integration sites in human cells (isolated from primary NSG mouse recipient bone marrow) near cancer-related genes were determined in vitro (n=9,822 unique sites) or in vivo (n=3,141 unique sites). Integration sites in genes or within 300 kb of gene TSS were considered "near" and cancer-related genes were defined as in (Higgins et al. 2006).

FIG. 7D is a graph of the EFS-ADA vector integration site analysis mapping relative to transcriptional start sites (TSS) in vitro (n=1,610 unique sites) and in vivo (n=517), and compared to a published data set for murine leukaemia virus (MLV1) (n=828). Grey line represents the theoretical random distribution (n=12,837).

FIG. 10A is a series of graphs representing the levels of bone marrow engraftment of hCD45+ cells, CD34+ cells, CD19+ B and CD13+ myeloid cells following transduction of ADA deficient CD34+ bone marrow with the LV.SIN.EF-S.eGFP, SFada and LV.SIN.EFS.hADA vectors and engraftment into immunodeficient NOD/SCID/γc−/− murine recipients.

FIG. 10B is a series of graphs representing the levels of splenic engraftment of hCD45+ cells, CD19+ B cells and CD3+ T cells and TCRα/β following transduction of ADA deficient CD34+ bone marrow with the LV.SIN.EFS.eGFP, SFada and LV.SIN.EFS.hADA vectors and engraftment into immunodeficient NOD/SCID/γc −/− murine recipients.

FIG. 16A is a table showing clinically applicable transduction conditions resulted in effective CD34+ cell transduction with viral copy numbers of ~1-1.3 copies/cell. Clinical grade LV.SIN.EFS.hADA vector was characterised for its ability to transduce CD34+ cells from ADA−/− patients. Using clinical grade reagents and a clinical protocol involving 18 hrs pre-stimulation and followed by 1 round of lentiviral transduction for 24 hrs, either $1 \times 10^8$ (~MOI of 100) or $5 \times 10^7$ (~MOI of 50) viral genomes were added to ~$1 \times 10^6$ CD34+ cells.

FIG. 16B is a table showing that there was preservation of CD34+ integrity with little change in the percentage of stem cells through the culture period form D0-D3.

FIG. 21A is a graph of lymphocyte recovery in human patients following gene therapy with the EFS-ADA lentiviral vector.

FIG. 21B is a graph of CD3 recovery in human patients following gene therapy with the EFS-ADA lentiviral vector.

FIG. 21C is a graph of CD4 recovery in human patients following gene therapy with the EFS-ADA lentiviral vector.

FIG. 21D is a graph of CD8 recovery in human patients following gene therapy with the EFS-ADA lentiviral vector.

FIG. 22A is a graph of vector copy number (VCN) measurements in PBMCs of human patients following gene therapy with the EFS-ADA lentiviral vector.

FIG. 22B is a graph of vector copy number (VCN) measurements in neutrophils of human patients following gene therapy with the EFS-ADA lentiviral vector.

FIG. 22C is a graph of vector copy number (VCN) measurements in monocytes of human patients following gene therapy with the EFS-ADA lentiviral vector.

FIG. 22D is a graph of vector copy number (VCN) measurements in T cells of human patients following gene therapy with the EFS-ADA lentiviral vector.

FIG. 22E is a graph of vector copy number (VCN) measurements in B cells of human patients following gene therapy with the EFS-ADA lentiviral vector.

FIG. 22F is a graph of vector copy number (VCN) measurements in NK cells of human patients following gene therapy with the EFS-ADA lentiviral vector.

BRIEF DESCRIPTION OF THE SEQUENCES

Figure 4A:
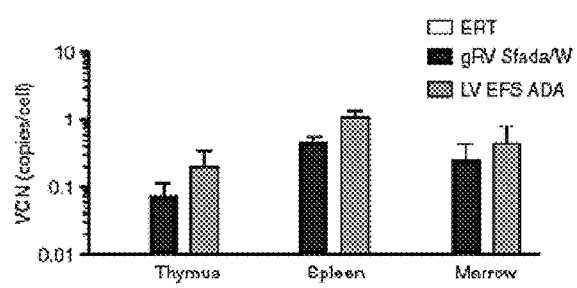
FIG. 4A is a graph of vector copy number (VCN) analysis of thymus, spleen, and bone marrow in ADA−/− recipients (mean±SD).

SEQ ID NO: 1 shows the sequence of human codon optimised ADA cDNA sequence.
SEQ ID NO: 2 shows the sequence of the LV EFS ADA lentiviral vector from the junction marker.
SEQ ID NO: 3 show the full length elongation factor 1 alpha sequence.
SEQ ID NO: 4 show the EFS sequence (i.e. the EF1a sequence used in the vector).
SEQ ID NO: 5 shows the sense qPCR primer for the HIV psi region specific for the packaging region of LVs.
SEQ ID NO: 6 shows the sequence of the antisense qPCR primer for the HIV psi region specific for the packaging region of LVs.
SEQ ID NO: 7 shows the sequence of the qPCR probe for the HIV psi region.
SEQ ID NO: 8 shows the sequence of the sense qPCR primer for GFP.
SEQ ID NO: 9 shows the sequence of the antisense qPCR primer for GFP.
SEQ ID NO: 10 shows the sequence of the qPCR probe for GFP.
SEQ ID NO: 11 shows the sequence of the sense qPCR primer for the human ADA gene.
SEQ ID NO: 12 shows the sequence of the antisense qPCR primer for human ADA gene.
SEQ ID NO: 13 shows the sequence of the qPCR probe for the human ADA gene.

SEQ ID NO: 14 shows the sequence of the sense qPCR primer for SDC4.
SEQ ID NO: 15 shows the sequence of the antisense qPCR primer for SDC4.
SEQ ID NO: 16 shows the sequence of the qPCR probe for SDC4.

DETAILED DESCRIPTION OF THE INVENTION

It is to be understood that different applications of the disclosed host cell and/or cell population containing the vector and/or expression cassette of the invention, together with specific polynucleotide sequences, may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "a host cell" includes "host cells", reference to "vector" includes two or more such vectors, reference to "an expression cassette" includes two or more expression cassettes, and the like.

All publications, patents and patent applications cited herein, whether supra or infra, are hereby incorporated by reference in their entirety.

The present invention concerns gene therapy for the treatment and/or prevention of s adenosine deaminase-deficient severe combined immunodeficiency (ADA-SCID), in a patient.

The patient may be any suitable organism. The patient is preferably a mammal. The mammal may be a commercially farmed animal, such as a horse, a cow, a sheep or a pig, a laboratory animal, such as a mouse or a rat, or a pet, such as a cat, a dog, a rabbit or a guinea pig. The patient is more preferably a human.

The vectors and expression cassettes of the present invention can be used to treat ADA-SCID. The ADA-SCID may be inherited diseases. ADA-SCID can be defined as metabolic disorder, characterised by enzyme deficiency.

ADA-SCID

Severe combined immunodeficiencies (SCID) are a heterogeneous group of inherited disorders characterised by a profound reduction or absence of T lymphocyte function. As a result, children with SCID are susceptible to recurrent and severe infection with pneumonia, diarrhoea and failure to thrive being the most common clinical manifestations. Without treatment most children die in the first year of life from overwhelming infection. SCID arises from a variety of molecular defects which affect lymphocyte development and function (Fischer et al. 1997). Adenosine Deaminase (ADA) deficient SCID accounts for approximately 10-20% of all cases of SCID and was the first form of SCID in which the underlying defect was identified (Giblett et al. 1972). Over 18 different genetic defects have now been shown to give rise to a clinical and immunological phenotype of SCID and these include: 1) defects in the lymphocyte specific signalling molecules, common γ chain (Noguchi et al. 1993), JAK-3 (Macchi et al. 1995), and IL-7 receptor α (Puel et al. 1998); 2) in molecules that control immunoglobulin gene rearrangement, RAG-1/2 (Schwarz et al. 1996), Artemis (Moshous et al. 2001) and Cernunnos ((Revy et al. 2006); and 3) in subunits of the CD3 receptor complex (Rieux-Laucat et al. 2006; Soudais et al. 1993) amongst others. The incidence of ADA-SCID is in the order of 1:200,000 and 1:1,000,000 live births (Hershfield and Mitchell 1995) although the prevalence may be higher within specific ethnic populations (Sanchez et al. 2007).

Adenosine Deaminase Deficiency

Adenosine deaminase is an enzyme that is expressed in all tissues of the body. During DNA breakdown, ADA catalyses the deamination of deoxydenosine (dAdo) and adenosine to deoxyinosine and inosine respectively (reviewed in (Hirschhorn 1993). The lack of ADA results in the accumulation of dAdo in both intracellular and extracellular compartments. Intracellularly, dAdo is then converted by deoxycytidine kinase (dCydK) to deoxyadenosinetrisphosphate (dATP) which accumulates within the cell. The buildup of these two metabolites has profound effects on lymphocyte development and function and is the most likely cause of the immunological defects. dATP inhibits the enzyme ribonucleotide reductase which is necessary for DNA replication and repair (Takeda et al. 1991; Lee et al. 1984) and also induces apoptosis in immature thymocytes. dAdo inactivates the enzyme S-adenosylhomocysteinehydrolase (SAHH) (Hershfield et al. 1979) (Benveniste et al. 1995): SAHH accumulation inhibits transmethylation reactions and the lack of SAHH activity as a consequence of ADA deficiency may also contribute to the immunodeficiency. It has also been speculated that the effects of adenosine acting through G protein receptors on the surface of thymocytes may play a role in the pathogenesis of the disease (Benveniste and Cohen 1995) (Apasov et al. 2001).

Although ADA is expressed ubiquitously, the most profound effects are manifest in the immune system (non-immunological consequences are present however and are discussed further below). This may be explained by the expression pattern of ADA which is highest in the thymus as a result of high lymphocyte turnover (Adams and Harkness 1976) (Van der Weyden and Kelley 1976) and also by increased expression of dCydK in lymphocytes which serves to increase dATP accumulation in immune cells more than in other tissues (Carson et al. 1977).

ADA Gene: Structure and Function

The ADA gene locus has been mapped to 20q13.11 (Tischfield et al. 1974) on the basis of evidence from studies of somatic cell hybrids containing translocations involving chromosome 20 (Mohandas et al. 1980), ADA activity in patients with chromosome 20 structural abnormalities (Philip et al. 1980) (Petersen et al. 1987) and in situ hybridisation with an ADA cDNA probe (Jhanwar et al. 1989). The gene spans 32 kb and is organised into 12 exons separated by 11 introns (Valerio et al. 1983). Promoter activity was localised to a 135 bp region immediately 5' of the major transcription start site (−95 relative to the AUG translation start site). The promoter consists of 82% G+C residues, lacks the TATA and CAAT sequences found in the promoter regions of many developmentally regulated genes and possesses six GC boxes homologous to the consensus binding site for Spl, a eukaryotic 'zinc finger' transcriptional activator (Kadonaga et al. 1987). The murine ADA promoter has similar characteristics (Ingolia et al. 1986).

cDNA sequences of normal human DNA were first characterized in 1983 by a number of different laboratories (Valerio et al. 1983). The 1.5 kb ADA mRNA consists of a 1089 nucleotide open reading frame together with 5' and 3' untranslated sequences. The resulting protein consists of 363 amino acids with a deduced molecular weight of 40.7 Kd but in Western blot studies the actual protein species varies between 36-44 Kd. The ADA enzyme is expressed in all tissues of the body but levels vary over a wide range (Adams and Harkness 1976). In humans, the highest activity is in the thymus and in other lymphoid tissues with lowest expression in erythrocytes. Among non-lymphoid tissues, high levels are found in the villi of the duodenal epithelium and in other areas of the gastrointestinal tract (GIT) and also in the cerebrum. There is a different pattern of expression in other species with mice having higher levels in the GIT than in the thymus (Lee 1973). ADA in human tissues exists in several different physical forms which can be distinguished electrophoretically and by size. ADA is largely an intracellular enzyme although a low level of surface associated enzyme is detectable on a fraction of blood cells (SenGupta et al. 1985). The various forms of ADA represent a combination of genetic polymorphisms and isoenzymes generated by post-translational modifications and in some tissues, binding of the monomeric catalytic ADA gene non-catalytic (200 Kd) homodimeric glycoprotein termed 'conversion factor', 'binding protein' or 'complexing protein' (ADA-CP). It has been speculated that ADA-CP may regulate the activity of ADA or contribute to extracellular Ado catabolism (Trotta 1982) or that it may mediate the renal clearance of monomeric ADA (Schrader et al. 1990). However, interaction with ADA-CP does not affect the activity of ADA and in some tissues the two proteins do not co-localise (Dinjens et al. 1989).

ADA-CP has been identified as a protein known both as CD26 and dipeptidyl peptidase IV (DPPIV) (Morrison et al. 1993). CD26 was first defined as an antigen on activated human T lymphocytes (Fox et al. 1984), and DPPIV as a widely distributed ectoenzyme that cleaves peptides including several hormones, neuropeptides, and cytokines. CD26 and DPPIV cDNAs from human T cells and intestine predict the same 766-residue, 88-Kd polypeptide. This type II membrane protein has a large extracellular domain consisting of a glycosylated "stalk", a cysteine-rich segment (residues 290-552), and a COOH-terminal region that bears the serine protease (DPPIV) active site (residues 628-632). Residues 294 and 340-343 of the cysteine-rich segment are essential for binding ADA (Dong et al. 1997). Although it was initially suggested that binding of ADA to CD26 was important for protection of lymphocytes from the extracellular effects of Ado, recent studies on a healthy adult with defective ADA-CD26 binding suggests that interaction of these proteins is not essential for the development or maintenance of immune function in humans (Richard et al. 2000).

Mutations in ADA-SCID Patients

Direct analysis of mutant ADA alleles from ADA deficient patients has revealed a wide variety of molecular defects. Most of the patients analysed are compound heterozygotes and several deletions and splicing defects have been found as have a larger number of point mutations in the coding region of the structural gene. Two large deletion mutations, one 3250 bp deletion of the promoter and exon 1 (Markert et al. 1988) and the other deleting exons 1-5 (Hirschhorn et al. 1992), led as might be expected to no mRNA production. A number of splice site mutations have been identified that result in skipping of specific exons or in activation of cryptic splice sites. Most of these mutations generate premature translation stop codons and result in a decreased level of mRNA. ADA mis sense mutations have been found throughout the coding region of the gene with no particular mutation 'hotspots' (reviewed in Hershfield and Mitchell 1995). Determination of the three-dimensional structure of the murine ADA has permitted modelling of the possible effects of the amino acid substitutions on human ADA function. Two mutations are directly involved in binding ADA substrates Glu217 (→Lys) hydrogen bonds to the N−1 atom of substrate through the side chain carboxyl and His15 (→Asp) coordinates with the zinc co-factor (Arrendondo-Vega et al. 1998). Several other mutated residues are close to the active site or to peptide segments that deploy active site residues. In vitro analysis of the residual ADA activity of mutant alleles has been determined by expression of the mutant in the ADA-deleted *E. coli* strain SO3834 (Arredondo-Vega et al. 1998). Alleles associated with severe ADA-SCID expressed 0.001%-0.6% of wild-type activity whereas 3 alleles from partial ADA deficient patients expressed 5%-28% of normal. There was also a strong inverse correlation between mutant ADA activity and dATP level at time of patient diagnosis. These data suggest that the severity of the mutation and level of residual ADA activity may influence metabolic and clinical outcome.

Although analysis of the effects of missense mutations by modelling of ADA structure or by in vitro assays may be informative, in most cases of ADA-SCID, mutant ADA protein is present at only very low levels or is undetectable by Western blotting. Thus the primary effect of some point mutations in vivo may be to increase the rate of enzyme degradation by interfering with protein folding or by destabilizing the mature protein and predisposing it to proteolysis.

The Pattern of Clinical Disease

Classical Presentations

ADA-SCID is estimated to affect between 1 in 200,000 and 1 in 1,000,000 births although the frequency may be greater in certain geographical areas (Hershfield and Mitchell 1995) (Sanchez et al. 2007). Clinically, it is characterised by severe and recurrent infections and a high frequency of opportunistic infections. The clinical presentation in ADA-SCID is similar to patients with autosomal forms of SCID and it is difficult to distinguish between the different forms of SCID on the basis of clinical presentation alone. The mean age at diagnosis for all types of SCID is 6.6 months and this most likely reflects the time when the protective effect of placentally transferred maternal immunoglobulin has diminished and children have been exposed to a range of microorganisms. The most common infective problems are oral candidiasis, respiratory infection due to *Pneumocystis jiroveci*, respiratory syncitial virus and parainfluenza 3, adenoviral infection, persistent diarrhoea and failure to thrive. In countries which administer anti-tuberculous vaccination to infants with *bacillus* Calmette-Guerin (BCG), disseminated infection with BCG has occurred. Live polio vaccine has also caused poliomyelitis and carditis but only rarely and this is probably due to the continued presence of maternal immunoglobulin at the time of initial vaccination. Physical findings are unremarkable except for evidence of infection and the absence of lymph nodes and pharyngeal lymphoid tissue.

Non-immunological Manifestations in ADA-SCID

Unlike other forms of SCID, ADA deficient patients show a number of non-immunological abnormalities which may reflect the importance of ADA expression in other systems. Costochondral abnormalities and skeletal dysplasias are well documented (Cederbaum et al. 1976) and ADA-SCID children have been noted to have a 'rachitic rosary' appearance. Other systemic abnormalities include neurological abnormalities involving motor function (Hirschhorn et al. 1980), bilateral sensorineuronal deafness (Tanaka et al. 1996), hepatic dysfunction (Bollinger et al. 1996) and renal mesangial sclerosis (Ratech et al. 1985). Nonimmunological manifestations are also found in ADA deficient mice which die perinatally from hepatocyte degeneration but also show pulmonary and intestinal defects (Migchielson et al. 1996). More recently studies on ADA-SCID patients post bone marrow transplantation show defects in cognitive and behavioural function despite correction of immunological abnormalities (Titman et al. 2008) and again highlights the systemic nature of the disease.

Delayed/Late Onset Disease

Approximately 10-15% of all cases of ADA deficient patients have a milder phenotype with less severe immunological abnormalities and clinical course. In these patients there is residual ADA activity as a result of the specific gene defect and consequently less profound metabolic derangement (Morgan et al. 1987). In these patients, recurrent infections may start to occur after 2-3 years of age and patients are eventually diagnosed following investigation for a combined immunodeficiency. At the far end of this spectrum are a handful of adults who have been diagnosed with ADA deficiency. Two sisters with a long standing history of pulmonary insufficiency and warts were identified following investigation of their CD4 lymphopenia (Shovlin et al. 1994). Other individuals with lymphopenia and diagnosis in adulthood have been described (Ozsahin et al. 1997). In these patients there was only a mild metabolic abnormality in comparison with the levels of dATP and dAdo seen in patients with full blown ADA-SCID.

Partial ADA Deficiency

A number of individuals have now been described with partial ADA deficiency. In these individuals there is differential expression of ADA in different cell lineages with very low or undetectable levels in erythrocytes (<2%) but ~4-70% of normal activity in fibroblasts (Borkowsky et al. 1980). As a result of significant activity in nucleated cells, there is very little metabolic derangement in erythrocytes and there is normal immune function. In vitro expression studies of the mutant alleles from such individuals demonstrates residual activity and suggests that there is a genotype-phenotype correlation (Daddona et al. 1983).

Reversion Mutations in ADA-SCID

Patients have now been described in whom an in vivo reversion mutation to wild type sequence has resulted in restoration of wild-type ADA activity to patient T cells. Detailed analysis of these patients showed that although B cells and other lineages showed the presence of two mutated alleles, T cell lines contained one mutant and one wild-type allele. The wild-type allele expressed a functional ADA protein resulting in half-normal ADA activity in the cell lines. In one patient in vivo reversion resulted in progressive clinical improvement and unexpectedly mild biochemical and immunological abnormalities suggesting that T cells modified to wild-type may have a powerful survival and growth advantage over ADA deficient cells (Hirschhorn et al. 1996). A similar phenomenon has been described in a patient with X-SCID and was used as an important for model for subsequently successful clinical gene therapy trials (Stephan et al. 1996). In a second individual the use of PEG-ADA resulted in a decrease in ADA activity in peripheral blood mononuclear cells which could have resulted from PEG-ADA abolishing the selective advantage of revertant cells in vivo (Ariga et al. 2001).

Diagnosis of ADA deficiency and prognosis

ADA Deficiency Unlike Many of the Other Immunodeficiencies can be Reliably diagnosed by enzymatic assays. Intracellular ADA activity can be measured by the ability of cells to convert the substrate adenosine to inosine and hypoxanthine using high performance liquid chromatography (HPLC). Further, dATP build-up in erythrocytes, accumulation of intracellular and extracellular dAdo and lack of SAHH activity are specific characteristics of the disease and can all be measured to give an accurate and unambiguous diagnosis. In carriers of the condition, intermediate levels of ADA activity have been found leading to reliable identification of carrier status. The availability of such precise enzymatic assays has to a certain extent obviated the need for genetic diagnosis, although this has been carried out in specialist laboratories.

Enzymatic assays have also been used in prenatal diagnosis of ADA deficiency. In the first trimester of pregnancy, cultured cells from chorionic villus sampling can be assayed for ADA enzymatic activity (Dooley et al. 1987). This is a more reliable source than fresh material from the CVS. In the second trimester diagnosis has been performed on cultured amniotic cells. Direct analysis of enzyme and metabolite levels in amniotic fluid has not proved useful. Genetic diagnosis is also available in specialist laboratories and is useful for confirming the findings observed by metabolic analysis. In certain cases, the use of genetic analysis and mutant allele expression has been able to shed light on the variability in severity of presentation.

Classic ADA-SCID has an extremely poor prognosis without treatment. Death occurs in the first year of life from infectious complications. Although treatments based on physical isolation into a sterile environment can provide protection from infection and prolong life (for example, the case of the 'bubble baby'), such cases are extremely rare. Upon diagnosis, patients are commenced on bacterial, viral and *pneumocystis* prophylaxis and immunoglobulin substitution therapy. In some cases fungal prophylaxis is also commenced. In a few atypical cases, patients have been maintained on this regime for a number of years. However, it is generally accepted that in the vast majority of cases, prophylactic therapy is only a means of protecting the child until more definitive treatment with either stem cell transplantation or PEG-ADA can be performed.

Previous Management Options for ADA-SCID

Haematopoietic stem cell transplant (HCT or HSCT) is the treatment choice that is most widely available to most physicians and transplant centres. However, data on the outcome of ADA-SCID transplants has previously been limited as most SCID transplant papers have presented data on the outcome of all SCID types rather than by specific molecular defect (Antoine et al. 2003)

The toxic compounds that accumulate in ADA deficiency (dATP) cross the cell membrane poorly but are metabolised to ADA substrates (dAdo) that rapidly equilibrate with plasma via the nucleoside transporter. Thus maintaining sufficient levels of circulating 'ectopic' ADA either in the plasma or in a population of cells can normalise metabolite levels in enzyme deficient cells. This was initially demonstrated by the use of repeated red cell transfusions for the treatment of ADA deficiency (Polmar 1978). Metabolic and immunological correction was seen but the effects were transient and outweighed by the risk of viral transmission and iron overload. PEG-ADA is a bovine form of ADA conjugated to polyethylene glycol. The covalently bound PEG is intended to prevent proteolysis and uptake by cells and to prolong circulating life and reduce immunogenicity. PEG-ADA has been used since 1987 for the treatment of ADA-SCID patients who lacked a genotypically identical donor (reviewed in (Hershfield et al. 1995). PEG-ADA avoids the risks of red cell transfusion and the amount of enzyme activity provided is equivalent on a ml to ml basis to ~1800 times the ADA activity of packed erythrocytes. Three mls of PEG-ADA contains the ADA equivalent of ~1012 T lymphocytes. The preparation is given as an intramuscular injection at ~30 units per kg on a weekly basis.

Data on long term follow up of immunologic function and outcome in PEG-ADA treated patients has been limited since there has been no central point for data collection. However a recent review (Gaspar et al. 2009) has highlighted outcomes in over 185 patients treated with PEG-ADA until September 2008 (about 90% of those ever treated). PEG-ADA has been used as initial therapy for patients who lacked a related HLA-identical donor, when assessment of risk and benefit by physicians and parents favoured ERT over other options (Hershfield 2004).

Overall, 70% of patients treated with PEG-ADA began ERT at <1 year of age (50% were <6 months old). Half of the remaining patients started treatment at 1-3 years of age, and half at 3-34 years of age. Many of these latter "delayed" or "late' onset patients had pulmonary disease or other consequences of chronic immune deficiency, which made them poor candidates for partially mismatched HCT with conditioning.

Up to September 2008, 98 patients were receiving PEG-ADA approximately half of the number that had begun ERT. About 20% of patients had died while on therapy; the remainder had discontinued ERT to undergo a potentially curative procedure. More than two thirds of the transplants were performed within a year of starting PEG-ADA, as soon as clinical condition was stable and a suitable donor had been identified. During the first decade after PEG-ADA received FDA approval in 1990, survival following these "elective" transplants was about 50% (Hershfield 2004), similar to that for partially mismatched transplants in ADA-deficient SCID patients who had not received prior ERT.

Gaspar et al 2009 demonstrated the estimated probability of survival versus length of treatment with PEG-ADA. Half of the deaths on ERT occurred within the first 6 months (40% in the first month), due to conditions present at diagnosis. The overall probability of surviving 20 years on ERT is estimated to be 78%. A patient alive 6 months after starting ERT had about 90% probability of surviving the next 12 years. Conditions contributing significantly (3-5 patients each) to mortality beyond 6 months include refractory hemolytic anaemia at 1-3 years; chronic pulmonary insufficiency after 5 to 15 years; and lymphoproliferative disorders after 5 to 15 years of ERT (Husain et al. 2007). Hepatocellular carcinoma developed in two patients, one just starting ERT after failing an unconditioned haploidentical HCT, and a second after 10 years of ERT. Another patient died of hepatoblastoma discovered after 2 years of ERT, but thought to be present at diagnosis of ADA deficiency. Late deaths due to acute infection appear to be uncommon, but a patient recently died of measles after 10 years of treatment.

Immune dysregulation has been seen in a few patients following commencement of PEG-ADA. Thrombocytosis has been described (Marwaha et al. 2000). Two patients developed refractory immune haemolytic anaemia (Hershfield et al. 1995), one of whom required prolonged immune suppression and died of *candida* sepsis and the other discontinued PEG-ADA and died of complications of a mismatched HSCT. In a significant number of patients (~50%), recovery of immune function also leads to development of antibodies against bovine epitopes of PEG-ADA (Chaffee et al., 1992). In a minority of these individuals an inhibitory antibody directed at the ADA active site develops and results in enhanced ADA clearance. In one case tolerance was induced and in another increased clearance was overcome by increasing the PEG-ADA dose.

Chan et al. 2005 evaluated the immune reconstitution of nine ADA-SCID patients who have received PEG-ADA for 5-12 years (median=9 yrs). The T lymphocyte counts in these patients increased initially but decreased thereafter to low levels. After 5-12 years, the absolute level of T lymphocytes was well below the lower limit of normal. Further impairment of cellular immunity was demonstrated by low levels of CD4+ cells and impaired T cell responses to both mitogens and specific antigens. Malacarne et al. 2005 demonstrated that in five ADA-SCID patients who received PEG-ADA for 5-8 yrs (mean=6.7 yrs), T lymphopaenic also showed decreased levels of TRECs (T cell receptor excision circles—an indicator of thymic activity) in comparison to age matched controls. These patients also showed a decreased response to mitogens and an increased tendency of T cells to apoptosis. In a follow up to the Malacarne et al. 2005 study, Serana et al. 2010 carried out a comparative analysis of patients receiving HSCT (n=5) and PEG-ADA (n=8). This study demonstrated that patients on ERT showed decreased numbers of total lymphocytes/CD3+/CD19+ cells over time, all of which are below the normal range for age. Patients on PEG-ADA in comparison to HSCT recipients also show decreased thymic output and restricted T cell receptor repertoires. The clinical reports of Kaufman et al. 2005 and Husain et al. 2007 documented 2 children, whom after 10 years of PEG-ADA therapy developed an Epstein-Barr virus (EBV)-positive cerebral lymphoma and a Burkitt's lymphoma, respectively. Despite chemotherapy the first patient died 5 months after diagnosis of the tumour and the second patient responded to chemotherapy. In both patients, there was poor recovery of cellular immunity on PEG-ADA, which may have contributed to development of lymphoma. Other patients have also been reported who have developed malignancies after long term PEG-ADA administration.

PEG-ADA results in more systemic delivery of ADA enzyme. As a result it may be thought that PEG-ADA therapy may have a more beneficial effect on the non-immunological consequences of ADA deficiency. However, there is no data to suggest that PEG-ADA treatment improves neurocognitive outcome. In a preliminary study, we have compared patients treated with PEG-ADA alone with those treated by HSCT and although the numbers are small, there is no significant difference between the two groups. Anecdotal evidence from other physicians also suggests that PEG-ADA treated children continue to have behavioural problems.

Therefore, these reports suggest that continued PEG-ADA treatment leads to demonstrable defects of T cell function and impaired thymic activity that may lead eventually to significant clinical infectious complications. An additional concern with long-term ERT beyond 5 years is the emergence of serious complications, described above, including lymphoid and possibly hepatic malignancies, and progression of chronic pulmonary insufficiency. It is also very probable that attempts to treat patients by either HSCT or stem cell gene therapy at this late stage will be unsuccessful or of limited efficacy due to reduced thymic function and increased infective burden (Thrasher et al. 2005). Thus although PEG-ADA may be a short term measure to stabilise children with ADA-SCID, its prolonged use is very likely to be counter-productive.

Previous Retroviral Gene Therapy was Sub-optimal and Raised Safety Concerns

Two structurally identical vectors expressing the human ADA cDNA and distinguishable by the presence of alternative restriction sites in a non-functional region of the viral LTR, were previously used to transduce peripheral blood lymphocytes (PBLs) and T cell depleted bone marrow independently (Bordignon et al. 1995). Thus using restriction digest analysis, it was possible to identify the origin of transduced cells. However, given the low frequency of transduced cells in the circulation the level of total ADA activity in total circulating nucleated cells has remained low (5-18% of normal values). Upon greater follow-up, reports from this study did not show any significant improvement in immunological or metabolic parameters and patients remained on PEG-ADA.

Hoogerbrugge and colleagues performed retroviral mediated gene transfer into 3 children with ADA deficiency in an attempt to effect a cure (Hoogerbrugge et al. 1996). The frequency of peripheral lymphocytes containing the LASN vector as shown by semiquantative PCR, was 1/3000 to 1/100000 18 months after transplantation. At this time point, ADA activity in unselected T cells was measured and found to be barely above the levels found in ADA-SCID patients. The results suggested that due to the small numbers of transduced peripheral blood lymphocytes and the very low level of ADA expression in unselected cells, significant immune reconstitution was unlikely.

Kohn et al. at Children's Hospital Los Angeles (UCLA) attempted withdrawal in one patient from their cord blood gene transfer program. Over two months of observation, there was an overall 25% decrease in the total numbers of T cells and a decrease in the B and NK cell numbers. This prompted investigators to restart PEG-ADA and the patients remained on enzyme replacement to this day (Kohn et al. 1998).

The use of γ-retroviral vector mediated gene therapy has been associated with insertional mutagenesis in 3 different gene therapy trials. This includes 5 patients treated by gene therapy for SCID-X1 (Hacein-Bey-Abina et al. 2008; Howe et al. 2008), 2 patients treated for X-CGD (Stein et al. 2010) and 1 patient treated with Wiskott-Aldrich syndrome (WAS) (Christoph Klein, unpublished data). For ADA-SCID, analysis of γ-retroviral vector integrants has been analysed in a similar way to the studies for the other immunodeficiencies and shows a very similar insertional profile. Integrations are found predominantly in and around the transcriptional start site of genes and insertions have been found in genes associated with cell cycle control, cell signalling and near known oncogenes such as LMO2 (Aiuti et al. 2007). Thus, there is a risk associated with the continued use of conventional γ-retroviral vectors in which transcription of the ADA gene is under the control of the viral LTR. The use of alternative vector systems that can promote improved immune recovery, but with an enhanced safety profile, would be of significant advantage in the furthering the use of gene therapy for ADA-SCID.

The Elongation Factor I-alpha Short Isoform Promoter and Sequences of the Disclosure.

The elongation factor-1 alpha (EF1a) promoter is a constitutive promoter of that can be used to drive constitutive ectopic gene expression in vitro, in vivo and ex vivo. In one embodiment, the EF1a promoter is human. In another embodiment, it is the sequence of SEQ ID NO: 3 or a variant thereof. In a preferred embodiment, the first intron in the naturally occurring EF1a promoter has been deleted resulting in the EF1a promoter short version of SEQ ID NO: 4, or a variant thereof.

As used in the present invention, "variants" may include truncations, deletions, mutations, and/or the addition of sequences not found in the naturally occurring sequence, that do not substantially alter the function of the sequence. Suitable methods readily apparent to the skilled person can be used to assay function. Truncations may refer to removal of about 1, 2, 5, 10, 25, 50, 100, 250, 500, 750, 1000 nucleotides from the 5' and/or 3' end of a sequence. Fragments may lack about 1, 2, 5, 10, 25, 50, 100, 250, 500, 750, 1000 nucleotides from the 5' and/or 3' end of a sequence. In one embodiment, the function of the sequence may be to drive constitutive expression. In another embodiment, the function of the sequence may be to drive tissue-specific expression. The term "tissue-specific expression" refers to expression of a nucleotide sequence and/or polypeptide sequence in a defined tissue that is about 2-fold, 5-fold, 10-fold, 25-fold, 50-fold, 100-fold, 250-fold, 500-fold, 1000-fold, 5000-fold or 10000-fold higher than expression in other tissues. The term "tissue-specific expression" may also refer to expression of a nucleotide sequence and/or polypeptide sequence in a defined tissue, where expression of the nucleotide sequence and/or polypeptide sequence is not detected in any other tissue.

The skilled person would readily be able to determine expression levels of corrected genes (such as ADA), and of other factors (such as the count of CD3, CD4, CD8, naïve T cell, T-cell receptor excision circles (TREC) and immunoglobulin) using techniques know in the art and/or provided herein.

In one embodiment, the sequences of the invention have at least about 60%, 70%, 80%, 90%, 95%, 96%, 97%, 98%, or 99% sequence identity to SEQ ID NOs: 1, 2, 3, 4, 5, 6, 7, 8, 9, 10, 11, 12, 13, 14, 15, 16, 17 and/or 18.

Vectors and Expression Cassettes

In one embodiment, the invention provides a lentiviral construct, or derivative thereof, containing vector and/or expression cassette, in which the transgene is under the transcriptional control of a constitutively acting EFS (elongation factor 1 alpha promoter short version, in which the first intron is deleted).

According to the invention, the vector and/or expression cassette is present at a copy number of 1, 2, 3, 4, 5, 6, 7, 8, 9, 10, 11, 12, 13, 14, 15, 16, 17, 18, 19 or 20 copies per cell. In a one embodiment, the vector and/or expression cassette is present at a copy number of 1, 2, 3, 4, 5, 6, 7, 8, 9 or 10 copies per single cell. In another embodiment, the vector and/or expression cassette is present at an average copy number of 0.5, 1, 2, 3, 4, 5, 6, 7, 8, 9, or 10 copies in a population of cells. In another embodiment, the vector and/or expression cassette is present at an average copy number of from 0.5 to 1, 0.5 to 1.5, 0.5 to 2, 0.5 to 2.5, 0.5 to 3, 0.5 to 4, 0.5 to 5, 0.5 to 6, 0.5 to 7, 0.5 to 8, 0.5 to 9, 0.5 to 10, 1 to 1.5, 1 to 2, 1 to 2.5, 1 to 3, 1 to 4, 1 to 5, 1 to 6, 1 to 7, 1 to 8, 1 to 9, 1 to 10, 1.5 to 2, 1.5 to 2.5, 1.5 to 3, 1.5 to 4, 1.5 to 5, 1.5 to 6, 1.5 to 7, 1.5 to 8, 1.5 to 9, 1.5 to 10, 2 to 2.5, 2 to 3, 2 to 4, 2 to 5, 2 to 6, 2 to 7, 2 to 8, 2 to 9, 2 to 10, 2.5 to 3, 2.5 to 4, 2.5 to 5, 2.5 to 6, 2.5 to 7, 2.5 to 8, 2.5 to 9, 2.5 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 copies per cell. In a preferred embodiment, the vector and/or expression cassette is present at an average copy number of from 0.5 to 2 in said population.

The transgene operably linked to the regulatory region may encode the enzyme adenosine deaminase (ADA) (catalysing reactions classified by EC 3.5.4.4). The transgene encoding the enzyme of the invention may be selected from any of SEQ ID NO: 1, or a variant thereof. The variant may be defined as having at least about 60%, 70%, 80%, 90%, 95%, 96%, 97%, 98%, or 99% sequence identity to any one of SEQ ID NO: 1, based on nucleotide identity over the entire sequence.

Sequence identity may be calculated using any suitable algorithm. For example the PILEUP and BLAST algorithms can be used to calculate identity or line up sequences (such as identifying equivalent or corresponding sequences (typically on their default settings), for example as described in (Altschul 1993; and Altschul et al. 1990). Software for performing BLAST analyses is publicly available through the National Center for Biotechnology Information (www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (Henikoff and Henikoff 1992) alignments (B) of 50, expectation (E) of 10, M=5, N=4, and a comparison of both strands.

The BLAST algorithm performs a statistical analysis of the similarity between two sequences; see e.g., (Karlin and Altschul 1993). One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al. 1984).

The vector and/or expression cassette of the invention may be prepared by standard means known in the art for provision of vectors and/or expression cassettes for gene therapy. Thus, well established public domain transfection and/or transduction, packaging and purification methods can be used to prepare a suitable vector preparations, and suitable viral particles (see below). In one embodiment, the vector may contain the full genome of a naturally occurring lentivirus, or a variant thereof. In an alternative embodiment, the vector may contain a partial genome of a naturally occurring lentivirus, or a variant thereof.

The present invention provides a vector comprising the expression cassette of the invention. In a preferred embodiment, the vector is a lentiviral vector. Lentiviral (and in particular HIV) vectors are well known in the art. These are plasmids that comprise a number of the elements of the lentivirus genome, but do not comprise packaging signals that are required for packaging the RNA produced from the plasmid into virions. In particular, vectors comprise all the elements of the HIV genome required to make replication incompetent viral particles (but without any of the packaging signals). These elements may be present on a single vector. Alternatively, these elements may be split across vectors. HIV vectors may comprise HIV structural proteins, but lack the long terminal repeats (LTRs) necessary for integration into the host cell genome. The vector may also lack the Ψ signal necessary for packaging of viral RNA into virions.

The term "operably linked" refers to a juxtaposition wherein the components described are in a relationship permitting them to function in their intended manner. A control sequence (e.g. an EFS sequence) "operably linked" to a coding sequence (e.g. SEQ ID NO: 1, or a variant thereof) is ligated in such a way that expression of the coding sequence is achieved under conditions compatible with the control sequences.

The vector may additionally comprise polynucleotides encoding additional elements of the HIV-1 genome, such as a polynucleotide encoding HIV-1 Rev, Tat, Vif, Vpr, Vpu and Nef. The vector may comprise all of the HIV viral proteins, except the envelope (Env) protein. The vector may additionally comprise polynucleotides encoding HIV-1 Rev and Tat. This vector may then additionally comprise polynucleotides encoding HIV-1 Vif, Vpr, Vpu and Nef. Vectors such as these are known in the art and are standard HIV vectors. All of the additional components described above, such as HIV-1 Pol, Rev, Tat, Vif, Vpr, Vpu and Nef may be present on the same vector as the construct of the invention, or may instead be present on one or more additional vectors. These components may be arranged in any suitable number of vectors and in any suitable way that results in production of replication incompetent HIV virions once the packaging plasmids are introduced into host cells (see below).

The vector or expression cassette may be of retrovirus, lentivirus, adenovirus or adeno-associated virus origin. In a preferred embodiment, the vector or expression cassette of lentivirus origin may be based on a third generation CCL backbone (system), in which the transgene may be flanked by a LTR and cPPT at the 5' end, and a wPRE sequence and a LTR at the 3' end. Either or both of the LTR sequences may lack the U3 region. The third generation system further improves on the safety of the second generation system. First, the packaging system is split into two plasmids: one encoding Rev and one encoding Gag and Pol. Second, Tat is eliminated from the third generation system through the addition of a chimeric 5' LTR fused to a heterologous promoter on the transfer plasmid. Expression of the transgene from this promoter is no longer dependent on Tat transactivation. The third generation plasmid can be packaged by either a second or third generation packaging system.

Lentiviral Production and Transduction of Host Cell

Lentiviruses are a subclass of retroviruses. They have been adapted as gene delivery vehicles thanks to their ability to integrate into the genome of non-dividing host cells, which is the unique feature of lentiviruses as other retroviruses can infect only dividing host cells. The viral genome in the form of RNA is reverse-transcribed when the virus enters the host cell to produce DNA, which is then inserted into the genome at a random position by the viral integrase enzyme. The integrated genetic material remains in the genome and is passed on to the progeny of the host cell when it divides. For safety reasons, lentiviral vectors usually do not carry the genes required for their replication. To produce a lentivirus, several plasmids are transfected into a so-called packaging cell line, commonly Human Embryonic Kidney (HEK) 293. One or more plasmids, generally referred to as packaging plasmids, encode virion proteins, such as the capsid and the reverse transcriptase. Another plasmid contains the genetic material to be delivered by the vector (i.e. the vector of the present invention). It is transcribed to produce the single-stranded RNA viral genome and is marked by the presence of the w (psi) sequence. This sequence is used to package the genome into the virion.

Packaging plasmids (including vectors and/or expression cassettes of the invention) may be constructed by standard methodology known in the art, for example using standard molecular biology techniques, subcloning using restriction enzymes and/or PCR. Any suitable cell can be used to produce lentiviral stocks containing the vectors and/or expression cassettes of the invention. In general, such cells will be transfected mammalian cells but other cell types, e.g., insect cells, can also be used. In one embodiment, the cell is a mammalian cell. In a preferred embodiment, the cell is a HEK293T cell. In further embodiments, the lentiviral stocks (i.e. viral suspensions) may be produced in HEK293T cells by cotransfection of the packaging plasmids pMD.G2 (VSVG envelope plasmid) and pCMVΔ8.91 (gag-pol plasmid) with the corresponding lentiviral construct (i.e. the expression cassette of the invention), using polyethylenimine (Sigma-Aldrich).

Vector titre can be determined by standard methodology known in the art, for example, by harvesting HEK293T cells transduced with serial dilutions of the viral suspension and the use of flow cytometry and/or quantitative RT-PCT.

In a preferred embodiment, lentiviral stocks are used to transduce the host cell and/or cell populations of the invention by standard methodology known in the art. In one embodiment, the host cell and/or cell population is a mammalian cell. In another embodiment, the host cell and/or cell population is a human cell. In one embodiment, the host cell and/or cell population is a bone marrow cell. In one embodiment, the host cell and/or cell population is a haematopoietic stem cell (HSC) and/or a haematopoietic progenitor cell such as a peripheral blood stem cell (PBSC). In one embodiment, the host cell and/or cell population expresses CD34. In one embodiment, the host cell and/or cell population is derived from bone marrow. In one embodiment, the host cell and/or cell population is a common myeloid progenitor. In one embodiment, the host cell and/or cell population is a granulocyte-macrophage progenitor. In one embodiment, the host cell and/or cell population is a megakaryocyte-erythroid progenitor cell. In one embodiment, the host cell and/or cell population is a macrophage.

The host cell and/or cell populations may be used directly after viral transduction. Alternatively, the cell and/or cell populations may be sub-cultured after viral transduction but before use in therapy. The host cell and/or cell populations may be sub-cultured according to standard techniques well known in the art, appropriate to the cell type. For example, some or all of the cells that have been newly transduced and/or previously cultured, may be transferred into fresh growth medium for culturing. Sub-culturing can be used to expand and/or select virally transduced cells.

In one embodiment, the vector and/or expression cassette design is used to drive transgene expression in a mammalian cell. In another embodiment, the vector and/or expression cassette design is used to drive transgene expression in a human cell. In another embodiment, the vector and/or expression cassette design is used to drive transgene expression in all haematopoietic lineages. In another embodiment, this vector and/or expression cassette design is used to drive transgene expression in HSCs and/or haematopoietic progenitor cells and/or a population of HSCs and/or haematopoietic progenitor cells. In another embodiment, this vector and/or expression cassette design is used to drive transgene expression in a common myeloid progenitor. In another embodiment, this vector and/or expression cassette design is used to drive transgene expression in a granulocyte-macrophage progenitor. In another embodiment, this vector and/or expression cassette design is used to drive transgene expression in a megakaryocyte-erythroid progenitor cell. In another embodiment, this vector and/or expression cassette design is used to drive transgene expression in a macrophage. In another embodiment, this vector and/or expression cassette design is used to drive transgene expression in erythrocytes. In another embodiment, this vector and/or expression cassette design is used to drive transgene expression in any cell derived from a HSC. A cell derived from a HSC would be apparent to the skilled person.

In one embodiment, a method is provided to make the host cell and/or cell population of the invention by isolating by standard techniques known to the person skilled in the art a cell or cell population from a first organism. For example, the cells may be isolated from peripheral blood and/or by aspiration of the bone marrow. In particular, red blood cells (RBCs), white blood cells (WBCs) and/or peripheral blood mononuclear cells (PBMCs) may be isolated. Cells may be isolated using standard techniques known in the art and/or disclosed herein. For example, WBCs can be isolated by leukapheresis.

In a further embodiment, a vector and/or expression cassette of comprising the regulatory region of the invention (i.e. the elongation factor 1-alpha short isoform (EFS) promoter, which may regulate the expression of a transgene operably linked to the regulatory region) may be introduced into the cell or cell population. In a preferred embodiment, the vector is introduced into the host cell or cell population by viral transduction (see above). In a further embodiment, the isolated cell and/or cell population may be cultured, for example ex vivo using standard techniques. Suitable culture conditions would be apparent to the person skilled in the art. Cytokines selected from TPO, SCF, IL-3 and/or Flt-3 may be used to supplement culture media.

In further embodiments, the isolated and/or cultured cell and/or cell population may be introduced into the first organism, a second organism that is related to the first organism, a second organism that is a tissue type match for the first organism, and/or a second organism with a different genetic background to the first organism. The isolated and/or cultured cell and/or cell population may be introduced into the first or second organism by direct injection into the blood and/or into the bone marrow.

As used here, a "cell population" refers to any group of two or more cells. A cell population may refer to about 10; 100; 500; 1000; 5000; 10,000; 50,000; 100,000; 500,000; 1,000,000; 5,000,000; 10,000,000; 50,000,000; 100,000,000; 500,000,000; or 1,000,000,000 cells. In another embodiment, a cell population may refer to about 100 or more cells. In another embodiment, individual cells in the cell population may be functionally distinct from each other, functionally similar to each other, and/or functionally identical to each other. Cells in the cell population may be from different lineages. In one preferred embodiment, the cells in the cell populations are from the same and/or similar lineages. In another embodiment, cells in the cell populations are from cells of the haematopoietic lineage. In another embodiment, cells in the cell population are from HSCs and/or haematopoietic progenitor cells. In another embodiment, cells in the cell population are from common myeloid progenitors, granulocyte-macrophage progenitors, megakaryocyte-erythroid progenitors, macrophages and/or erythrocytes. Cell populations may be derived from a single cell and/or population of cells, cultured ex vivo.

The cell population may be cryopreserved, either directly after viral transduction and/or after sub-culture. Cryopreservation is a process where cells, whole tissues, or any other substances susceptible to damage caused by chemical reactivity or time are preserved by cooling to sub-zero temperatures (i.e. less than 0° C.). At such temperatures, any enzymatic or chemical activity which might cause damage to the material in question is effectively stopped. Cryopreservation methods seek to reach low temperatures without causing additional damage caused by the formation of ice during freezing. Techniques for cryopreservation would be well-known to the person skilled in the art.

Methods of Therapy and Medical Uses

The promoters, regulatory regions, vectors, host cell, cell populations and/or expression cassettes of the invention may be used to treat ADA-SCID. Treatment may encompass correction of one or more metabolic and/or immunological defects associated with ADA-SCID. Treatment may encompass correction of expression of ADA enzyme levels.

ADA enzyme levels may be corrected to wild type or above wild type levels. ADA activity may be corrected to between 50 and 10000 nmol/mg haemoglobin/hour in RBCs. ADA activity may be corrected to between 1000 and 3500 enzyme units per VCN. Correction of ADA enzyme levels and/or enzyme activity in patients treated with the LV construct of the invention may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 100, 125, 150, 175 or 200 times higher than in patient treated with the same average copy number of ADA containing gRV constructs.

Immunological defects that are corrected may include the number of neutrophils, platelets, lymphocytes, CD3 positive cells, CD4 positive cells and/or CD8 positive cells. The concentration of neutrophils in corrected patients may be 500 to 10,000 cells per mm$^2$. The concentration of platelets in corrected patients may be 500 to 1,000,000 cells per mm$^2$. The concentration of lymphocytes in corrected patients may be 500 to 10,000 cells per mm$^2$. The concentration of CD3 positive cells in corrected patients may be 50 to 5,000 cells per mm$^2$. The concentration of CD4 positive cells in corrected patients may be 50 to 2,500 cells per mm$^2$. The concentration of CD8 positive cells in corrected patients may be 50 to 5,000 cells per mm$^2$.

Treatment occurs through the sustained or transient release of enzyme from the host cell and/or a cell derived from the host cell. In one embodiment, release of the enzyme may be into the circulation. In another embodiment, release of the enzyme may be into a specific group of tissues and/or organs. In another embodiment, release of the enzyme may be into a specific tissue and/or organ. In one embodiment, the enzyme may be targeted to red blood cells, PBMCs, the central nervous system (CNS), heart, face, mouth, eye, bone, liver, spleen and/or lung. In one embodiment, treatment results in an about 2 log, 3 log, 4 log or 5 log increase in enzyme activity in the plasma and/or different organs and/or tissues. In one preferred embodiment, the activity of ADA is increased systemically.

Thus, the invention provides a means whereby the various phenotypes associated with ADA-SCID can be correct, treated, arrested, palliated and/or prevented. Correction can refer to partial, total correction and/or hyper-correction. Correction may be achieved after about 10 days, 20 days, 30 days, 40 days, 50 days, 60 days, 70 days, 80 days, 90 days, 100 days, 125 days, 150 days, 175 days, 200 days, 250 days, 300 days, 1 year, 1.5 years, 2 years or 3 years. In one embodiment, effect of correcting, treating, arresting, palliating and/or preventing a phenotype can be transient. In another embodiment, effect of correcting, treating, arresting, palliating and/or preventing a phenotype can be sustained. Correction may be sustained for at least 1 month post-administration, at least 3 months post-administration, at least 6 months post-administration, at least 12 months post-administration, at least 24 months post-administration, at least 36 months post-administration, at least 48 months post-administration, at least 50 months post-administration, or at least 62 months post-administration.

In one embodiment, a method is provided to make the host cell and/or cell population of the invention for use in a method of preventing or treating ADA-SCID. In another embodiment, a method is provided to make the host cell and/or cell population of the invention in the manufacture of a medicament for the treatment and/or prevention of ADA-SCID. In another embodiment the host cell, population, cell for use, cell population for use, method or use of the invention, treat the disease ADA-SCID when the transgene of the invention encodes ADA.

The host cell and/or cell population of the invention may be made by isolating by standard techniques known to the person skilled in the art a cell or cell population from a first organism. For example, the cells may be isolated from peripheral blood and/or by aspiration of the bone marrow. In a further embodiment, a vector and/or expression cassette of comprising the regulatory region of the invention, in which the EFS promoter, regulates the expression of a transgene operably linked to the regulatory region, may be introduced into the cell or cell population. In a preferred embodiment, the vector is introduced into the host cell or cell population by viral transduction (see above). In a further embodiment, the isolated cell and/or cell population may be cultured, for example ex vivo using standard techniques. Suitable culture conditions would be apparent to the person skilled in the art. Cytokines selected from TPO, SCF, IL-3 and/or Flt-3 may be used to supplement culture media.

In further embodiments, the isolated and/or cultured cell and/or cell population may be introduced into the first organism, a second organism that is related to the first organism, a second organism that is a tissue type match for the first organism, and/or a second organism with a different genetic background to the first organism. The isolated and/or cultured cell and/or cell population may be introduced into the first or second organism by direct injection into the blood and/or into the bone marrow.

The invention provides a pharmaceutical composition comprising the host cell and/or cell population of the invention and a pharmaceutically acceptable carrier for use in a method of preventing or treating ADA-SCID.

The invention also provides a vector and/or expression cassette for use in a method of preventing and/or treating ADA-SCID.

The invention also provides the use of a host cell and/or cell population of the invention in the manufacture of a medicament for the treatment and/or prevention of ADA-SCID.

The invention also provides a method of treating or preventing ADA-SCID in a patient in need thereof comprising administering a therapeutically effective amount of a host cell and/or cell population of the invention to the patient.

The invention also provides a method of treating or preventing ADA-SCID in a patient in need thereof, comprising administering a therapeutically effective amount of a cell and/or cell population of the invention to the patient by direct injection into the blood and/or bone marrow. Accordingly, ADA-SCID is thereby treated or prevented in said patient.

Additionally, the invention provides the use of the cell and/or cell population of the invention in the manufacture of a medicament for treating or preventing ADA-SCID by direct injection into the blood and/or bone marrow.

The invention also provides host cells and/or cell populations for use wherein said host cells and/or cell populations are administered directly into the blood and/or bone marrow.

In all these embodiments, the host cells and/or cell populations of the invention may be administered in order to prevent the onset of one or more symptoms of ADA-SCID. The patient may be asymptomatic. The subject may have a predisposition to the disease. The method or use may comprise a step of identifying whether or not a subject is at risk of developing, or has, ADA-SCID. A prophylactically effective amount of the cells and/or cell populations is administered to such a subject. A prophylactically effective amount is an amount which prevents the onset of one or more symptoms of the disease.

Alternatively, the host cells and/or cell populations may be administered once the symptoms of the disease have appeared in a subject, i.e., to cure existing symptoms of the disease. A therapeutically effective amount is an amount which is effective to ameliorate one or more symptoms of the disease.

The subject may be male or female. The subject is preferably identified as being at risk of, or having, ADA-SCID.

The dose of the host cells and/or cell populations of the invention may be determined according to various parameters, especially according to the age, weight and condition of the patient to be treated; the route of administration; and the required regimen. A physician will be able to determine the required route of administration and dosage for any particular patient. The dose may be provided as a single dose, but may be repeated or in cases where vector may not have targeted the correct region and/or tissue (such as surgical complication). The treatment is preferably a single permanent treatment, but repeat injections, for example in future years and/or with different lentiviral serotypes may be considered.

Pharmaceutical Compositions and Dosages

The host cell and/or cell population of the invention can be formulated into pharmaceutical compositions. These compositions may comprise, in addition to the host cell and/or cell population, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, for example direct injection into the blood and/or bone marrow.

The pharmaceutical composition is typically in liquid form. Liquid pharmaceutical compositions generally include buffered liquid carriers. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity, and stability. Those of relevant skill in the art are able to prepare suitable solutions using, for example, isotonic vehicles such as sodium chloride injection, Ringer's injection, lactated Ringer's injection, Hartmann's solution. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Dosages and dosage regimes can be determined within the normal skill of the medical practitioner responsible for administration of the composition.

Combination Therapies

The promoters, expression cassettes, vectors, host cells, cell populations and/or pharmaceutical compositions can be used in combination with any other therapy for the treatment or prevention of ADA-SCID. The promoters, expression cassettes, vectors, host cells, cell populations and/or pharmaceutical compositions can be used in combination with any other targeted and non-targeted delivery mechanism, such as tagged enzymes and exosomes respectively.

Kits

The promoters, expression cassettes, vectors, host cells, cell populations and/or pharmaceutical compositions can be packaged into a kit. Cells of the kit may be cryopreserved according to standard methods known in the art. The kit may comprise a pharmaceutically acceptable excipient. The pharmaceutically acceptable excipient may be saline and 2% human albumin solution. The kit may be contained in a transfer bag.

Other Applications

The vector, expression cassette, lentiviral particle, host cell, and/or cell population of the invention may be used in vitro, for example, for molecular biology research purposes. In particular, the virus particles may be used to deliver a transgene (either in vitro, in vivo, or ex vivo). Transgenes can include genes coding for therapeutic proteins (such as SEQ ID NO: 1), RNAs and also nucleic acids involved in gene silencing, such as siRNAs or antisense RNAs. Virus particles of the invention may be used in gene silencing. In this case, the virus particles may be used to deliver a siRNA (in the form of a shRNA). Lentiviruses can also been used to transduce embryonic stem cells and to introduce transgenes into early embryos in order to generate transgenic animals. Lentiviruses have also been used to knock down targeted genes in vivo. Other applications of lentiviruses include immune modulation, cellular reprogramming, and in vivo imaging.

EXAMPLES

Materials and Methods

Experimental Animals

All animals were handled in laminar flow hoods and housed in microinsulator cages in pathogen-free colonies. Animal procedures and housing were in accordance with Home Office animal welfare legislation at University College London (UCL) in the United Kingdom, and in accordance with the Animal Research Committee and Division of Laboratory Animal Medicine and the National Institutes of Health guidelines at University of California, Los Angeles (UCLA) in the United States. ADA mice were as described previously (Blackburn et al. 1998). ADA+/+ and ADA−/− mice were generated by intercrossing ADA+/− females with ADA+/− males. Progeny were genotyped by polymerase chain reaction (PCR) assay (jaxmice.jax.org). ADA−/− mice were maintained by weekly intraperitoneal injection (i.p.) of PEG-ADA at a dose of 1,000 units/kg until transplanted and then remained on ERT for 1 month after transplant. NSG were as described previously (Shultz et al. 2005). C57BL/6 mice were purchased from Harlan Laboratories (UK) and from Jackson Laboratory.

Codon Optimisation

A human codon optimised ADA sequence were obtained by using GeneScript OptimumGene™ algorithm. This generates gene sequences with the highest possible level of expression by taking into account the variety of factors that influence gene expression level, i.e., changing codon usage bias or modifying GC content and secondary structures that would interfere with translational efficacy and mRNA stability.

Viral Vector Construction, Production and Titer Determination

A codon-optimized human ADA cDNA sequence linked with an EFS fragment was inserted into ClaI/SalI sites in the pCCLsincpptW1.6hWasp-WPRE backbone. The LV MND-ADA was constructed by inserted a blunted Hind III human ADA cDNA fragment into the SmaI site of pCCLc-MNDU3-X2 backbone, which contains the retroviral MND LTR U3 region driving expression of human ADAcDNA. The SFada/W vector (Gaspar et al. 2006) was amended to contain a wild-type human ADA cDNA controlled by the gRV SFFV LTR. The gRV MNDADA vector contained the human ADA cDNA under the control of the MND LTR. The LV EFS GFP vector was cloned with a HinclllBamHl fragment containing EFS promoter into the P'HR-cppt-SEW (LV SF GFP) vector. The gRV SF91 GFP vector was as described in (Schambach et al. 2000).

The LVs were packaged in HEK293T cells by triple transfection of the packaging plasmids pMD.G2 (VSVG envelope plasmid) and pCMVΔ8.91 (gag-pol plasmid) with the corresponding viral construct, using polyethylenimine (Sigma-Aldrich), with sodium butyrate stimulation for the first 24 hours (Sigma Aldrich). Virus supernatant was collected 48-72 hours after transfection, and viral particles were concentrated by ultracentrifugation or tangential flow. Evaluation of LV EFS ADA in the NSG mice was performed with vector produced in two batches produced under Good Manufacturing Practice at the Indiana University Vector Production Facility. The LV vector DNA titer was determined on murine SC-1 fibroblasts and human HT29 colon carcinoma cells which were harvested at 72 hours after transduction and DNA was extracted with DNeasy Blood and Tissue kit (Qiagen, UK) following the manufacturer's instructions. qPCRs were performed with primers and probe to detect the HIV Ψ region specific for the packaging region of LVs (sense primer 5'-acctgaaagcgaaagggaaac-3' (SEQ ID NO: 5), antisense primer 5'-cgcacccatctctctcctct-3' (SEQ ID NO: 6), and probe FAM-agctctctcgacgcaggactcggc-TAMRA (SEQ ID NO: 7)).

The gRVSFada/W and gRV SF91 GFP vectors were packaged in HEK293T cells by triple transfection of the packaging plasmids pEco (murine ecotropic envelope; Clontech, Europe) and M13 (MuLV gag-pol expression plasmid) with corresponding construct using a calcium phosphate transfection kit (CAPHOS, Sigma) under manufacturer's instructions. Supernatants were collected 48-72 hours after transfection and filtered through a 0.45 μm filter. The vector titre was determined on murine SC-1 fibroblasts by spin-oculation with serial dilutions of supernatant for 40 minutes at 1,000×g, 4° C. in the presence of 8 μm/ml polybrene. Viral transduced cells were harvested after 72 hours and DNA extracted with DNeasy Blood and Tissue kit (Qiagen) following the manufacturer's instructions. qPCR were performed with primers and probe to detect a common region in wPRE fragment in the gRV GFP vectors or viral integrations, Titin for murine cells or b-actin for human cells as DNA-loading control. The gRV SF91 GFP vector was also packaged from a stable clone of the GP+E86 ecotropic packaging cell line as a positive control for the in vitro insertional mutagenesis (IVIM) assay at UCLA. Titre was determined on HT29 cells and DNA was extracted with DNeasy Blood and Tissue kit (Qiagen) following the manufacturer's instructions. qPCR were performed with primers and probe to detect GFP (sense primer is 5'-ctgctgcccga-caacca-3' (SEQ ID NO: 8), antisense primer is 5'-gaactcca-gcaggaccatgtg-3' (SEQ ID NO: 9), and probe 5'-FAM-ccctgagcaaagacccaacgaga-Tamra-3' SEQ ID NO: 10)). The gRV-MND-ADA vector supernatant was produced from a stable clone of the PG13 GALV-packaging line.

All experiments were performed with thawed vector stocks of known titers (LV: 0.6-10×10$^9$ transducing units (TU)/ml; gRVSFada/W and gRV SF91 GFP: 1-10×10$^6$ TU/ml); gRV MND-ADA: 1.8×10$^5$ TU/ml).

Isolation, Enrichment, Transduction, and Transplantation of Murine ADA−/− BM Lin− HSCs and Human HSCs in Pre-clinical Models Murine BM cells were harvested by flushing tibias, femora, and pelvis of age-matched male donor ADA+/+ or ADA−/− mice. BM lineage negative (Lin−) cells were enriched with the BDIMag Mouse Hematopoietic Progenitor Cell Enrichment Set (BD Biosciences, San Jose, Calif.) and preactivated in Stemspan serum-free expansion medium (SFEM) (StemCell Technologies, UK) in the presence of 100 ng/ml of murine stem cell factor, human Flt3 ligand (Flt3-L), murine thrombopoietin (mTPO), and 20 ng/ml of murine interleukin-3 (IL-3).

After 24-hour preactivation, the LV EFS ADA or LV EFS GFP vectors were directly added to cells at a MOI of 20 and incubated for 16-24 hours. For SFada/W gRV vector, the cells were preactivated for 72 hours and then underwent a two-round transduction protocol with a 6-hour gap. In each round, viral particles corresponding to a MOI of 20 were spinoculated for 40 minutes at 1,000×g, 4° C. onto a retronectin-coated plate. The cells were added into virus-coated plates after removal of supernatant. After 24 hours after transduction, all cells were injected via the tail vein into 4-12 weeks old sub-lethally irradiated (5 Gy, split dose) female ADA−/− recipients at a dose of 5×10$^5$ cells/mouse. In ADA−/− WT group, isolated ADA+/+ BM Lin− cells were injected instead. All transplants were maintained on ERT with weekly i.p. injection of PEG-ADA at 1,000 units/kg for 4 weeks post-transplantation. A group of age-matched ADA−/− mice under continuous PEG-ADA injection were used as a positive control. The negative control group of untreated ADA−/− mice were euthanized at day 18-20 after birth.

Human CD34+ cells (HSC) were isolated from anonymous waste normal human cord blood and bone marrow, which has been deemed exempt from IRB review as not constituting human subjects research, and from ADA-deficient SCID bone marrow, under approved UCLA IRB #10-001399 with informed consent provided by parents of the subjects. Normal human adult bone marrow samples (100 ml/donor) were also purchased from AllCells, LLC (Emeryville, Calif.). For human CD34+ cell isolation, human cord blood or human bone marrow was diluted 1:2 with Dulbecco's phosphate-buffered saline and distributed into 50 ml conical tubes containing 15 ml of Ficoll-Paque PLUS (GE HealthCare Life Sciences, Piscataway, N.J.) and centrifuged (no brake) at 400×g for 30 minutes at room temperature. The mononuclear cells (the buffy coat) were harvested and CD34+ cells were isolated by immunomagnetic separation with the Miltenyi MACS CD34+ Cell Isolation Kit (Miltenyi Biotech, Auburn, Calif.). Cells were counted and either transduced as freshly isolated CD34+ cells or cryopreserved (freezing medium: 90% serum and 10% DMSO) and then transduced after thawing. Transduction. Human CD34+ cells (100,000 or 500,000 cell/ml), were plated on Retronectin coated six-well plates (20 µg/ml; Takara/Clontech, Mountain View, Calif.) and prestimulated for 24 hours in X-Vivo 15 serum-free medium (Biowhittaker/Lonza, Walkersville, Md.) supplemented with L-glutamine (2 mmol/1), human TPO (100 ng/ml), human stem cell factor (300 ng/ml), human Flt3 ligand (Flt3-L; 300 ng/ml), and with or without IL-3 (20 ng/ml) (all cytokines from BioLegend, San Diego, Calif.). The cells were transduced with the EFS-ADA LV at a concentration of $3.0 \times 10^7$ TU/ml (except where indicated otherwise) for 18-20 hours at 37° C. with 5% $CO_2$. gRV transductions were done following 2 days of prestimulation, as above, by adding unconcentrated gRV-MND-ADA vector supernatant to cells daily×3 days.

Irradiated (150 cGy) neonatal NSG mice were transplanted with 50,000 to 100,000 transduced (LV EFS ADA) or nontransduced (mock) human CD34+ cells by intravenous injection into the superficial temporal (facial) vein between postnatal day 1 and 3. The mice were euthanized 4 months after transplant, and the thymus, spleen, and bone marrow were harvested and analyzed for the presence of human cells (engraftment) and vector (VCN and expression). Bone marrow cells were isolated from each primary recipient, red blood cells were lysed, and $1 \times 10^7$ nucleated cells were serially transplanted into a conditioned secondary recipient (250 cGy).

Analysis In Vitro of Transduced Human HSC

For myeloid culture, immediately following the transduction period, the LV-transduced and mock-transduced cultures were maintained in Iscove's modified Dulbecco's medium supplemented with 20% fetal calf serum (Omega Scientific, Tarzana, Calif.), 0.5% human serum albumin (AlbuRx; CSL Behring LLC, Kankakee, Ill.), L-glutamine (2 mmol/1), penicillin/streptomycin (100 U/ml), human IL-3 (5 ng/ml), IL-6 (10 ng/ml), and stem cell factor (25 ng/ml) (all cytokines from BioLegend). On day 7, one half of the medium was exchanged for fresh medium with freshly diluted cytokines. On day 14 of post-transduction culture, $1 \times 10^6$ cells were harvested for DNA extraction and $0.5 \times 10^6$ cells were harvested for ADA enzyme activity assay. DNA was purified using the DNAeasy kit (Qiagen, Valencia, Calif.) and ADA enzyme activity was determined with the ADA enzyme assay by Diazyme (San Diego, Calif.).

For colony assays, samples of the transduced CD34+ cells were also plated for progenitor assays (CFU) (two to three dilutions in duplicate) in semisolid methylcellulose medium supplemented with cytokines (Stem Cell Technologies, Vancouver, BC, Canada). Between days 11 and 14, colonies were counted and characterized by progenitor type. Single colonies were aspirated from the methylcellulose and placed into a microcentrifuge tube containing 1 ml of Dulbecco's phosphate-buffered saline for 1 hour at 37° C. The tubes were centrifuged for 10 minutes at 400×g and cell pellets stored at −20° C. for later DNA extraction and VCN analysis. Colony DNA was purified with a single phenol/chloroform extraction, precipitated in the presence of glycogen (20 mg/ml, Roche Diagnostics, Mannheim, Germany; Invitrogen, Carlsbad, Calif.) and resuspended in 25 µl of Tris-EDTA (pH 7.4). To determine CFU VCN, 5 µl of the extracted DNA were analyzed by Multiplex qPCR using primers/probe for the human ADA cDNA and the human SDC4 gene (to normalize for DNA concentration) and compared to the EFS-ADA copy number standard described above.

Flow Cytometry Analysis for Immunophenotype and Engraftment

From ADA mice, the percentage of T cells (CD3+, CD4+, and CD8+), B cells (B220+), myeloid cells (GR-1+), and natural killer (NK1.1+) cells were analysed in the peripheral blood (PB), thymus, spleen, or bone marrow of ADA mice. For flow cytometry, $2 \times 10^5$ cells from red cell lysed PB, lymphoid organs, or bone marrow were preincubated for 15 minutes at room temperature with murine serum followed by staining for 30 minutes at 4° C. with anti-mouse antibodies all from BD Pharmingen including: PE-CD3, PE Cy7-CD4, APC-CD8a, APC-B220, APC-GR-1, and APC-NK1.1. After washing, cells were analysed using CyAn ADP Analyzer (Beckman Coulter) and Summit software. In transplanted NSG mice, the level of engraftment and the immunophenotype of human cells was determined by flow cytometry (FACS) immunostaining with anti-human antibodies from BD Biosciences and flow cytometry on a BD LSRII instrument with DIVA (BD Biosciences) Software. Percent engraftment was determined on bone marrow cell suspensions (flushed from femur and tibia bones) immunostained with anti-human CD45 (PerCp or APC). The percentage of engrafted human cell lineages was determined on tissue cell suspensions immunostained as follows: thymus-anti-human CD4-PE, anti-human CD8-APC; spleen-anti-human CD3-PE, anti-human CD19-APC; and bone marrow anti-human CD11b-APC, anti-human gran-1-PE.

Quantification by qPCR for VCN and Donor Cell Engraftment

All amplification reactions were performed in the 7,500 Fast Real-Time PCR System (Applied Biosystems/Life Technologies (LT) UK and USA) under default conditions and analyzed using Manufacturer's software. For ADA mice, genomic DNA was extracted from murine tissues and PB by DNeasy Blood & Tissue Kit (Qiagen). VCN in total cells from different organs was detected by qPCR using primers amplifying sequences in wPRE or Titin. Known copies of wPRE from LV-transduced MEL cells serially diluted into irrelevant genomic DNA were used to set up a standard curve. The frequency of male donor cells was determined by qPCR for the Y chromosome using primers described previously. These data were calculated using a standard curve of serially diluted male cells into female cells from ADA mice. For NSG mice, genomic DNA was extracted from murine spleen and bone marrow with DNeasy Blood & Tissue Kit (Qiagen). From smaller thymic tissue samples ($0.5-1 \times 10^5$ cells), DNA was extracted with phenol chloroform extraction as described previously. The human ADA gene in both gRV (not codon optimized) and LV vectors (codon optimized) was amplified using primers and probe that span exon 6 and 7 of the human ADA gene (sense primer 5'-ggtccatcctgtgctgcat-3' (SEQ ID NO: 11), anti-sense primer 5'-cggtctgctgctggtacttctt-3' (SEQ ID NO: 12), and probe 5'-FAM-ccagcccaactggtcccccaag-tamra-3' (SEQ IS NO: 15)). VCN was normalized by qPCR of the human syndecan 4 gene (SDC4) (sense primer 5'-cagggtctgggagccaagt-3' (SEQ ID NO: 14), anti-sense primer 5'-gcacagtgctggacattgaca-3' (SEQ ID NO: 15), and probe 5-HEX-cccaccgaacccaagaaactagaggagaat-Iowa Black FQ (SEQ ID NO: 16)). DNA extracted from a cellular clone containing four copies of integrated LV EFS ADA vector was serially diluted into equally concentrated DNA from non-transduced cells to make the standard curve used to quantify the VCN per cell.

ADA and SAHH Activity Assay

For ADA mice, ADA activity assay was performed with cell lysates from transplanted ADA−/− and controls prepared in 200-500 µl of $H_2O$ per sample. 12.5 µl of the lysate was incubated with the reaction mix containing 50 µl of phosphate-buffered saline (Invitrogen/Life technologies), 37.5 µl of 10 mmol/l adenosine (Sigma-Aldrich) for 0 or 20 minutes in 37° C. water bath. Then, the reaction was stopped by adding 12.5 µl of 40% trichloroacetic acid (Sigma-Aldrich). The precipitations were spun down, and trichloroacetic acid in the supernatant was extracted by $H_2O$-saturated diethyl ether. S-adenosyl homocysteine hydrolase (SAHH) activity assay, 100 µl of master mix (50 µl of 62.5 mmol/l $KH_2PO_4$, 5 µl of 20 mmol/l DTT, 10 µl of 10 mmol/l EDTA, 20 µl of 37.5 mmol/l homocysteine, and 15 µl of $H_2O$) was added into each tube with 10 µl of 150 µmol/l deoxycoformycin (Pentostatin; TOCRIS Bioscience, UK) and 25 µl of lysate. The tubes were preincubated in a 37° C. water bath for 5 minutes. To start the reaction, 10 µl of 6.5 mmol/l adenosine was added into the mixture and incubated for 0 or 60 minutes at 37° C. until stopped by adding in 25 µl of 40% trichloroacetic acid. The precipitations were spun down and trichloroacetic acid in the supernatant was extracted by $H_2O$-saturated diethyl ether. The level of substrates in ADA or SAHH activity assays was measured on anion-pair HPLC Waters 2795 system with PDA detection (Waters, Milford, Mass.). The final ADA activity was normalized with protein concentration or hemoglobin concentration.

For NSG mice, ADA enzyme activity was measured in human cells isolated from total tissue cell suspensions of spleen and bone marrow using the anti-human CD45 Miltenyi MACs Cell Separation System (Miltenyi Biotech, Auburn, Calif.). Mice transplanted with mock-transduced cells were also used to determine a baseline of ADA activity in the engrafted human cells, as the CD34+ cells from ADA replete cord blood or bone marrow will have background ADA expression. A colorimetric ADA enzyme assay kit (Diazyme Laboratories, Poway, Calif.) was used to determine the amount of ADA enzyme activity in the primary human CD34+ cells from in vitro culture and from human cells isolated from NSG mice. Cells (0.5×10$^6$ cells) were centrifuged at 400×g for 5 minutes and a dry pellet was frozen at −80° C. for batch assays. The kit uses a calibrator that is serially diluted to make a standard curve for quantification. The catalytic conversion of adenosine by ADA enzyme is ultimately read-out by the conversion of hypoxanthine to uric acid and hydrogen peroxide that reacts with N-Ethyl-N-(2-hydroxy-3-sulfopropyl)-3-methylaniline and 4-aminoantipyrine in the presence of peroxidase to generate a quinone dye, which is detected spectrophotometrically at 550 nm.

For Western blot analysis, the cell lysate was prepared with 1×10$^6$ cells in RIPA lysis buffer by standard method and subjected to sodium dodecyl sulfate-polyacrylamide gel electrophoresis. The proteins were transferred to nitrocellulose membrane (Sigma-Aldrich). Anti-ADA antibody was provided by Dr. M. Hershfield (Duke University, Durham, N.C.). Anti-GAPDH monoclonal antibody was obtained from Santa Cruz Biotechnology (Santa Cruz, Germany).

For histological analysis, tissues and organs of ADA mice including lung, liver, heart, and kidney were harvested and examined histologically. Tissues and organs were rinsed in phosphate-buffered saline and then fixed in 10% formalin for more than 24 hours at 4° C. Then, tissues were dehydrated, cleared, and embedded in paraffin following routine procedures. Sections of 4 µm in size were cut and stained with hematoxylin and eosin and mounted using standard protocols for histopathological analysis under an optical microscope (Olympus BX50).

For the in vitro immortalization assay (IVIM-WST1) assay, BM Lin− cells of C57BL6 mice were isolated with the BDIMag Mouse Hematopoietic Progenitor Cell Enrichment Set (BD Biosciences, 558451) and preactivated in Stemspan serum-free expansion medium (StemCell Technologies) containing 50 ng/ml murine stem cell factor, 100 ng/ml hFlt-3 ligand, 100 ng/ml hIL-11, and 10 ng/ml mIL-3 (PeproTech, UK) at a density of 5×10$^5$ cells/ml. 1×10$^5$ cells were transduced on day 4 and 5 at an MOI of 20 for each viral vector. LVs were directly added to cells. gRVs were preloaded on retronectin-coated plate (TaKaRa, Japan) by spinoculation for 40 minutes at 4° C. and then incubated with cells for 16-24 hours. After two-round transductions, cells were expanded as bulk populations for 2 weeks in Iscove's modified Dulbecco's medium containing the same cytokine cocktail as above with 10% fetal calf serum. DNA samples were taken at day 9 for vector copy analyses by qPCR. Two weeks later, cells were plated into 96-well plates at a density of 100 cells per well and incubated at 37° C. for another 14 days. Subsequently, half of cells from each well were incubated with 10 µl of WST-1 (Roche, Europe) for 4 hours at 37° C. The absorbance was measured at 450 nm in a FLUOstar Optima luminometer (BMG Labtech, Ortepathnberg, Germany). The highest absorbance from mock-transduced clones was set as the baseline above which all clones were counted as positive ones. The frequency of replating cells was calculated using L-Calc software (Stem Cell Technologies) and normalized with VCN. Selected clones were expanded for further characterization.

EFS-ADA Vector Production for the Phase I/II Clinical Trial

The EF1αS-ADA vector (see FIGS. 1A and 1B) is a GMP grade recombinant lentiviral vector for ex vivo gene therapy. This state-of-the-art SIN lentiviral vector lacks viral coding sequences that may give rise to the formation of replication competent lentivirus or immunogenic peptides and is also devoid of all lentiviral enhancer-promoter sequences that are known be involved in insertional mutagenesis by retroviruses and derived vectors. The internal promoter was chosen from a human gene that shows expression in hematopoietic stem/progenitor cells as well as TB- and NK cells, as required for the correction of ADA-SCID In its plasmid DNA configuration the EF1αS-ADA lentiviral vector contains the following vector modules: (1) the pCCL self-inactivating ("SIN") lentiviral vector is derived from HIV-1. (2) All open-reading frames of HIV-1 genes have been deleted from the vector, leaving only 2007 bp (20.65% of HIV-1 genome) from HIV-1 consisting of: the "SIN" LTRs, the packaging sequences (Ψ), the rev-responsive element and the central polypurine tract. (3) The 400 bp SIN deletion from the LTRs removes the promoter and enhancer (from −418 to −18 relative to the U3/R border), leaving only 53 bp with the attachment sequences for chromosomal integration and the polyadenylation signal. (4) A "short" promoter fragment (239 bp) from the human EF1α gene, lacking intronic or enhancer sequences (EFS), drives transcription of a normal human ADA cDNA. (5) The transcriptionally disabled wPRE is downstream. The wPRE sequence used here is devoid of the hepadnaviral X-protein open reading frame and contains a point mutation that destroys the largest residual open reading frame of this element.

Figure 14:
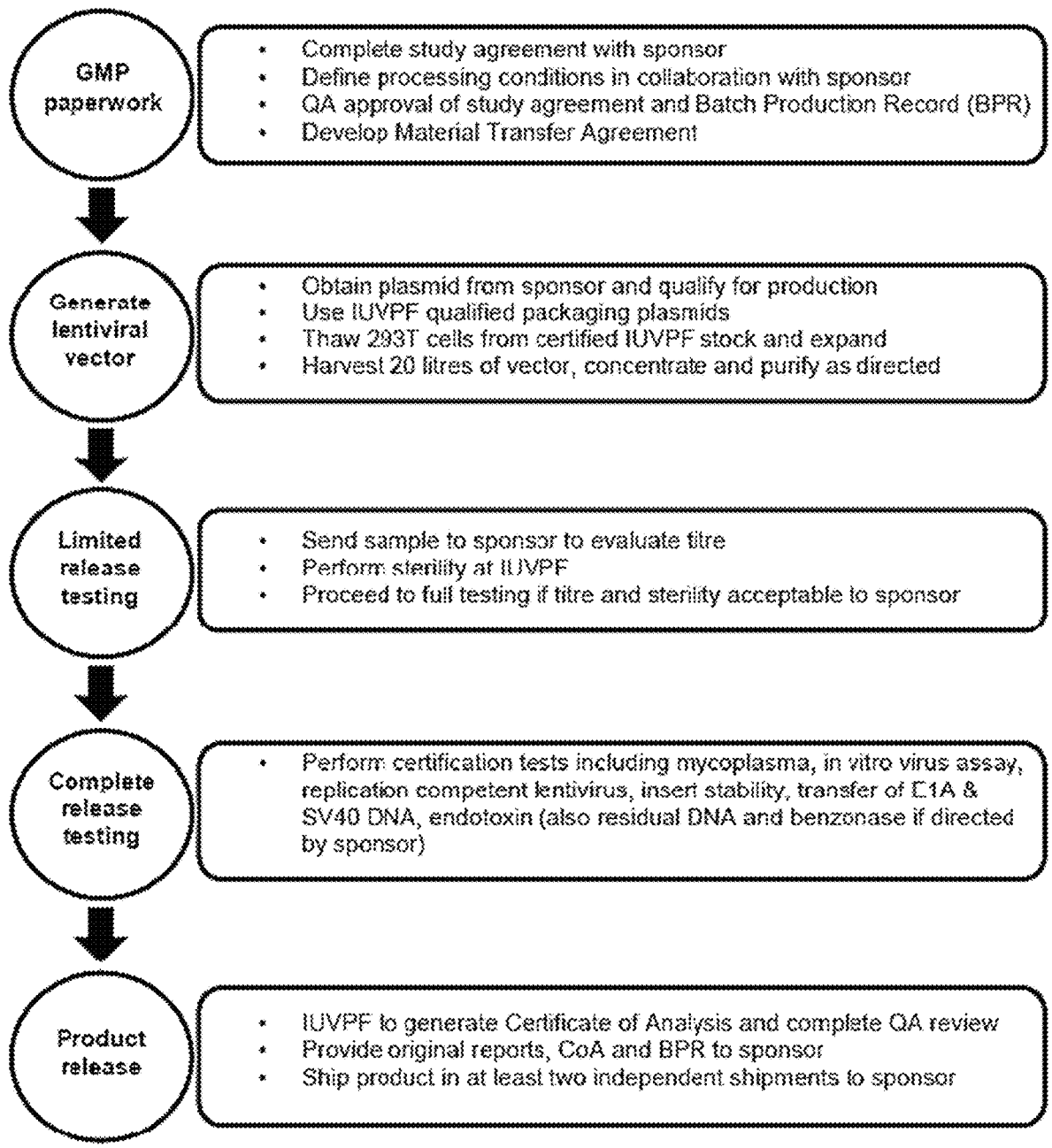
FIG. 14 is a schematic of the overview of the manufacturing process and process controls of the lentiviral vector.
Figure 17:
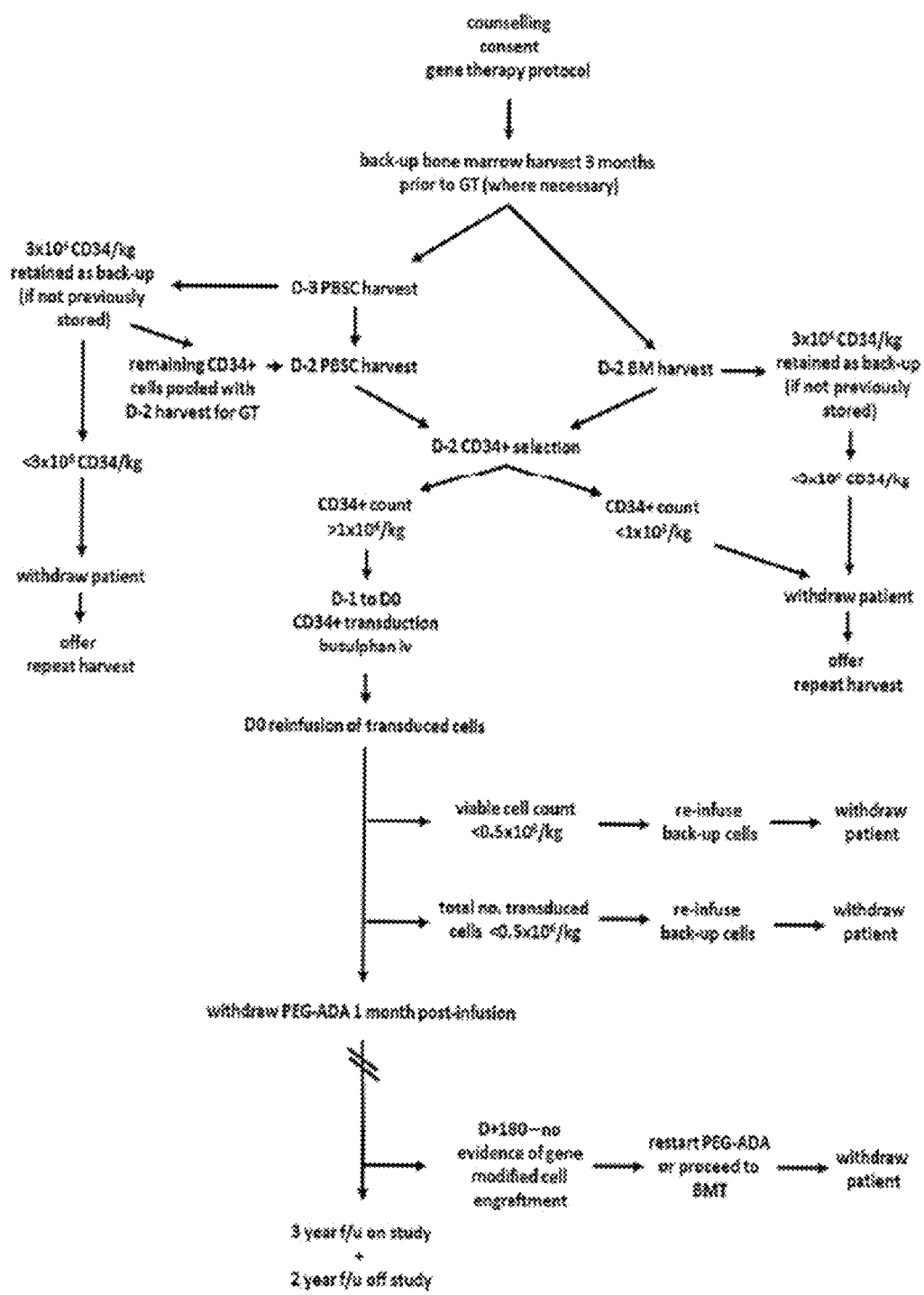
FIG. 17 is a detailed schematic of the trial design for the non-controlled, non-randomised Phase I/II clinical trial to assess the safety and efficacy of autologous transplantation of CD34+ cells from ADA-deficient SCID infants following human ADA cDNA transfer by the EFS-ADA lentiviral vector.
Figure 18:
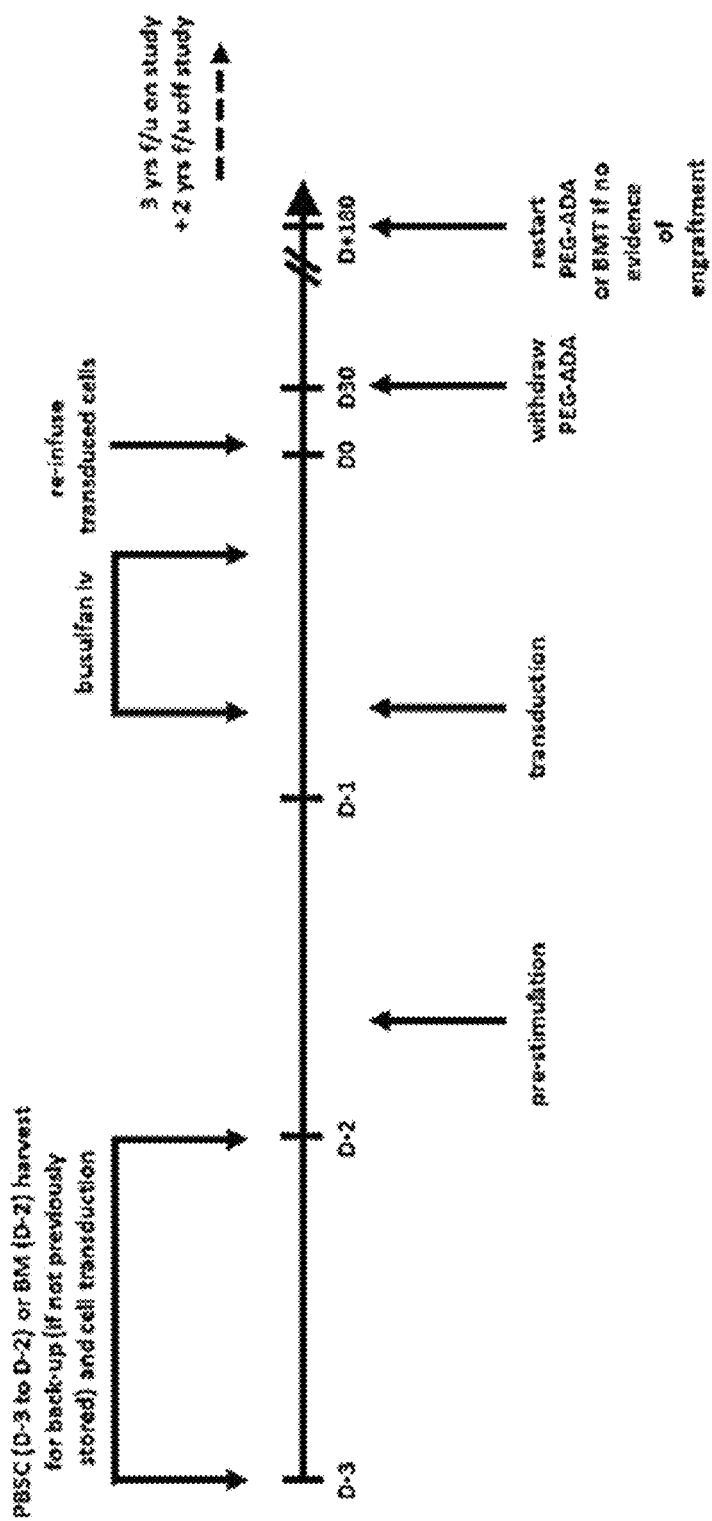
FIG. 18 is a schematic of the trial design for the non-controlled, non-randomised Phase I/II clinical trial to assess the safety and efficacy of autologous transplantation of CD34+ cells from ADA-deficient SCID infants following human ADA cDNA transfer by the EFS-ADA lentiviral vector.

An overview of the manufacturing process and process controls for the EF1αS-ADA lentiviral vector are outlined in FIGS. 14, 17, and 18. Clinical batches of the vector were produced by: Indiana University Vector Production Facility (IUVPF), 980 W. Walnut Street, R3-C602C Indianapolis, Ind. 46202-5254. Vector was produced at the Indiana University Vector Production Facility according to defined production and release testing standard operating procedures (SOPs) and the Batch Production Record. The facility occupies a 4,258 ft2, controlled access cGMP compliant space on the 6th floor of the R3 Building, 980 West Walnut Street, R3-C605, Indianapolis, Ind., US 46202-5188. The ISO Class 7 space contains four vector production rooms (each approximately 210-220 sq. ft.). Each production room has corresponding entrance and exit anterooms. The ISO Class 8 clean room space contains the main entrance anteroom (272 sq. ft.); pre-Production area (497 sq. ft.); released materials storage area (208 sq. ft.); media preparation room (188 sq. ft.); access corridor (203 sq. ft.); pre-production exit anteroom (105 sq. ft.); post-production exit anteroom (165 sq. ft.); post-production area (530 sq. ft.); freezer area for production storage (297 sq. ft.); and liquid nitrogen Dewar storage (118 sq. ft). The air handling system is dedicated to the facility and is independent from all other systems in the building. A Siemens Building Management System provides 24/7 monitoring and alarms for environmental parameters and equipment. The facility has a dedicated security system controlled by the IU VPF staff. Outside the cleanroom space is a Vector Testing Lab (600 sq. ft.), Molecular Sample Prep Lab (150 sq. ft.), Molecular Diagnostics Lab (320 sq. ft.), BL3 Lab for RCL Testing (450 sq. ft.), Administrative offices (200 sq. ft.) and a Quality Compliance Office (150 sq. ft.).

The IU VPF cleanroom and testing services worked under current Good Manufacturing Practices (GMP) in the preparation of materials for Phase I/II. Only retroviral and lentiviral vectors were generated in the cleanroom. The IU VPF had dedicated Quality Compliance Specialist (QCS) for the facility.

Vectors were generated using a working HEK293T cell Master Cell Bank. All work is performed under a specific Standard Operating Procedure (SOP) for lentiviral production and Batch Production Records capture the procedure. The procedure used two forms of purification, ion exchange chromatography and diafiltration using tangential flow filters; the latter was also used to concentrate the final product.

Production began by starting cell expansion: (1) A vial of certified Master Cell Bank (HEK293T cells) was thawed and placed into a flask and expanded over a 2 week period until sufficient cells were available for production; (2) The cells were harvested, pooled in a sterile bag and each layer of the CF is plated with $4.2 \pm 0.4 \times 10^7$ cells and 100 ml of media (note: once cells are placed into CF further processing through final vialing was conducted in a closed system); (3) Commercially available transfection kits were used that comply with GMP materials. Sequences of the third generation packaging plasmids are on file with the FDA. The CaPhos/DNA mixtures was prepared according to manufacturer's specifications; (4) Cells were re-fed 16 to 24 hours after transfection with harvest medium.

To prepare for vector harvest, all containers were prepared and labels are QA approved. Environmental Monitoring (EM) was performed throughout the harvest. Using a closed system, media was harvested from each CF and passed through a series of clarifying filters. The harvested media was then placed at 4° C. for up to 24 hours pending collection of the second harvest. After the second harvest was performed, the two harvests were pooled and then processed. To initiate purification and concentration, the pooled vector was subjected to benzonase treatment to remove residual plasmid DNA (50 U/ml). The material was purified by passing vector through a MustangQ ion exchange capsule. Vector was eluted in high salt and quickly brought back to low salt concentration. The material was then introduced into a closed-system tangential flow filtration apparatus (hydrophobic polysulfone membrane) sterilized by a GMP-compliance radiation source. Timing, flow rates, and permeate volumes were carefully documented throughout the procedure. The product underwent a 5-10 volume diafiltration to remove small molecular weight contaminants, further concentration was performed by altering pressure differential across the membrane with a target concentration of 100 fold. Vector was vialed in FDA approved sterile bags normally used for cryostorage of cellular products.

IUVPF has HIV-1-based "third generation" vector systems. The four plasmid system is used composed of: (1) the vector plasmid, (2) a plasmid expressing the required viral proteins (gag and pol), (3) a plasmid expressing Rev and (4) a plasmid expressing the VSV-G envelope. The optimal concentration for many vector transgene plasmids has been determined by IUVPF to be 13.2 μg per 75 $cm^2$ but this is confirmed for each new plasmid prior to initiating GMP production. The packaging plasmids used are: pMDLg (6.6 ug per 75 cm2), pRSV/Rev (3.3 μg per 75 $cm^2$) and VSV-G glycoprotein expression plasmid pMD.G (4.62 μg per 75 $cm^2$). The plasmid identity and purity must be acceptable according to IUVPF SOPs.

Phase I/II Clinical Trial Protocol

Figure 13:
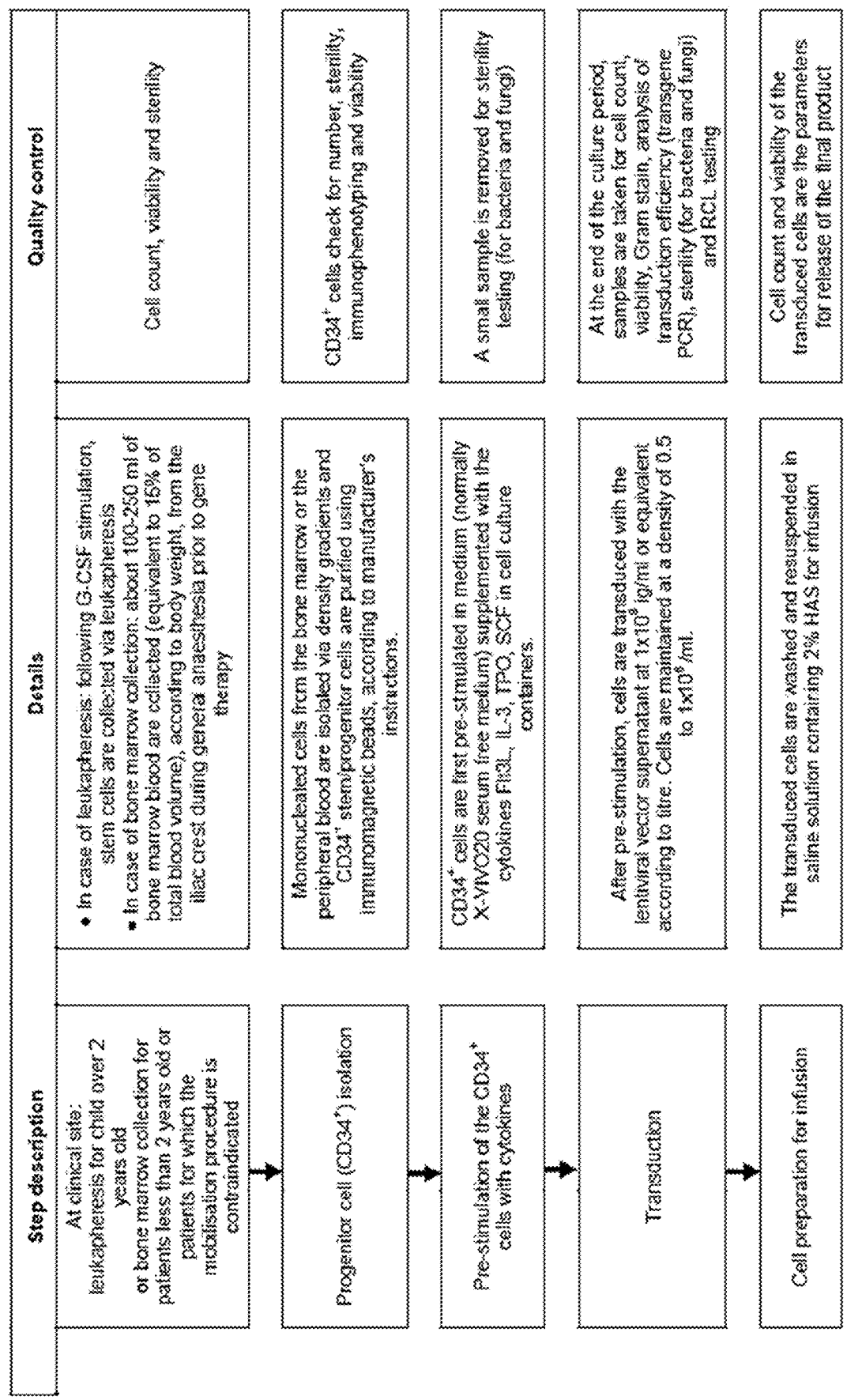
FIG. 13 is a schematic of the manufacturing process and in-process controls for the production of patient cell preparations for infusion.

A summary of the protocol for the production of transduced patient cell preparation for clinical infusion is provided in FIG. 13.

For the non-controlled, non-randomised Phase I/II clinical trial, to assess the safety and efficacy of autologous transplantation of CD34+ cells from ADA-deficient SCID infants following human ADA cDNA transfer by the EFS-ADA lentiviral vector, subjects received the infusion of their autologous, transduced cells following marrow cytoreduction with busulfan.

Patients were selected on the basis of inclusion and exclusion criteria detailed below. A back-up harvest was retained in case of failure of reconstitution following conditioning and re-infusion of transduced cells. For the transduction protocol, CD34+ cells were purified from G-CSF mobilised PBSCs recovered by leukapheresis (Plerixafor could be added to enhance mobilization), whenever possible or from bone marrow harvested under general anaesthetic. Back up cells of $3 \times 10^6$ CD34+/kg were stored from a single procedure if sufficient cell counts were available (and if not previously stored). The remaining CD34+ cells were taken forward for transduction. If less than $3 \times 10^6$ CD34+ cells/kg were harvested from the back-up, the patient was withdrawn from the study. Patients for which less than $1 \times 10^6$ CD34+ cells/kg were available for transduction did not proceed to conditioning, were withdrawn from the study and were offered a repeat harvest about 3 months later. Patient conditioning was initiated immediately after bone marrow or PBSC collection (busulfan i.v. weight adjusted dose). After purification, CD34+ cells were immediately transduced with the lentiviral vector, then evaluated for sterility, cell count, and viability, and immediately infused into patients. Several other tests for safety including testing for RCLs were performed on reinfused cells and results recorded retrospectively. If less than $0.5 \times 10^6$ viable cells/kg were returned to the patient, then back-up bone marrow/PBSCs were returned and patients withdrawn from the study. PEG-ADA was withdrawn one month post-infusion. If there was no bone marrow recovery by 6 weeks (ANC<0.5×10$^9$/L or platelets <20×10$^9$/L) the back-up harvest was re-infused. Patients were followed up on study at 1 month, 6 weeks, 3, 6, 9, 12, 18, 24, 30 and 36 months post gene therapy. The patient were then reviewed annually off study for a further 2 years. If after 180 days there was evidence of the transgene in PBMCs by qPCR or there was no evidence of T cell recovery, then patients were re-started on PEG-ADA and withdrawn from the study. PEG-ADA may be restarted prior to this time point on clinical grounds e.g., infective problems or delayed immune reconstitution and at this stage, and the subject withdrawn from the study.

Up to 10 patients were recruited from the Immunology Unit at Great Ormond Street Hospital. Referrals for enrolment in the study were accepted from centres worldwide. Individuals were selected for inclusion on the basis of the following defined criteria: (1) Diagnosis of ADA-SCID confirmed by DNA sequencing or by confirmed absence of less than 3% of ADA enzymatic activity in peripheral blood or (for neonates) in umbilical cord blood erythrocytes and/or leucocytes or in cultured fetal cells derived from either chorionic villus biopsy or amniocentesis, prior to institution of PEG-ADA replacement therapy. (2) Patients who lack a fully HLA-matched family donor. (3) Patients less than 5 years of age or patients less than 5 years of age who have preserved thymic function as evidenced by presence of less than 10% naïve T cells (CD4+45RA+27+ cells). (4) Parental/guardian signed informed consent. Exclusion criteria were as follows: (1) Cytogenetic abnormalities on peripheral blood. (2) Evidence of infection with HIV-1 & -2, hepatitis B, HCV. (3) Evidence of active malignant disease. (4) Known sensitivity to busulfan.

The first part of the study involved performing laboratory tests to determine whether the subject met the inclusion criteria and does not have a contraindication which would exclude them from the trial. For those included in the study, if a back-up has not previously been stored, haematopoietic stem cells were collected from the patient as a back-up at the time of leukapheresis (on day 3) or bone marrow harvest (on day 2). A back up of 3×10$^6$ CD34+/kg were stored. The total cell count required for both back-up (3×10$^6$ CD34+ cells/kg) and for transduction with LV vector (1×10$^6$ CD34+ cells/kg) is 4×10$^6$ CD34+ cells/kg. The bone marrow or leukapheresis cells were frozen and stored un-manipulated in liquid nitrogen vapours (−162° C. and −180° C.) to constitute the back-up graft. The back-up was in case the final cell dose is very low as specified or if no haematopoietic recovery was observed after 6 weeks, following the gene therapy treatment.

CD34+ cells for gene therapy were obtained preferably by leukapheresis (possibly augmented with Plerixafor) of G-CSF mobilised peripheral blood stem cells (PBMCs). If PBMC leukapheresis is not clinically appropriate or is contraindicated or where mobilisation fails, a bone marrow harvest was performed. PBMCs were the preferred choice as higher number of CD34+ cells are obtained which in turn allows gene modification of larger stem cell numbers prior to reinfusion into the patient.

For PBMC collection, recombinant human granulocyte colony stimulating factor (rhu G-CSF) was administered by subcutaneous injection (usually in the abdominal region) for 6 successive days (dose 5-16 µg/kg per day) (possibly augmented with Plerixafor) prior to harvest. CD34+ cell counts were monitored from day 4, and leukapheresis is performed on days 5 and 6 providing that the CD34+ cell count is greater than 1×10$^4$/ml.

If a bone marrow harvest was used as the source of CD34+ cells, bone marrow was harvested from the patient under general anaesthesia from the posterior iliac crests on both sites by multiple punctures. The amount of marrow collected was equivalent to 20 ml/kg of body weight. This gives a total nucleated cell count of greater than 10$^8$ cells/kg. This in turn would typically yield CD34+ cell dose of greater than 10$^6$ cells/kg after CD34+ cell selection.

CD34+ cells was separated by standard CliniMACs cell purification using protocols which are in routine use as part of the bone marrow transplantation programmes. Purified cells were immediately transferred to the gene therapy laboratory for transduction.

CD34+ cells were purified, cultured and transduced in a dedicated GMP compliant gene therapy laboratory at Great Ormond Street Hospital. CD34+ cells were purified using standard protocols for stem cell transplantation (CliniMACs), and seeded into fresh closed cell culture bags or flasks in serum free medium (X-VIVO-20, Lonza) supplemented with 1% human albumin solution (HAS, Baxter), and cytokines SCF (300 ng/ml), Flt-3 ligand (300 ng/ml), TPO (100 ng/ml) and IL-3 (20 ng/ml) at a density of 0.5-1×10$^6$/ml. All cytokines (Peprotech) and culture reagents were approved for ex vivo clinical use. After ~18 hours total pre-stimulation, cells were cultured with EFS-ADA lentiviral vector supernatant for 24 hours in the same complete media at a cell concentration of 0.5-1×10$^6$/ml. Following transduction, a portion of cells were removed for quality control (analysis of transduction efficiency, viability, sterility, RCL). The remaining cells were resuspended in saline containing human albumin solution (HAS) 2% in order to be administered to patient.

Samples were collected during and at the end of the procedure for cell viability (trypan blue stain, 7AAD staining or validated equivalent) and sterility (for Gram stain, bacteria and fungi) (see FIG. 13). Tests for transduction efficiency (transgene PCR) and ADA expression are performed after infusion of cells were recorded retrospectively.

For cell expansion, a vial of HEK293T cells were thawed and placed into a flask according to IUVPF SOPs. Vial identity was verified by a second IUVPF person. Cell viability was determined according to IUVPF SOPs (acceptable limit >50%). The flask was placed in a 37° C./5% CO2 incubator. Cells were examined every 8-12 hours after thawing and re-fed or subcultivated according to IUVPF SOPs. Cells were passaged by increasing the size and number of flasks until sufficient cells are available to inoculate a predetermined number of cell factories (CF). Prior to plating in CFs, the cells were harvested, pooled in a sterile bag and counted according to IUVPF SOPs. Each layer of the CF was plated with 5×10$^7$ cells and 100 ml of media. Generally, cell expansion occurred in DMEM+10% fetal bovine serum, D10. Using CF with Luer lock adaptors, the bag of prepared cells is mixed and the cell suspension was added to the sequentially numbered CFs and labelled. The CFs were placed in the incubator and checked to ensure each layer is completely covered with media and appears level.

For transfection of plasmids, cells were expanded within the CF until they were 70-80% confluent. The medium was removed and replaced with pre-warmed fresh media then returned to the 37° C., 5% CO2 incubator for approximately 2-4 hours while the transfection mixture was prepared. Commercially available transfection kits were used that comply with GMP materials (Promega, Madison, Wis.). The CAPHOS mixtures were prepared according to manufacturer's specifications and recoded in the BPR. The transfection mixture was introduced into the CF by Luer port. A second IU VPF staff member was present to verify DNA was added to each CF. Cells were re-fed within 24 hours after transfection with serum-free medium (OptiProSFM, Invitrogen).

For the preparation of cell harvest, prior to vector harvest, all containers were prepared and labels were QA-approved as described in IUVPF SOPs. Environmental monitoring was performed throughout the harvest using Sabouraud Dextrose settling plates and obtaining "glove" contact plates as specified in the cleanroom SOPs. Immediately prior to supernatant harvest each CF was examined to ensure absence of contamination, excessive cell death or other indications of abnormal cell growth. Media was harvested from each CF and passed through a clarifying filter. The supernatant was pooled in a container (e.g. 20 L Stedim bag) and certification test samples were collected as defined in IUVPF SOPs. If additional harvests were to be performed, each CF received fresh media and was returned to the 37° C./5% CO2 incubator. The harvested media was then placed at 4° C. for up to 24 hours pending collection of the second harvest. If a second harvest was performed, the two harvests are pooled before further processing.

For benzonase treatment, the product was treated with benzonase to decrease the amount of residual plasmid DNA left over from the transfection procedure. The standard final concentration in the harvested product was 50 U/ml, which was introduced into the "injection/collection (septum) port" of the processing apparatus. The treatment could be performed for up to 60 minutes at room temperature or overnight at 4° C.

For concentration and diafiltration, the material was purified using MustangQ ion exchange columns then further concentrated using MiniKros® disposable hollow fiber tangential flow filters (Spectrum Laboratories, Rancho Dominguez, Calif.) to concentrate the material. By maintaining equal pressure across the membrane filter, the vector product could also undergo diafiltration with serum free media to remove impurities. The filters used were made of hydrophobic polysulfone membrane, pyrogen free products or parts that were assembled, packaged and sterilised prior to use. Individual components could be adapted (i.e. volume and need for concentration). Timing, flow rates, and permeate volumes were carefully documented throughout the procedure. The target concentration generally an initial volume of 20 litres to be concentrated to between 1 and 20% of the original volume.

For vialing, the final containers could be vials or bags, depending on the intended use and volume required. Products were stored at less than −70° C. in a dedicated quarantine freezer. Reserve samples of the final vial product were also stored for analysis or archiving. The product yield was calculated and recorded on the BPR. Post production cells from each CF were collected by trypsinisation, the pooled cells were counted and stored in DMSO according to IUVPF SOPs. The cells were released for testing.

All critical steps during vector production were controlled. The IU VPF cleanroom and testing services worked under current Good Manufacturing Practices in the preparation of materials for Phase I/II. Only retroviral and lentiviral vectors were generated in the cleanroom. The IU VPF has a dedicated Quality Compliance Specialist.

During transduction of CD34+ cells, patient commenced conditioning. Patients received non-myeloablative conditioning with intravenous busulfan. Busulfan dose was weight dependent, in accordance standard doses known in the art (Bartelink et al. 2012). A wash-out period of at least 24 hours was maintained prior to reinfusion of the transduced cells. Pharmacokinetic monitoring of busulfan levels was performed after administration of the first dose. Cells will be washed and infused in a volume of −10-20 mls/kg intravenously over 30-45 minutes. A baseline set of observations were carried out before the infusion began (temperature, pulse, respirations, blood pressure, oxygen saturations). These were repeated 15 minutes into the infusion and then again at the end of infusion. Regular monitoring (frequency and duration dependent on reaction/occurrence) was commenced if anything abnormal (e.g. allergic reaction) occurred during the infusion or if antihistamines were administered. Dosing was sequential. The minimum length of time between each treatment of individual patients was 1 month.

Detailed analysis of immune recovery following gene therapy for primary immune deficiency was carried out to evaluate the effectiveness of the procedure. Specifically, the following was measures: (1) diversity and complexity of T and B reconstitution; (2) thymic education and output following gene modification of lymphocyte precursors; and (3) measure cellular antigen specific responses. The analyses was carried out on pre- and post-treatment samples. The results were interpreted as a change in value over time through a longitudinal analysis for each patient.

A gene therapy lymphocyte subsets (LSS) immunophenotyping panel was carried out to show the distribution of cells and is used to detect an increase in naïve CD3+ T lymphocyte cell numbers and assess the development of normal distribution of CD4, CD8, TCRαβ, TCRγδ, CD19 and CD16+CD56+ NK cell populations. TCR excision circles (TRECs) could be enumerated as a surrogate marker for new thymic emigrants following gene therapy. Whole blood lymphocyte proliferation assays were carried out to test function of T cells and will include responses to mitogens (PHA—phytohaemagglutinin) and antigen specific responses when necessary. Representation of TCR families by flow cytometric analysis (Vβ phenotyping), combined with CDR3 PCR spectratyping (Vβ spectratyping) also formed an important part of monitoring for both physiological and potentially pathological clonal expansions. Restoration of antibody production (IgA, IgM, IgG), and serological responses to vaccinations were assessed.

Metabolic assays were carried out at the Purine Research Laboratory and included analysis of red blood cell ADA activity, dATP and dAdo levels. These indicated how effectively gene therapy has corrected the metabolic phenotype of ADA-SCID. Molecular characterisation of gene transfer in patient cells was also an important parameter for assessment of efficiency, and potentially for assessment of safety. Quantification of transgene copy numbers was determined on sorted cell populations by real-time PCR methodologies. This was performed on peripheral blood samples and on bone marrow samples (if available). Detailed integration analysis could be used to investigate specific clonal expansions. Analysis of lentiviral vector integration sites was performed by specialised PCR based techniques and by high throughput sequencing of lineage specific populations. This was performed on peripheral blood samples and on bone marrow samples (if available).

Statistical Analysis

Descriptive statistics of continuous outcome variables, such as the means and standard error by experimental groups, are presented in figures and data tables. For continuous outcome measurements, group differences were assessed by unpaired t-test (for two experimental groups) or one-way/two-way analysis of variance with interaction (for more than two groups) followed by pairwise comparisons. Linear mixed models were used for dose-dependent analysis. Concentration and MOI were modelled as the fixed effects, while experiments or donors were data. Wilcoxon rank sum test was used for IVIM assay analysis. For all statistical investigations, tests for significance were two-tailed unless otherwise specified. Significance level is expressed as follows: (*) if P<0.001; () if 0.01>P>0.001; (*) if 0.05>P>0.01; (ns) if P>0.05. A P value less than the 0.05 significance level was considered to be statistically significant (*).

Example 1

Comparison of Previously Used gRV Vectors with the Novel LV Vector

Vectors used are shown in FIGS. 1A and 1B. First, it was shown that LV ADA can efficiently transduce murine and human HSCs. Lineage depleted bone marrow cells (Lin−) isolated from ADA−/− mice (ADA−/− HSC) were isolated and transduced with viral vectors at a multiplicity of infection (MOI) of 20 under optimized protocols. Normalized enzymatic activity (ADA activity/vector copy) showed that LV EFS ADA had similar efficacy of transgene expression in murine ADA−/− HSCs compared with gRVSFada/W (FIG. 2A). Similar levels of ADA protein expression were detected in ADA−/− HSC by western blot analysis (FIG. 2B) and demonstrated that LV EFS ADA mediates efficient transduction and transgene expression in ADA−/− HSCs. LV EFS ADA was also compared to another gRV used previously in a clinical trial, gRV MND-ADA and an LV in which the MND LTR U3 enhancer/promoter controls ADA expression (LV MND ADA). Human cord blood CD34+ cells (CB HSC) were transduced with LV EFS ADA over a range of LV concentrations ($10^6$-$10^8$ TU/ml; MOI of 10-1,000) and with gRV MND-ADA (generated from a stable PG13 cell clone) at $1.8 \times 10^5$ TU/ml. After short-term myeloid culture for 2 weeks, there was a significant dose-dependent trend between LV concentration during transduction and both the resultant vector copy number (VCN) (P=0.002) and ADA gene expression as measured by the ADA enzyme activity over background activity (P=0.003) (FIGS. 2C and 2D). Transduction of CB HSC with each of the LVs at $1 \times 10^7$ TU/ml resulted in 1-3 vector copies per cell, and gRV MND-ADA, applied at a 100-fold lower dose, resulted in only ~0.2-0.8 copies per cell, but when normalized for VCN, activity was similar for LV EFS ADA and gRV MND-ADA (~1-2 ADA U/VC) (FIG. 2E). Although, ADA activity/VC was higher with LV MND-ADA (P=0.03), it is not a preferred choice for clinical HSC GT, as it harbors a strong gRV LTR enhancer/promoter which has increased mutagenic potential. The ADA activity in the LV EFS ADA-transduced ADA-deficient SCID BM cells was 24-fold higher than endogenous levels in the mock-transduced samples; ADA activity in LV EFS ADA-transduced normal donor CB and BM HSC was one- to threefold over endogenous levels in mock-transduced ADA-replete donor samples (FIG. 2F).

Transplantation of LV EFS ADA transduced ADA−/− Lin− cells rescued lethality in ADA−/− mice. ADA−/− mice normally die within 3 weeks following withdrawal of PEG-ADA. We transplanted young adult ADA−/− mice with ADA−/− Lin− cells that had been transduced with either LV EFS ADA or SFada/W or with ADA+/+ Lin− cells (WT Lin− group). For all groups, PEG-ADA treatment was carried over for 4 weeks after transplantation to promote engraftment before complete withdrawal. The survival rate was 100% in the LV EFS ADA group and the WT group, which was significantly higher than ADA−/− SFada/W group in which the survival rate was 40% (P=0.02) (FIG. 3A). To evaluate integration of the viral vector and engraftment of donor cells in vivo, we performed quantitative polymerase chain reaction (qPCR) to evaluate VCN and male donor Y chromosome mononuclear cell (MNC) engraftment in PB at 13 weeks after transplantation. Similar levels of donor cells were present in the PB of the gRVSFada/W group (45.3±0.4%) and WT Lin− (44±21.7%) groups, while the level of donor cells was two-fold less in the LV EFS ADA group (20.1±2.5%) (FIG. 3B). However, in the latter, VCN was 0.85±0.16 copy/cell compared with 0.42±0.2 copy/cell in the gRVSFada/W group (FIG. 3C). Comparison of immune recovery after LV- and gRV-mediated gene delivery in ADA−/− mice was then analyzed by assessing the total numbers of PB mononuclear cells (PBMCs) and the percentages of lineage specific populations within the mononuclear cell population (% of MNCs). Compared to all other groups, untreated ADA−/− mice had reduced numbers of total PBMCs and less than 10% of the MNCs were CD3+ (FIG. 3D). In the LV EFS ADA or gRVSFada/W groups, more than 69% of the MNCs were CD3+, which included elevated levels of both single positive CD4+ and CD8+ cells which were similar to the levels observed in mice transplanted with WT HSCs (WT Lin− group) or age-matched mice under PEG-ADA treatment (ERT group). Although no significant improvement was detected in the percentage of B220+ cells with any treatment, taking into account the total cell numbers, the absolute number of B220+ cells in all transplants was much improved in comparison to untreated ADA−/− mice. In addition, GR-1+ myeloid cells and NK1.1+ cell numbers were corrected to relatively normal levels. To evaluate the development of the immune system upon ADA restoration, lymphoid organs including thymus and spleen were isolated from untreated and treated ADA−/− mice and lymphoid subpopulations were analyzed by flow cytometry. Overall, untreated ADA−/− mice had the lowest total cell numbers (FIG. 3E), as well as the lowest CD3+ and B220+ percentages of total mononuclear cells, in the thymus and spleen (FIGS. 3F and 3G). In the thymus, the early CD4-CD8- population was two-fold higher in untreated mice, highlighting the block in thymocyte development found in ADA deficiency (FIG. 3F, lower panel). In transplants with LV- or gRV-transduced HSCs, we found significantly increased MNCs in all spleens (P<0.05), and to a lesser extent, in thymi (P<0.05) (FIG. 3E). Among thymocytes, the CD3+ proportion was significantly elevated (P<0.05). More importantly, the average percentage of CD4-CD8- double negative thymocytes was reduced from 12% in untreated ADA−/− mice to only 4.6% in GT groups. This result demonstrates that the block in thymocyte development was overcome with restored ADA expression. In spleens of mice receiving transduced cells, there was an elevated percentage of CD3+ cells compared to untreated controls (P<0.05) that was similar to WT transplants and mice treated with ERT alone (FIG. 3G). B-cell percentages were similar to those in untreated mice but in relation to total cell number, there was a significant increase in absolute number of both CD3+ and B220+ cells in LV and gRV groups with no significant difference between these two groups (FIGS. 3F and 3G). These results suggest that the proliferation and differentiation of both T and B cells had been restored in the GT groups at levels that were similar to the levels in the WT transplant and ERT groups.

Figure 4C:
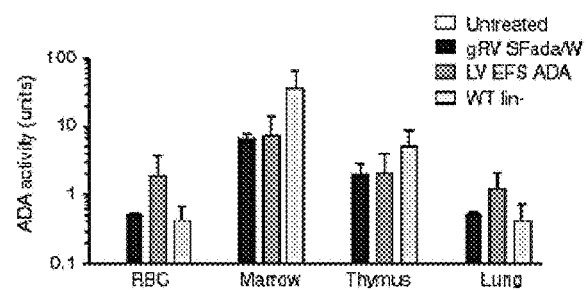
FIG. 4C is a graph of ADA activity in red blood cells, BM cells, thymocytes, and lung tissue of ADA−/− transplants and control mice were measured by enzymatic activity assay as indicated (mean±SD). (e) Histopathologic analysis of lung sections from ADA−/− transplanted with ADA−/− Lin− gRVSFada/W or ADA−/− Lin− LV EFS ADA or ADA+/+ WT Lin− cells compared to lung sections from 18-day-old untreated ADA−/− and ADA−/− mice under ERT (ADA−/− ERT) mice. All sections have been stained with hematoxylin and eosin.
Figure 4B:
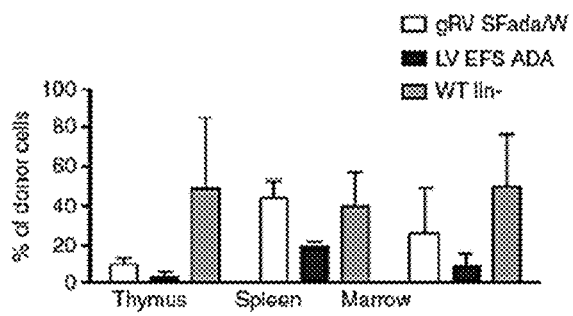
FIG. 4B is a graph of the percentage of donor cells in thymus, spleen, and bone marrow measured by quantitative PCR (qPCR). Percentage of DNA with Y chromosome were evaluated in sex-mismatched transplants indicated in FIG. 1A (mean±SD).
Figure 4D:
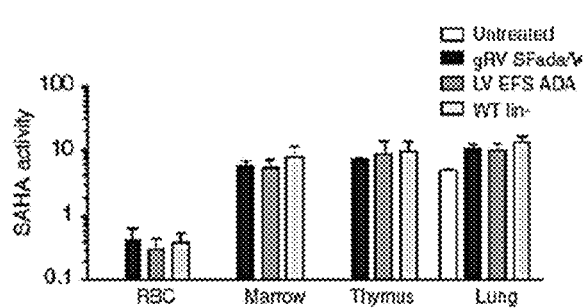
FIG. 4D is a graph of SAHA activity in red blood cells, BM cells, thymocytes, and lung tissue of ADA−/− transplants and control mice were measured by enzymatic activity assay as indicated (mean±SD).
Figure 4E:
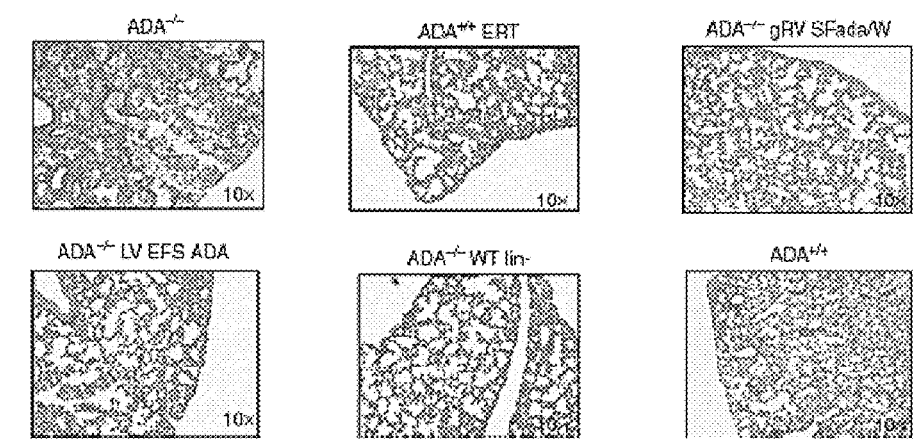
FIG. 4E is a series of photographs of histopathologic analyses of lung sections from ADA−/− transplanted with ADA−/− Lin− gRVSFada/W or ADA−/− Lin− LV EFS ADA or ADA+/+ WT Lin− cells compared to lung sections from 18-day-old untreated ADA−/− and ADA−/− mice under ERT (ADA−/− ERT) mice. All sections have been stained with hematoxylin and eosin.

In recipients with LV-transduced cells, we detected a two-fold increase in VCN in thymus (0.2±0.15), spleen (1.1±0.34), marrow (0.44±0.32) compared to those with gRV-transduced cells (FIG. 4A). Donor cell engraftment was determined in mismatched sex transplants by qPCR for sequences on the Y chromosome. The level of Y chromosome detected in the spleens of mice in the LV EFS ADA group was twofold lower (19.6±2.0%) compared to the gRVSFada/W group. Likewise, the level of donor engraftment or level of Y chromosome in thymi from mice in the LV EFS ADA group were also twofold lower than those with gRVSFada/W, and ten-fold lower than engraftment in the WT Lin− group (FIG. 4B). Although donor engraftment appears to be lower with transduced (LV or gRV) cells, this may represent dilution of the transplanted donor cells with the host cells that are cross-corrected by the overexpression of ADA from the vector in the primary lymphoid organs. This dilution effect has been described previously and is specific to ADA-SCID because there is cross-correction of uncorrected ADA-deficient cells with adequate ADA activity provided by ERT, HSCT, or GT. ADA−/− mice have undetectable ADA enzyme activity and decreased SAHH activity in most tissues and organs. To confirm the expression of functional ADA by LV EFS ADA and gRVSFada/W in vivo, we analyzed ADA and SAHH activities in multiple systems including nonlymphoid organs such as the lung (FIGS. 4C and 4D). In PB and lymphoid organs including spleen and thymus, ADA activities in the LV EFS ADA and gRVSFada/W groups were comparable to activities in WT Lin− transplantation group in (FIG. 4C), which is noteworthy given the engraftment of transduced ADA−/− donor cells in the thymus was measured to be ten-fold lower compared to ADA+/+ WT Lin− donor cells (FIG. 4B). In a nonimmune organ, such as the lung, ADA enzymatic activity was also equivalent in all GT treated mice in comparison to WT transplants and undetectable in untreated mice (P<0.05). Similar ADA activities were also found in livers of the transplants. Inhibition of S-adenosyl homocysteine hydrolase (SAHH) activity is secondary to the accumulation of dATP in ADA-deficient mice. In all transplants, untreated mice showed absent or low levels of SAHH activity in RBC, thymus, spleen, BM, and lung, whereas LV GT treated mice showed increased SAHH activity to levels similar to the WT Lin−-treated mice (P<0.05) (FIG. 4D). These results demonstrate that LV EFS ADA-mediated gene transfer can lead to efficient metabolic correction in the ADA-deficient mouse that is at least comparable to correction with gRVSFada/W and WT Lin− HSCT. We also studied other organ pathologies in untreated and treated mice. Non-lymphoid organs including lung, liver, heart, and kidney were harvested and examined histologically. The dominant pathologic improvements were observed in the lungs of treated mice (FIG. 4E). Untreated ADA−/− mice showed occlusion of the airways and thickening of airway epithelium with accumulation in the airspaces of proteinaceous material and infiltration of alveolar macrophages. There was a striking improvement in all treatment groups, including LV EFS ADA and gRVSFada/W groups, with clearance of interstitial fluid and absence of inflammatory cells with lung histology similar to that seen in ADA−/− WT Lin− mice. There were no predominant findings in the structure or organization of other organs in untreated and treated mice.

Example 2

Figure 5A:
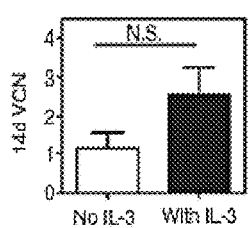
FIG. 5A is a graph of VCN measurements in human cord blood CD34+ cells that were transduced with LV EFS-ADA ($3 \times 10^7$ TU/ml) in medium with recombinant human cytokines SCF/ckit ligand, flt-3 ligand, and thrombopoietin (TPO), with or without interleukin-3 (IL-3) cultured for 14 days in vitro under myeloid differentiation conditions (N.S., not significant).
Figure 5B:
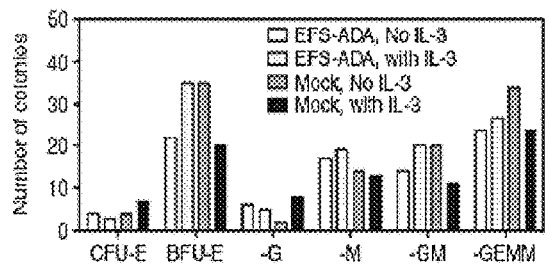
FIG. 5B is a graph depicting the number of colonies from transduced CD34+ cells grown in a colony-forming unit (CFU) assay in methylcellulose and assayed after 2 weeks.
Figure 5C:
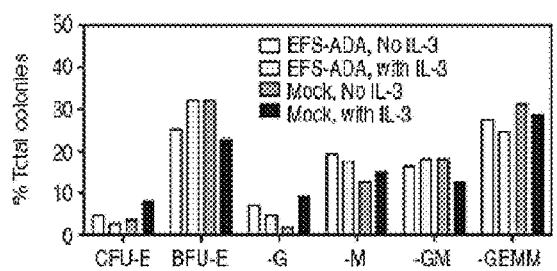
FIG. 5C is a graph of the types of colonies formed by CD34+ cells in CFU assay.
Figure 5D:
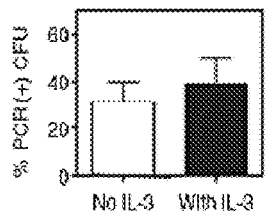
FIG. 5D is a graph of the percentage of colonies positive for vector sequence by PCR for the human ADA cDNA (% PCR (+) CFU).
Figure 5E:
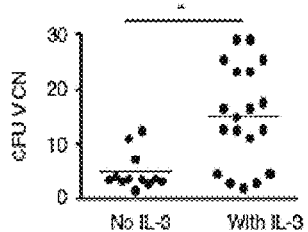
FIG. 5E is a graph of the VCN quantified in DNA extracted from individual CFU by qPCR (*P=0.001).
Figure 5F:
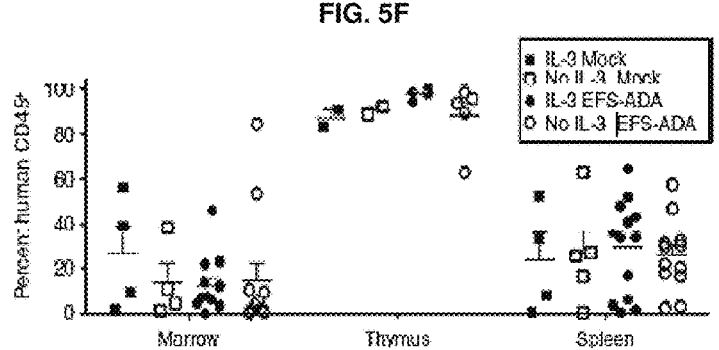
FIG. 5F is a graph of the percent of human CD45+ cells engrafted in the bone marrow, thymus (when present) and spleen by FACS of tissue cell suspensions immunostained with anti-human CD45 (% hCD45+). Transduced CD34+ cells were transplanted into NSG mice and analyzed after 4 months for engraftment of human cells based on FACS analysis of huCD45 expression.
Figure 5G:
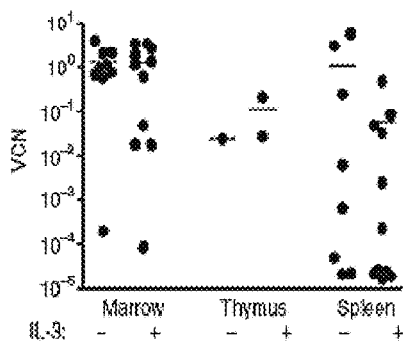
FIG. 5G is a graph of EFS-ADA VCN in bone marrow, thymus (when enough cells were available for analysis; total n=3), and spleen.
Figure 5H:
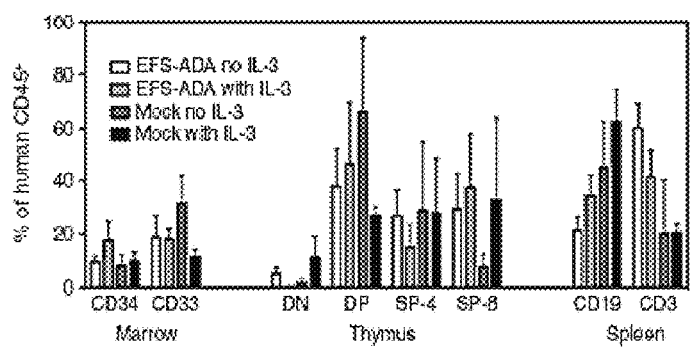
FIG. 5H is a graph describing the immunophenotypic analysis of human CD45+ cells in NSG bone marrow (CD34+ and CD33+), thymus (CD4−/CD8− double-negative (DN), CD4+/CD8+ double-positive (DP), CD4+ single-positive (SP-4) and CD8+ single-positive (SP-8)) and spleen (CD19+ and CD3+).

EFS-ADA Transduction of Normal and ADA-deficient Human Cord Blood and Bone Marrow CD34+ Cells Analysed In Vitro and Vivo To further evaluate LV EFS ADA and to gain insight into the effects of IL-3 on LV transduction of human HSC, we compared transduction and long-term engraftment of the CB CD34+ cells, with and without IL-3 included in the pre-stimulation and transduction media. CB HSC (n=2) were thawed, plated (500,000 cell/ml), and prestimulated for 20 hours in medium containing human stem cell factor, human FLT3-L and human TPO (S/F/T), with or without IL-3 (20 ng/ml). The prestimulated cells were transduced with LV EFS ADA ($3.0 \times 10^7$ TU/ml) or mock transduced. To test the effects of IL-3 exposure on the engraftment of more primitive stem/progenitor cells, LV EFS ADA-transduced or mock-transduced CD34+ cells were xenotransplanted into Nod/SCID/γ C (NSG) primary and secondary mouse recipients. The VCN measured after 14-day short-term culture was two-fold higher with IL-3 (2.5±0.8) compared to without IL-3 (1.2±0.4), but this difference was not significant (FIG. 5A). Likewise, there were no significant differences in the total numbers of colony-forming units (CFUs) produced per 1,000 plated CD34+ cells in the LV-transduced group (no IL-3: 87/1,000=8.7%, with IL-3: 109/1,000=10.9%) compared to the mock transduced (no IL-3: 109/1,000=10.9%, with IL-3: 83/1,000=8.3%), nor in the different types of colonies formed (FIGS. 5B and 5C). Although inclusion or exclusion of IL-3 did not make a significant difference in the percentage of CFU colonies containing LV sequences (39.3% with IL-3 versus 31.1% without IL-3), the mean VCN in DNA from individual CFU was 3.1-fold higher when IL-3 was included (15.1±2.1) than when it was not (4.9±10) (P=0.001) including, a subset of CFU with an average VCN>10 only when exposed to IL-3 (FIGS. 5D and 5E). Between postnatal day 1 and 3, sub-lethally irradiated (150 cGy) NSG neonates were transplanted with 100,000 CB CD34+ cells (IV), either mock-transduced with IL-3 (n=5) or without (n=5), or transduced with LV EFS ADA with IL-3 (n=13) and without IL-3 (n=14). Engraftment was not different in tissues isolated from mice transplanted with LV EFS ADA transduced or mock-transduced human CD34+ cells, with or without IL-3 (FIG. 5F). VCN was measured in bone marrow, thymus, and spleen and corrected for the level of engraftment (FACS for huCD45) and was not different in tissues isolated from mice transplanted with LV EFS ADA transduced with or without IL-3 (FIG. 5G). There were no significant differences in the lineages of the engrafted human cells in the BM (CD34 and CD33), spleen (CD19 and CD3), and thymus (DN, DP, SP-4, SP-8) in any of the groups (FIG. 5H). Unfortunately, only 1 out of a total of 35 secondary adult recipient mice from two separate experiments had human cell engraftment, and therefore, we were unable to determine any effects of IL-3 on HSC transduction at the most primitive stem cell level.

We further evaluated LV EFS ADA for transduction efficacy, engraftment, and differentiation in human ADA-deficient SCID BM CD34+ cells (ADA-SCID HSC). ADA-SCID HSC were freshly isolated and transduced with LV EFS ADA at $3.3 \times 10^7$ TU/ml or mock transduced (n=3) and analyzed in parallel by in vitro assays and in vivo by transplantation into NSG neonates. CFU assays in methylcellulose were enumerated and characterized by their morphology for lineage type after 12 days. The LV- and mock-transduced cells grew similar numbers and types of colonies: LV EFS ADA 289 colonies/14,000 cells plated (2.1%); mock transduced 50 colonies/2,000 cells plated (2.5%) (FIGS. 6A and 6B). Colonies that grew from the LV EFS ADA-transduced cells (n=2) were 95% positive for the LV vector sequence (FIG. 6C). After short-term in vitro myeloid culture, LV EFS ADA-transduced cells had a mean ADA activity of 4.6±1.4 U, which was >92-fold higher than the background ADA activity of mock-transduced ADA-deficient cells (0.05±0.02 U; one-sided P=0.03) (FIG. 6D). The LV EFS ADA-transduced cells had a mean VCN of 2.92±0.75 and expressed 1.55±0.22 ADA U/VC. Four months after HSCT of ADA-SCID HSC into NSG mice, engraftment of human cells varied considerably among recipients (2-90%) but was not different with LV EFS ADA compared to mock-transduced cells in bone marrow (mock 31.2%; LV 28.7%), spleen (mock 28.9%; LV 34.7%), or thymus (mock 95.9%; LV 90.0%) (FIG. 6E). Notably, transduction by the LV EFS ADA vector did not impair differentiation of the ADA-SCID HSC. In the bone marrow of mice transplanted with mock-transduced cells, 9.5% (±1.2) of the human CD45+ cells expressed the hematopoietic stem/progenitor cell marker CD34 compared to 8.5% (±1.3) in mice transplanted with LV EFS ADA-transduced cells. Similarly, myeloid markers CD14 and CD11b were expressed on 7.3% (±4.5) and 10.4% (±4.4) of the human CD45+ cells from mice transplanted with mock-transduced and LV EFS ADA-transduced cells, respectively (FIG. 6F). Thymocytes isolated from recipients of LV EFS ADA-transduced ADA-SCID HSC had typical proportions of CD4/CD8 double-negative (10.7%), CD4/CD8 double-positive (54.6%), CD4 single-positive (10.1%), and CD8 single-positive cells (24.6%) (FIG. 6F). In contrast, thymocytes isolated from recipients of mock-transduced ADA-deficient CD34+ cells had typical proportions of only CD4/CD8 double-negatives (12.4%) and CD4 single-positive cells (11.7%), but had significantly more CD8 single-positive cells, (64.7%; P=0.020) and significantly less double-positive cells (11.2%; P=0.028) compared to mock transduced, suggesting abnormal thymopoiesis without ADA gene correction. In mature lymphocyte populations, there was no difference in the percentages of splenic CD3+ human T cells produced from the LV-transduced cells (13.2%) or mock-transduced cells (18.7%), but there was a higher percentage of splenic CD19+ human B cells produced from the LV-transduced cells (68.8%) compared to the mock-transduced cells (51.6%) (P=0.047). ADA enzyme activity was analyzed in enriched populations of human CD45+ cells isolated from the bone marrow and spleen, and from total thymocytes of the NSG mice. The mean ADA activity in thymocytes was 0.05±0.01 U from mice transplanted with mock-transduced cells and was 0.52±0.30 U from mice transplanted with LV EFS ADA-transduced cells (FIG. 6G). The relatively high ADA activity detected in mock transduced BM and spleen most likely derive from the murine cells, which are replete for ADA expression, contaminating the human CD45-enriched populations. VCN consistently averaged between 3.7 and 5.2 VC per cell in the three organs analyzed, with 1.3-1.8 U/VC ADA enzyme expression (FIGS. 6H and 6I).

A major concern regarding the continued clinical use of gRV is the risk of insertional mutagenesis. The in vitro immortalization (IVIM) assay has demonstrated the capability to detect transformation of virally transduced cells under myeloid differentiation conditions. In two independent studies, performed in the United Kingdom and in the United States, we adopted this approach and compared the LV EFS ADA to the gRVSFada/W and gRV MNDADA vectors. A second vector using the promoter/enhancer element of spleen focus-forming virus driving the green fluorescent protein reporter gene (gRVSF91GFP) was also used as a positive control in both studies. In the UK study, another positive control was included using a SIN LV design but with an internal SFFV promoter (LV SF GFP). In both studies, cells were also subject to mock transduction in similar culture conditions to monitor background activity. In the UK study, the gRV SF91 GFP vector induced positive replating clones in all experiments and the LV SF GFP vector did so in two out of four experiments. Most notably, the clinical gRVSFada/W vector also displayed positive replating activity in all experiments, suggesting that this vector has strong transformation ability. The LV EFS ADA-transduced cells did not produce clones with higher proliferative capacity than mock-transduced cells in any of the four independent experiments (FIG. 7A). The replating index (replating frequency/VCN) was calculated and, both gRVSF91GFP and gRVSFada/W vectors had high replating indices. The LV SF GFP vector harboring internal SFFV promoter displayed a relative lower replating index than gRVs. Importantly, the LV EFS ADA vector generated no detectable mutants resulting in a negative replating index. In a modification of previously described IVIM assays, cell proliferation was detected using the WST-1 assay method (IVIM-WST1 assay), in which viable cell numbers were determined by the measurement of products generated from cleavage of WST-1 by mitochondrial dehydrogenases thereby allowing a quantitative assessment of the growth of replating clones. Four independent experiments were conducted and the highest reading from mock-transduced clones was set as the threshold, values above which were regarded as positive clones. In the US study, four independent experiments (13 assays) were conducted. The gRVSF91.GFP and gRVMND-ADA retroviral vectors produced abundant immortalized clones, with replating frequencies/VCN of $3.36 \times 10^{-3}$ (or 1 in 306) and $3.68 \times 10^{-4}$ (or 1 in 2,717), respectively. No colonies were formed by the mock-transduced or the LV EFS ADA-transduced cells across all 13 assays performed. The frequency of replating by LV EFS ADA was significantly lower when compared to gRV SF91.GFP, (P<0.001) and when compared to gRVMND-ADA (P<0.001; by two sample nonparametric Wilcoxon rank sum test) (FIG. 7B). The distribution of unique vector integration sites was determined in LV EFS ADA-transduced human BM and CB CD34+ cells prior to transplant (in vitro) and in cells from the BM of NSG mice 4 months after transplantation (in vivo). LV EFS ADA integration patterns seen in the human cells after the short-term culture and in the cells after xenografting in vivo were essentially identical, with no in vivo clonal skewing toward a higher frequency of vector integrants in cancer-associated genes (FIG. 7C), and no dominant clones observed and also no increase of integrants near the 5' transcriptional start sites of genes (FIG. 7D).

Example 3

Figure 8A:
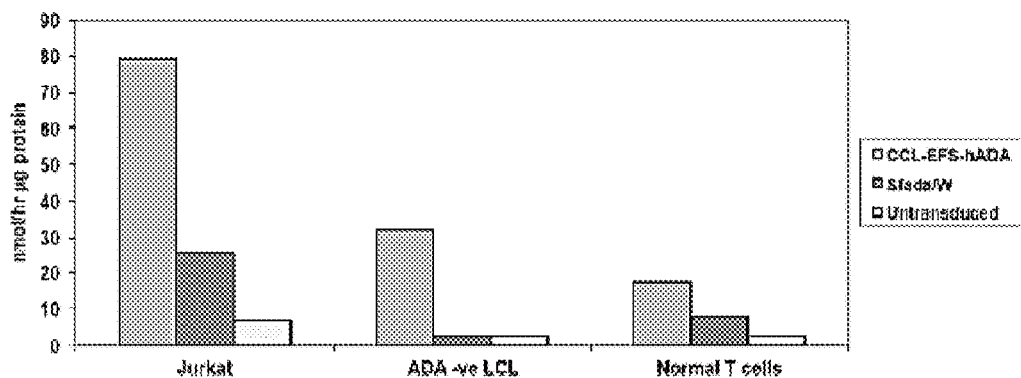
FIG. 8A is a graph of total ADA activity following transduction of Jurkat cells, ADA deficient EBV-LCLs and normal T cells using a EF1αS-ADA lentiviral vector or the Sfada/W γ-retroviral vector.
Figure 8B:
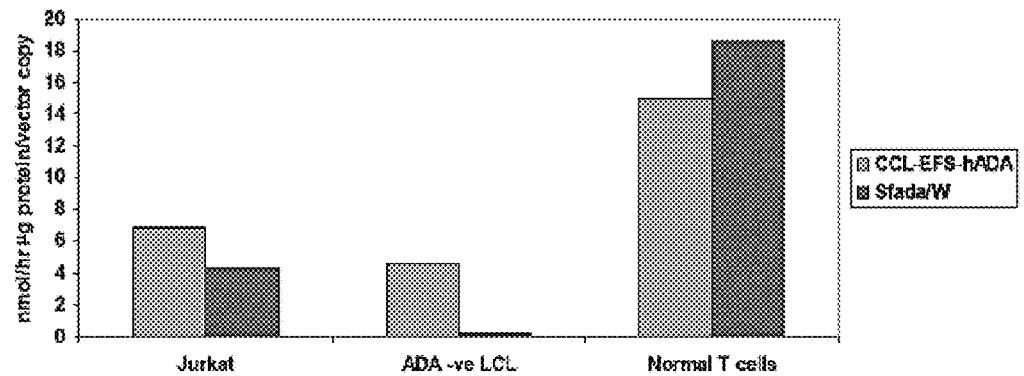
FIG. 8B is a graph of ADA activity normalised for vector copy number following transduction of Jurkat cells, ADA deficient EBV-LCLs and normal T cells using a EF1αS-ADA lentiviral vector or the Sfada/W γ-retroviral vector.

Further Pre-clinical Data Including Expression of ADA from the EFS-ADA LV Construct In initial experiments, we compared the ability of the EFS-ADA lentiviral vector to express ADA in comparison to the current clinical grade γ-retroviral vector (Sfada/W). Following transduction of 3 different cell lines, ADA expression following transduction of cells with the EFS-ADA lentiviral vector (normalised for vector copy number) was either equivalent to or superior than the expression seen in cells transduced with the Sfada/W vector. This included an EBV transformed LCL from a patient with ADA deficiency (FIGS. 8A and 8B). Total ADA activity is shown in FIG. 8A and activity normalised for vector copy number is shown in FIG. 8B.

Figure 8C:
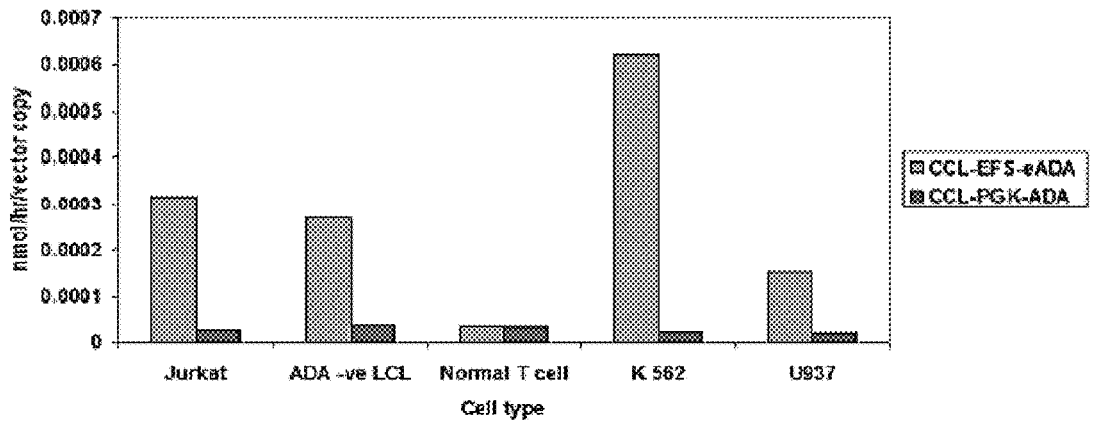
FIG. 8C is a graph of total ADA activity measured by HPLC in a variety of cell lines and in normal T cells using an EF1αS-ADA lentiviral vector or the Sfada/W γ-retroviral vector.
Figure 8D:
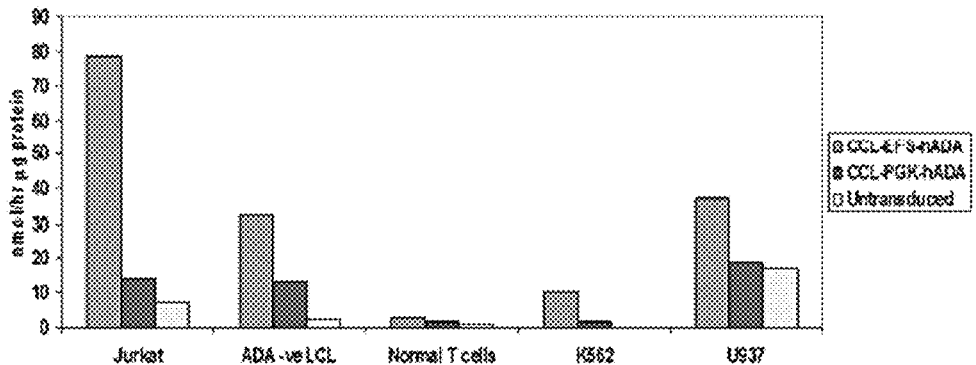
FIG. 8D is a graph of ADA activity measured by HPLC and corrected for vector copy number in a variety of cell lines and in normal T cells using an EF1αS-ADA lentiviral vector or the Sfada/W γ-retroviral vector.

In further studies compared the EFS-ADA lentiviral vector with a similar lentiviral vector in which the ADA gene was transcribed by an internal PGK promoter. A number of different cell lines were transduced including ADA-ve LCLs, primary T cells from a normal individual, Jurkat T cells, U937 cells and K562 cells. Viral supernatant of a similar titre and similar MOI were used for transduction purposes and in all cell lines other than the U937 line, the EFS-ADA lentiviral vector showed a higher transduction efficiency when transduced cells were analysed by intracellular ADA analysis. Cells were then analysed for ADA activity above baseline levels (as a low level of ADA activity is found in all human cell lines) and activity normalised for vector copy number which was determined by vector specific qPCR. In all cell lines other than normal primary T cells, the EFS-ADA lentiviral vector showed markedly higher ADA activity/copy number than the PGK-ADA lentiviral vector (FIGS. 8C and 8D). Total ADA activity is shown in FIG. 8C and activity normalised for vector copy number is shown in FIG. 8D. In similar experiments performed at UCLA, transduction of HT29 (colon carcinoma), C.E.M. (T cell leukemia), and an HTLV-1-transformed T cell line from a patient with ADA-deficient SCID again showed increased ADA activity/vector copy in cells transduced with the EF1αS-ADA lentiviral vector.

Figure 9A:
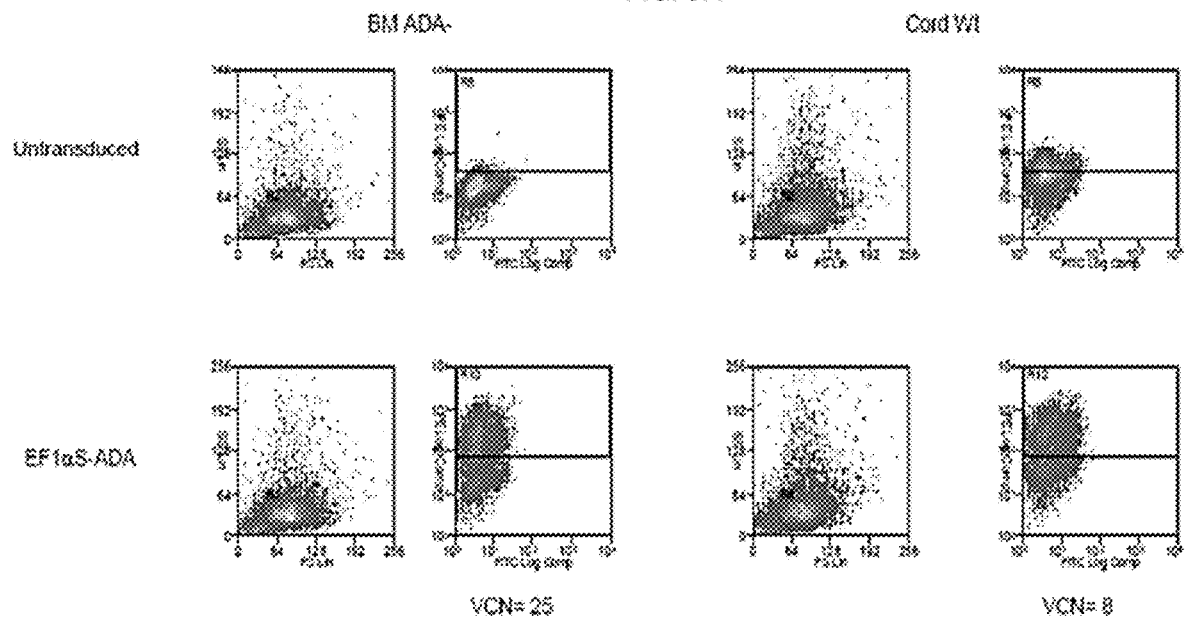
FIG. 9A is a series of plots showing intracellular ADA expression following EF1αS-ADA lentiviral vector transduction of CD34+ cells from wild type and ADA deficient individuals (VCN=vector copy number).
Figure 9B:
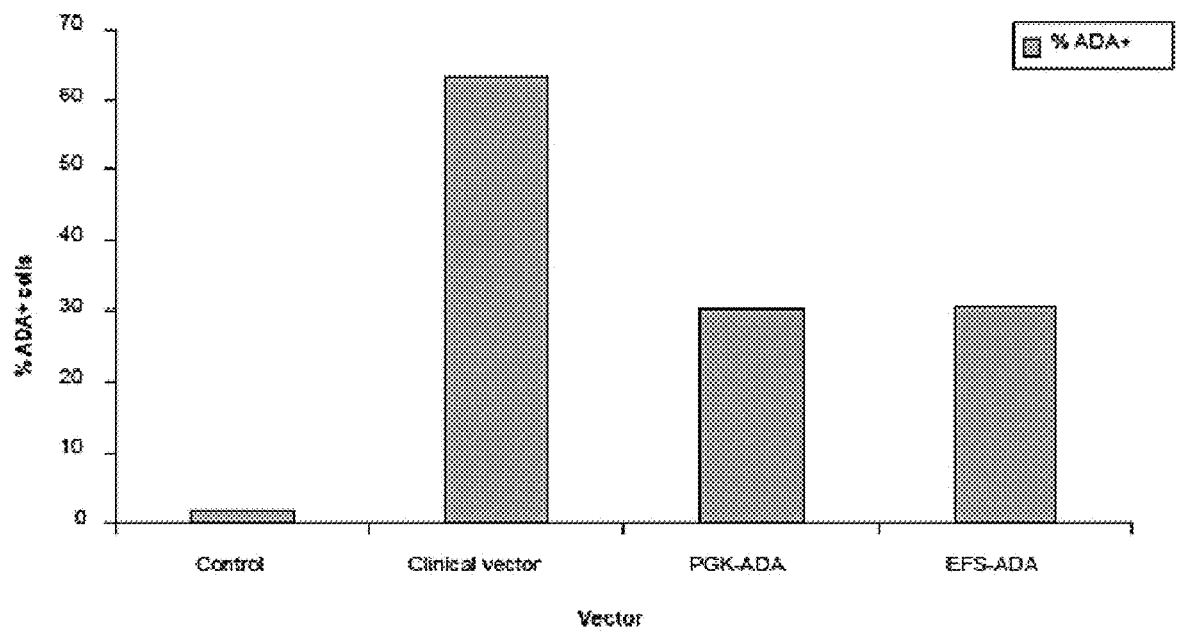
FIG. 9B is a graph of CD34-ve cells from an ADA deficient patient that were taken and transduced with the clinical grade γ-retroviral vector, pCCL EF1aS-ADA LLV vector or a pCCL PGK ADA LV vector and grown on a murine stromal layer expressing Notch-delta 1 ligand. Following T cell differentiation, the percentage of cells expressing ADA is shown.

To determine the ability of the EFS-ADA lentiviral vector to express ADA in human haematopoietic stem cells, CD34+ cells from cord blood or bone marrow of normal or ADA deficient patients respectively was obtained and transduced with the EFS-ADA lentiviral vector using the same cytokine cocktail to be used in the clinical transduction protocol. Following culture to allow cell number expansion, cells were stained and assessed for intracellular ADA expression by flow cytometry. Significant levels of ADA expression were seen in transduced cells from both ADA deficient and wild-type CD34+ cells (FIG. 9A). In further experiments, CD34+ cells bone marrow from an ADA deficient patient were transduced using either the EFS-ADA lentiviral vector, the PGK-ADA lentiviral vector or the γ-retroviral vector currently used in the GTAC 073 trial. Transduced cells were then grown on stromal cells in conditions conducive for development into T or NK cells. Viability and the extent of differentiation into the different lineages were similar for all 3 vectors (FIG. 9B).

Studies of these lentiviral vectors were also performed using human CD34+ cells isolated from normal umbilical cord blood. The CD34+ cells were transduced using the culture conditions used for the clinical trial, testing a range of vector concentrations. The transduced CD34+ cells were grown in culture for two weeks after transduction, and then cell samples assayed to quantify the vector copies/cell, using qPCR and the ADA enzymatic activity, using a colorimetric biochemical assay. Expressed ADA enzymatic activity per vector copy was then calculated. These studies showed that transduction, as measured by vector copy per cell, is directly related to the concentration of vector during transduction, with $10^7$ TU/ml leading to approximately 2 copies/cell. Expression of the transferred ADA cDNA was at a similar level by a lentiviral vector with an internal viral LTR (pCSO-re-MCU3-hADA), the EFS-ADA lentiviral vector used in the clinical trial and a γ-retroviral vector. These in vitro studies demonstrate that in both cell lines and in primary progenitor cells, the EFS-ADA lentiviral vector is able to transduce cells at efficiencies comparable to γ-retroviral vectors used successfully in current gene therapy studies and is also able to express the ADA cDNA leading to ADA activity at similar levels to that shown by γ-retroviral constructs.

In further experiments, we have transduced CD34+ cells selected from ADA-SCID patient bone marrow with either the EFS-ADA lentiviral vector (LV.SIN.EFS.hADA), the clinical SFFV LTR based clinical vector (SFada) or a vector expressing GFP only (LV.SIN.EFS.eGFP) and engrafted transduced cells into 8-10 week old irradiated immunodeficient mice (NSG (NOD/SCID/gamma c-/-) mice) (FIGS. 10A and 10B). Six mice were used in each group, although one of the SFada cohort died. In both bone marrow (FIG. 10A) and the spleen (FIG. 10B) of recipient NSG mice, cells transduced with either the LV.SIN.EFS.hADA or SFada construct engrafted at similar levels whereas no evidence of CD45+ cells was seen in mice receiving cells transduced with a GFP containing vector. Development of CD19 B cells or CD3 T cells in the spleen was similar between the two constructs. B cell differentiation was the most abundant cell type seen in the bone marrow or spleen and formed the vast majority of engrafted human CD45+ cells. These studies show that following transduction with the EFS-ADA lentiviral vector, ADA deficient CD34+ cells are able to engraft and differentiate in a human xenograft model at levels that are similar to that seen following transduction with the current SFada vector.

Figure 11A:
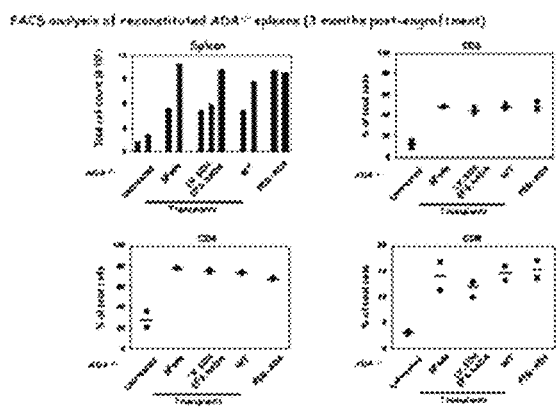
FIG. 11A is a series of FACS analyses plots of mice reconstituted with the LV.SIN.EFS.hADA vector, indicating that they have increased numbers of total cells in the spleen in comparison to ADA−/− mice. Murine lin-ve cells were either transduced using standard protocols with 1) the LV.SIN.EFS.hADA (n=3) or 2) SFada (n=2). Cells were returned to lethally irradiated recipients. Mice were analysed after 12 weeks and compared with ADA−/− mice, mice that had undergone wild-type transplant experiments (WT) or mice that had been treated with enzyme replacement therapy alone. The recovery of total cell numbers and of specific lymphocyte subpopulations including CD3, CD4 and CD8 T cells, are similar to that seen in mice reconstituted with SFada vector transduced cells and mice treated with wild type cells or PEG-ADA replacement therapy.
Figure 11B:
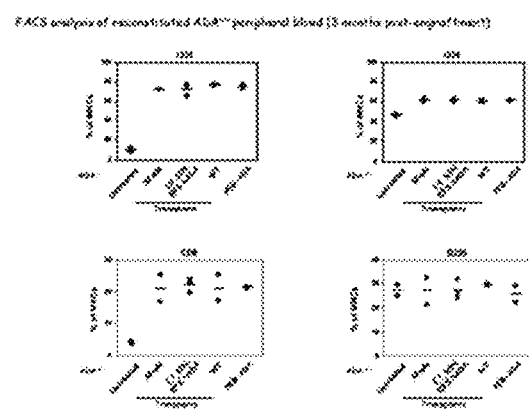
FIG. 11B is a series of FACS analyses plots of peripheral blood showing very low % of T cells in the mononuclear fraction of ADA−/− mice whereas reconstituted mice with both vectors, WT cells, or PEG-ADA treatment all show a marked increase in T cell recovery. B cell reconstitution is again similar between the different treatment groups.
Figure 11C:
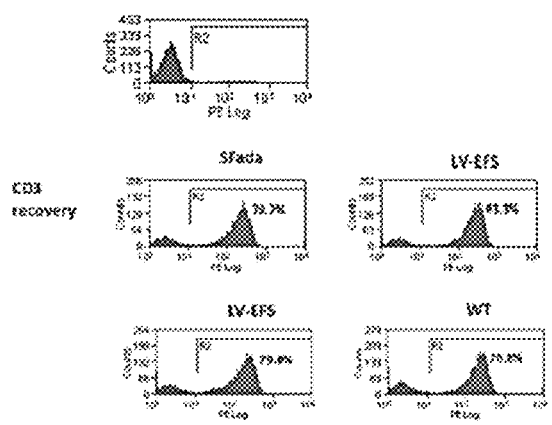
FIG. 11C is a series of plots showing a representation of the equivalence in T cell reconstitution.
Figure 11D:
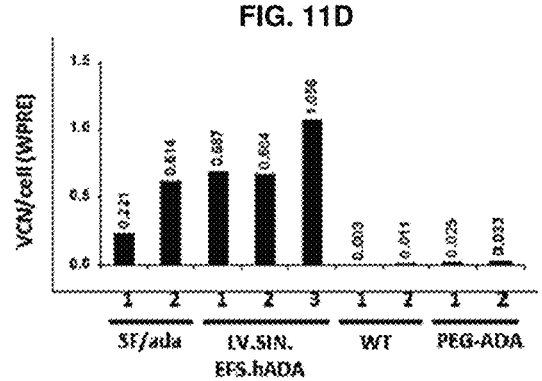
FIG. 11D is a graph of the vector copy number in the peripheral blood of mice transduced with either the LV-EFS or SFada vector suggesting that even with similar levels of virus transduction, equivalent levels of T cell reconstitution can be achieved.
Figure 11E:
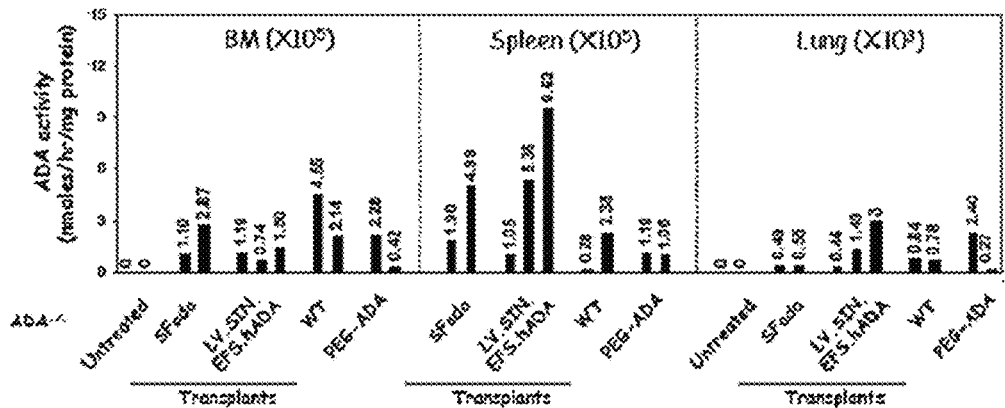
FIG. 11E is a series of graphs of ADA enzymatic activity showing similar measurements in both the marrow and spleen of mice transduced with LV-EFS vector in comparison to mice treated with SFada vector, WT transplants or PEG-ADA, and were greatly increased from levels seen in ADA−/− mice. Similar results were also seen in a non-immune organ such as the lung.
Figure 12B:
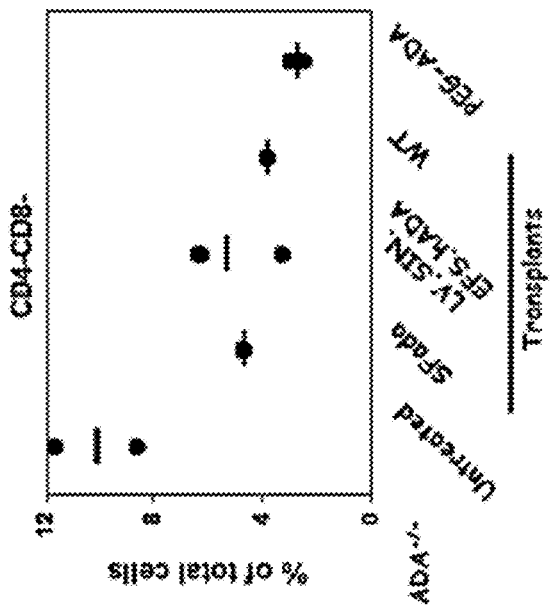
FIG. 12B is a graph showing the % of total CD4-CD8- cells of reconstituted mice with either vector or with WT or PEG-ADA treatment show similar levels of reduction of this population.
Figure 12A:
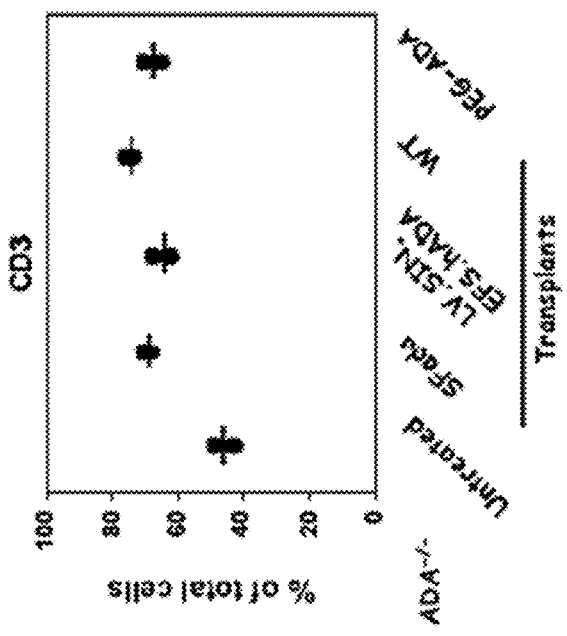
FIG. 12A is a graph showing the % of total CD3 cells of reconstituted mice with either vector or with WT or PEG-ADA treatment show similar levels of reduction of this population.

Early models of ADA deficient mice were limited by embryonic or peri-natal lethality as a result of severe hepatocellular and pulmonary damage. A two stage transgenic strategy in which ADA expression is restricted to trophoblasts rescues ADA null mice from pre- and peri-natal lethality and allows post-natal study of mice lacking ADA expression. In this model, many features of the human disease are accurately represented. Mice show abnormalities of thymic architecture with a significant block in thymocyte development at the CD4-CD8- double negative stage. In vitro analysis of thymocytes from these mice also demonstrates defects in later stages of thymocyte development due to the toxic effects of dATP and deoxyadenosine accumulation. In the periphery, there is a profound lymphopaenia with a severe T, B and NK cell deficiency that is seen in humans together with abnormalities in splenic lymphoid architecture and a paucity of splenic T cell populations. Murine ADA deficiency also manifests a number of non-immunological abnormalities including lung, renal, costochondral and neurological changes. Pulmonary problems are present in mice from ~postnatal day 12 and are associated with significant lung inflammatory changes, eventually leading to the death of mice by postnatal day 22 from pulmonary insufficiency, unless early treatment is initiated. Mice die by three weeks of age but can survive in response to enzyme replacement therapy with PEG-ADA. The immunological and systemic defects found in this murine model resemble closely many features of the human disease and this model is therefore an ideal system in which to test the ability of new ADA vectors to correct the disease phenotype. Murine lin-ve cells were either transduced using standard protocols with 1) the LV.SIN.EFS.hADA (n=3) or 2) SFada (n=2). Cells were returned to lethally irradiated recipients. Mice were analysed after 12 weeks and compared with ADA-/- mice, mice that had undergone wild type transplant experiments (WT) or mice that had been treated with enzyme replacement therapy alone. Mice reconstituted with the LV.SIN.EFS.hADA vector have increased numbers of total cells in the spleen in comparison to ADA-/- mice (FIG. 11A). The recovery of total cell numbers and of specific lymphocyte subpopulations including CD3, CD4 and CD8 T cells, are similar to that seen in mice reconstituted with SFada vector transduced cells and mice treated with wild type cells or PEG-ADA replacement therapy. Similarly analysis of peripheral blood (FIG. 11B) shows very low % of T cells in the mononuclear fraction of ADA-/- mice whereas reconstituted mice with both vectors, WT cells or PEG-ADA treatment all show a marked increase in T cell recovery. B cell reconstitution is again similar between the different treatment groups. A representation of the equivalence in T cell reconstitution is shown (FIG. 11C). Importantly, the vector copy number in the peripheral blood of mice transduced with either the LV-EFS or SFada vector were similar suggesting that even with similar levels of virus transduction, equivalent levels of T cell reconstitution can be achieved (FIG. 11D). ADA enzymatic activity was similar in both the marrow and spleen of mice transduced with LV-EFS vector in comparison to mice treated with SFada vector, WT transplants or PEG-ADA and were greatly increased from levels seen in ADA-/- mice. Similar results were also seen in a non-immune organ such as the lung (FIG. 11E). In the thymus, the major abnormalities in the ADA-/- mice are a block in thymocyte development with an accumulation of CD4-CD8- thymocytes. Reconstituted mice with either vector or with WT or PEG-ADA treatment show similar levels of reduction of this population (FIGS. 12A and 12B).

Clinical grade LV.SIN.EFS.hADA vector was characterised for its ability to transduce CD34+ cells from ADA-/- patients. Using clinical grade reagents and a clinical protocol involving 18 hrs prestimulation and followed by 1 round of lentiviral transduction for 24 hrs, either $1\times10^8$ (~MOI of 100) or $5\times10^7$ (~MOI of 50) viral genomes were added to $\sim1\times10^6$ CD34+ cells. As shown in FIG. 16A, these clinically applicable transduction conditions resulted in effective CD34+ cell transduction with viral copy numbers of ~1-1.3 copies/cell. In addition there was preservation of CD34+ integrity with little change in the percentage of stem cells through the culture period D0-D3 (FIG. 16B).

Example 4

Genotoxicity of the EFS-ADA LV Construct: The EFS-ADA LV Construct is Safer than the LTE Intact gRV Constructs We have shown that the risk of insertional mutagenesis from a SIN lentiviral vector design in general is low as determined in both in vitro and in vivo systems. One in vitro assay has been developed and tested by a number of groups and is gaining recognition as the most reliable test of the transformation potential of different viral constructs. The in vitro immortalisation assay (IVIM) detects clonal dominance of insertional mutants which expand in initially polyclonal cultures of primary murine haematopoietic cells within two weeks after gene transfer and acquire serial replating ability, the extent of which provides a measure of clonal fitness. When different vector designs were tested in this assay the SIN lentiviral vector design shows significantly less transformation potential than current LTR intact γ-retroviral designs. To test the oncogenic capacity of SIN-lentiviral vectors in vivo, the tumor-prone Cdkn2a-/- mouse model has been previously used. Haematopoietic stem cells from these mice were isolated and transduced in similar conditions with SIN LV or LTR intact γ-retroviral constructs expressing reporter genes. A vector with a similar backbone as the ADA vector, but expressing a neutral eGFP reporter gene, was tested in this system and no genotoxicity was found even upon integration of ~6 copies of vector per cell. In contrast, LTR-active γ-retroviral vectors were measurably genotoxic, suggesting that the intrinsic genotoxicity of the pRRL LV (the backbone used in this study) is low.

Further, the EFS promoter was shown to be safer than the viral LTR. Using the IVIM assay, the EFS promoter was compared under equivalent conditions to the SFFV LTR in the context of a SIN γ-retroviral vector. In this assay, a SIN vector with the internal EFS promoter was significantly (P<0.01) less mutagenic than a SIN vector with the internal SFFV promoter. Under conditions that resulted in death of mock-transduced cells, the SIN vector containing an internal EFS promoter was unable to induce sustained growth of mutants, even when the average copy number was >40. In contrast, transformed clones were always observed with the SIN vector containing the internal SFFV promoter, and with this vector, an average copy number of ~2 was sufficient to induce transformation. This indicates that the transactivating potential of the SIN vector with the EFS promoter is at least substantially diminished. Of note, SIN vectors containing 'insulator' elements flanking the internal SFFV promoter-driven cassette showed a significantly greater degree of transforming activity that the SIN vector with the EF1αS promoter (4/4 experiments; P<0.01). Together these studies indicate that the transactivating potential of γ-retroviral vectors are substantially reduced by SIN configurations, and further reduced by the utilization of EF1αS internal regulatory sequences.

Further in vivo studies have also established the low transformation capacity of SIN vectors containing the EFS promoter. These experiments were conducted as safety studies for a trial of gene therapy for SCID-X1 (GTAC 116) and are relevant here because of the use of the same EF1αS promoter. SIN γ-retroviral constructs containing the EFS promoter and driving expression of the IL2RG or GFP reporter transgene were evaluated in murine transplant experiments in wild type C57/BL6 experiments. Briefly, lin-ve cells from donor mice were isolated and transduced under standard conditions with vectors containing EFS-IL2RG or EFS-GFP or media alone (mock controls). Twenty mice were transplanted for each experimental group and were observed for a period of 10-12 months. There were 17 evaluable mice in the IL2RG group, 17 evaluable mice in the EGFP group and 18 evaluable mice in the mock group. On average, there was 60-80% engraftment in each group. The average vector copy number in peripheral blood mononuclear cells, determined by real-time PCR at 2 months post-transplant was 1.25 copies/cell for the IL2RG test group and 2.2 copies/cell for the EGFP control group. Two host cell derived malignancies were noted in the test IL2RG group. One vector-negative thymoma and an ovarian tumor were noted in the GFP vector group. Host cell derived malignancies are not unexpected in this mouse model, and the frequency is not higher than previously reported values by our group. There were no cases of vector positive donor cell derived leukemias in the IL2RG test group. There was one vector positive, donor cell derived T cell lymphoma noted in a C57BL/6J recipient mouse which received the EGFP control vector. These data suggest that in the context of a SIN configuration and coupled with the IL2RG gene, the EFS promoter has not been associated with demonstrable tumorigenesis in wild type murine transplant experiments.

Figure 15A:
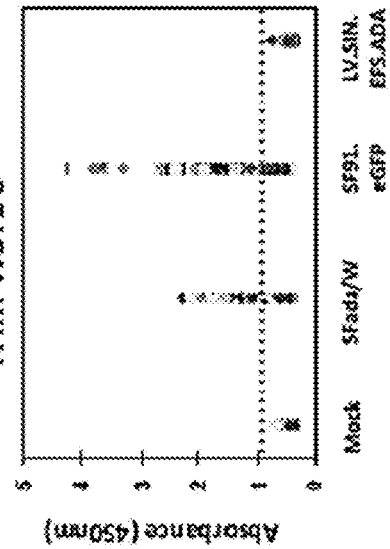
FIG. 15A is a table displaying data from consecutive experiments, wherein cells transduced with the LTR driven γ-retroviral vectors gave rise to transformed clones with replating ability, whereas no transformed clones above background (or mock transduced) levels were detectable in cells transduced with the EF1αS-ADA lentiviral vector despite equivalent or higher vector copy numbers.
Figure 15B:
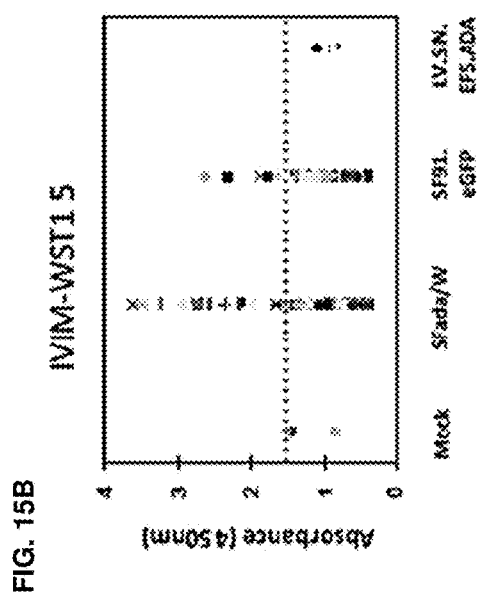
FIG. 15B is a series of graphs representing the proliferative capacity in a WST-1 assay of clones from SFada/W and SF91.GFP transduced cells showing high levels of proliferation whereas clones from EF1αS-ADA LV transduced cells have levels of proliferation no higher than that seen in mock transduced cell clones.

The IVIM assay was used to test the transformation ability of SFFV LTR driven vectors expressing GFP (SF91.GFP) or dsRED (SF91.dsRED) reporter genes, the SFFV LTR clinical γ-retroviral vector used in GTAC 073 (SFada/W) and the EFS-ADA lentiviral vector. In consecutive experiments, cells transduced with the LTR driven γ-retroviral vectors give rise to transformed clones with replating ability whereas no transformed clones above background (or mock transduced) levels were detectable in cells transduced with the EFS-ADA lentiviral vector (FIG. 15A) despite equivalent or higher vector copy numbers. In this assay, the genotoxic potential of the EFS-ADA lentiviral vector is considered to be low and significantly lower than the transformation potential of the vector currently used in clinical trials. In order to test objectively whether clones derived following transduction were viable and had significant cytokine independent proliferative capacity, clones were analysed using the WST-1 assay. The assay is based on the reduction of WST-1 by viable cells which produces a soluble formazan salt. The procedure involves initial incubation of cells with the WST-1 reagent, followed by spectrophotometric assay of coloured product. In two experiments independent experiments, any clones derived from cells transduced with the SFada/W, SF91.GFP, EFS-ADA LV vectors or mock transduced cells were studied further in the WST-1 assay. As seen in FIG. 15B, in both experiments, clones derived following SFada/W or SF91.GFP transduction showed levels of proliferation that were far higher than the baseline proliferation seen in mock transduced clones. In contrast any clones derived following EFS-ADA LV transduction showed negligible proliferative capacity and were no greater than levels of proliferation seen in mock transduced cells.

Example 5

Clinical Trial Data from Humans

Figures 19A, 19B:
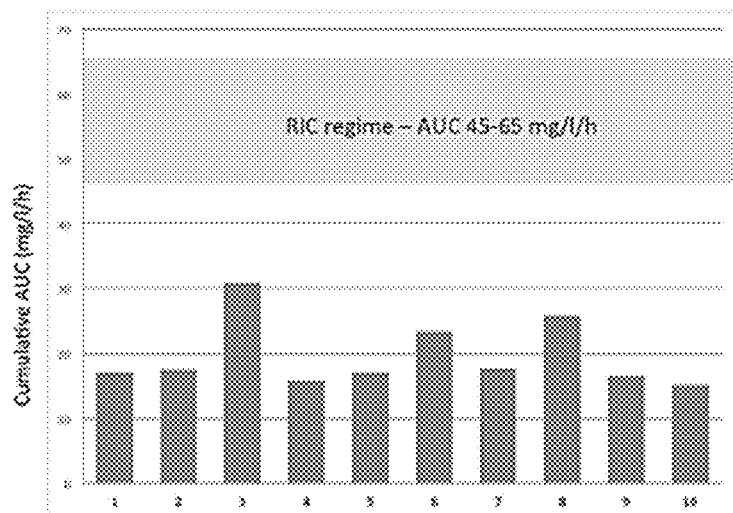
FIG. 19A is a table showing the results of a phase I/II, non-controlled, open-label, non-randomised, single-centre trial and clinical details of ten human patients treated on and off trial to assess the safety and efficacy of the EFS-ADA lentiviral vector mediated gene modification of autologous CD34+ cells from ADA-deficient individuals.
FIG. 19B is a graph representing the Busulfan exposure for patients P1-P10 from FIG. 19A. RIC regime indicates the AUC of Busulfan targeted in allogeneic transplant.

A total of 10 patients have been treated (see FIG. 19A). Of these, 6 patients have been treated as part of the formal clinical trial and 4 patient were treated off-trial on compassionate grounds. Reasons for off-trial treatment were as follows: (1) 2 patients (P1 and P2) were treated prior to the initiation of the formal clinical trial; (2) 1 patient (P4) was taken off trial because of an infected product; and (3) 1 patient (P5) did not fit the eligibility criteria. All of the off-trial patients were treated in the same way as trial patients, other than P5 who received frozen cells because of previous treatment. All patient has been on PEG-ADA prior to initiation of gene therapy.

Three patient had CD34+ cells isolated from bone marrow, in the other 7 patient, CD34+ cells were isolated from GCSF/Plerixafor mobilized peripheral blood. All patients received weight adjusted dose of Busulfan prior to reinfusion of gene corrected cells. All cells were transduced as stated above. The level of gene correction was determined by either qPCR of transduced cells cultured for 14 days and in some cases also by PCR of pooled colonies derived from the transduced cell population (FIG. 19A). In all cases, except P8, the transduction efficiency in gene corrected cells was above 0.5 VCN. No toxicities as a result of Busulfan administration were observed. The Busulfan exposure for patients P1 to P10 has been calculated and is documented in FIG. 19B.

Figure 20A:
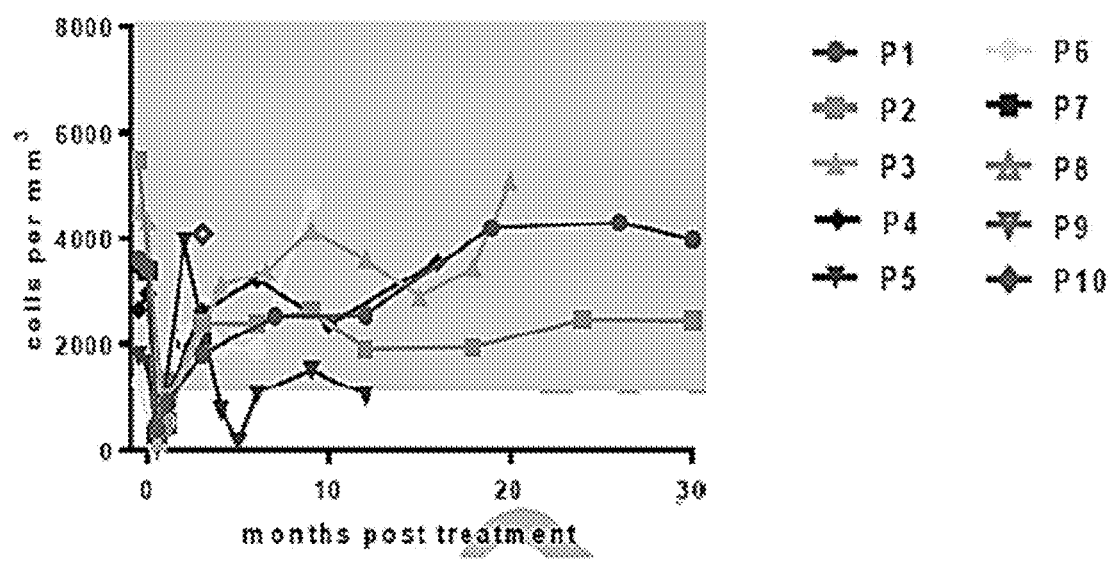
FIG. 20A is a graph of neutrophil recovery from Busulfan conditioning in human patients.
Figure 20B:
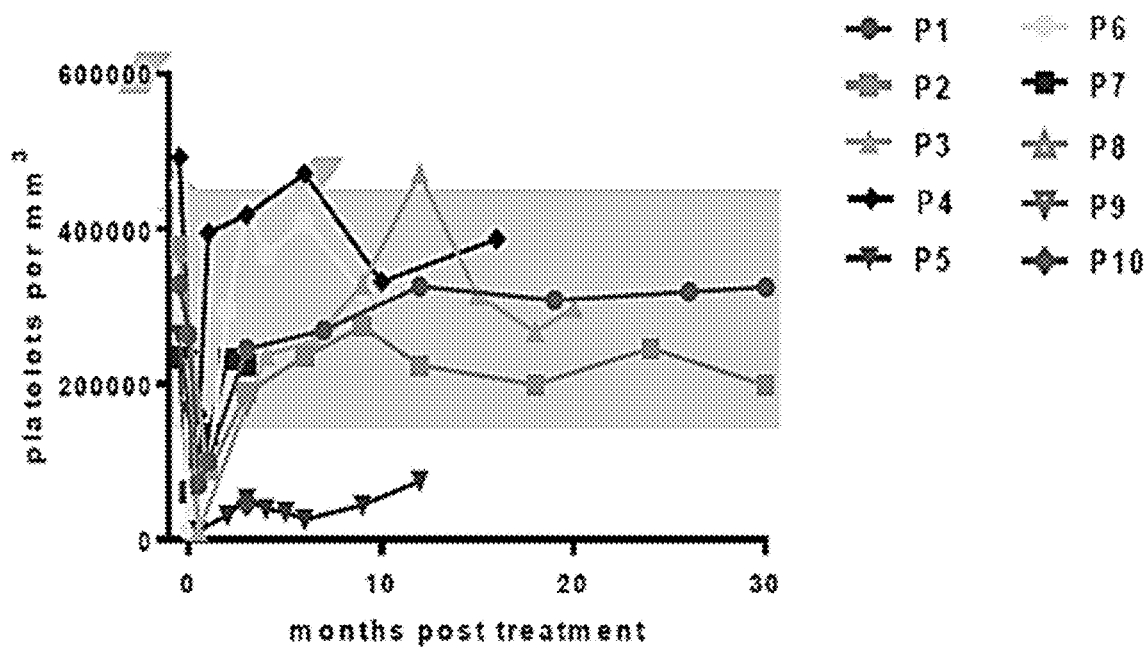
FIG. 20B is a graph of platelet recovery from Busulfan conditioning in human patients.

The time to neutrophil recovery was 21 days (range 10-46) post treatment for patients 1-5. A number of patients required variable doses of GCSF to aid neutrophil recovery. Platelet and Hb recovery was uneventful. P5 was treated off trial and received cryopreserved cells. Neutrophils recovered the normal range and platelets were above 100,000/µl. Neutrophil and platelet recovery are shown in FIGS. 20A and 20B, respectively.

In patients P1 to P6 there impressive immune recovery was observed. This included total lymphocyte counts, total CD3+ T cell counts, and T cell subsets CD4+ and CD8+ cells (FIGS. 21A-21D).

Patients P2, P4, P5 and P6 have been able to stop immunoglobulin replacement therapy and prophylactic antibiotics. They are making their own IgG and are now undergoing routine vaccinations although their response to make antibody responses to vaccines is not yet known. P7-P10 are not yet evaluable, and P1's immune recovery is not yet sufficient to allow cessation of IgG replacement. P3 was scheduled to stop IgG replacement but had an intercurrent illness and therefore continued on IgG replacement.

Vector copy number (VCN) in different cell lineages in P1 to P6 are shown in FIGS. 22A-22F. VCN is highest in T cells where all patients have a VCN of 1 or more. Gene marking is also seen at significant levels in all other lineages with some patients P3, P5, P6 having high level marking greater than 0.1 in all lineages.

Figure 23:
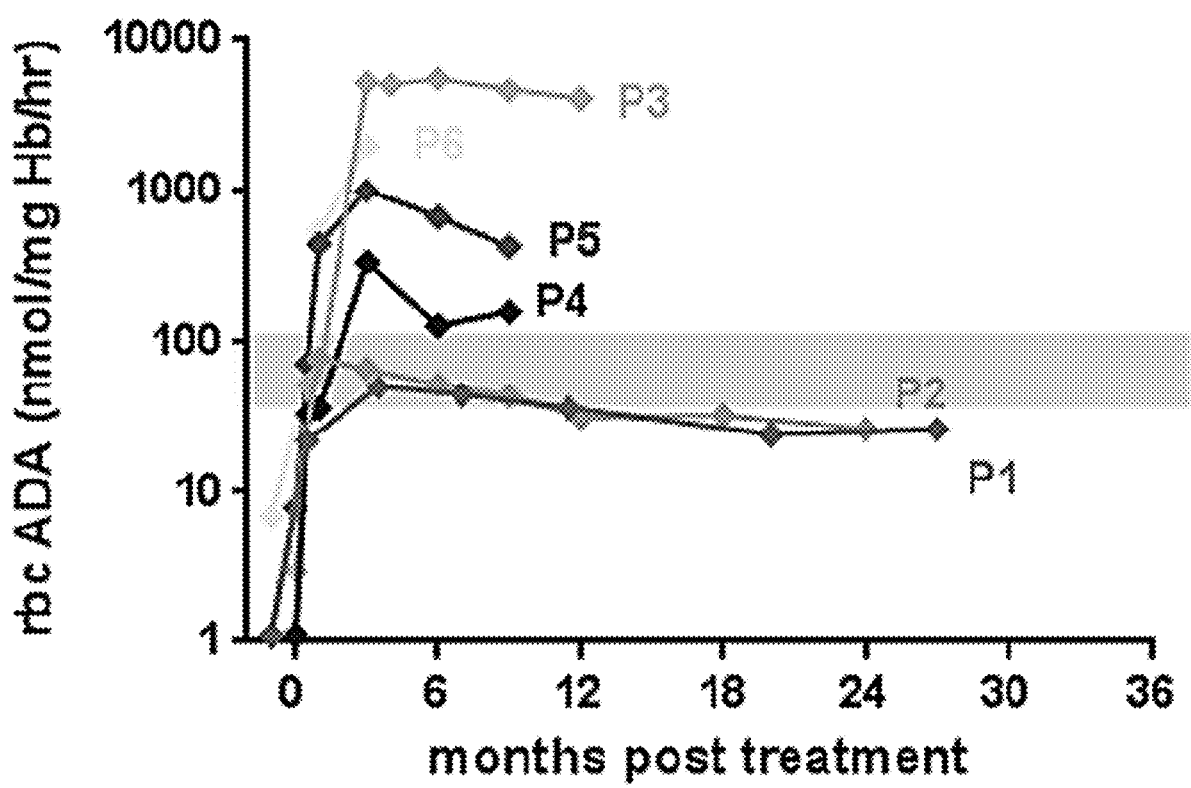
FIG. 23 is a graph representing the observation of sustained metabolic recovery of ADA levels following gene therapy with the EFS-ADA lentiviral vector in human patients.
Figure 24A:
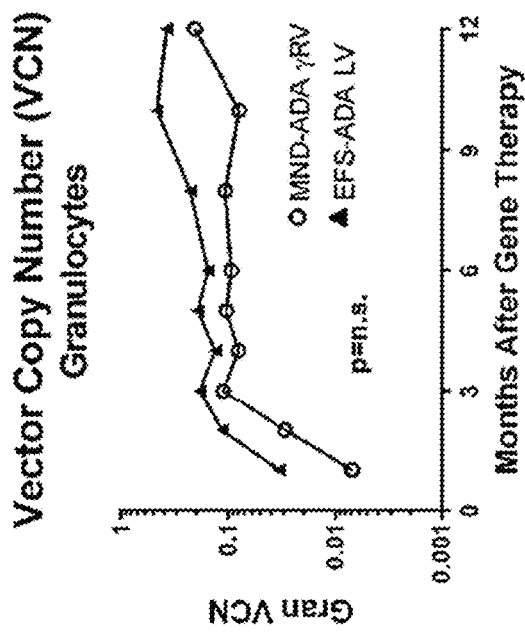
FIG. 24A is a graph of VCN in PBMCs from clinical trial data comparing the MND-ADA gRV vector with the EFS-ADA LV vector.
Figure 24B:
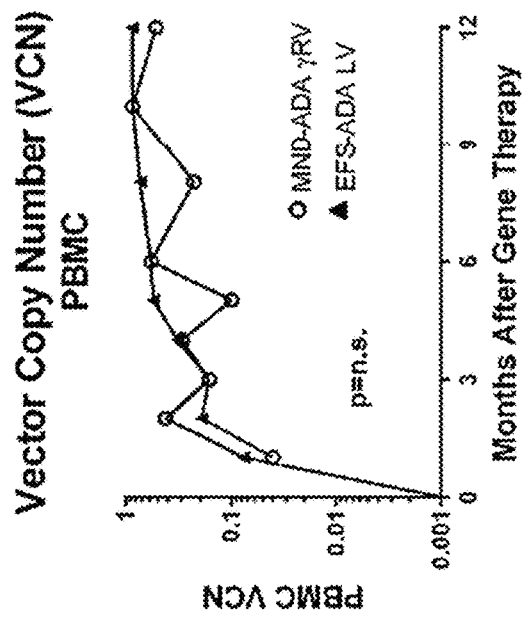
FIG. 24B is a graph of VCN in granulocytes from clinical trial data comparing the MND-ADA gRV vector with the EFS-ADA LV vector.
Figure 24C:
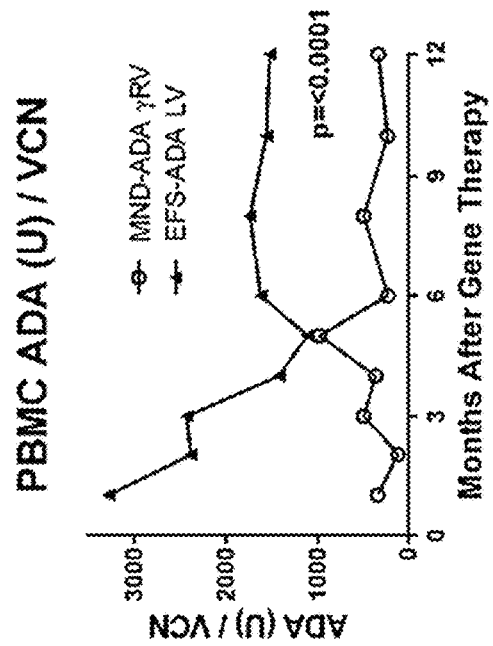
FIG. 24C is a graph depicting the expression of ADA in EFS-ADA LV treated patients, comparted to MND-ADA gRV treated patients.
Figure 24D:
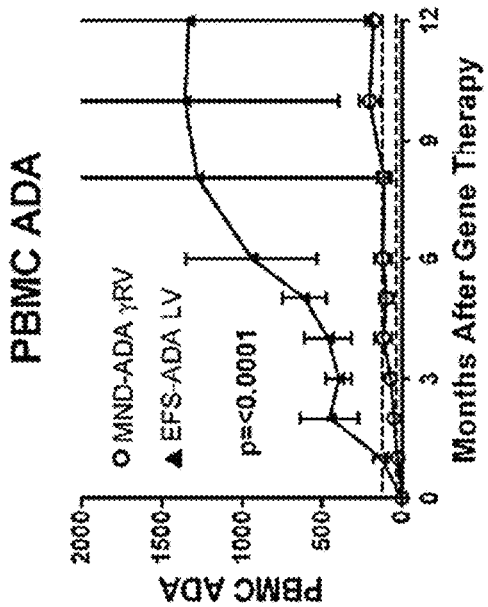
FIG. 24D is a graph depicting the activity of ADA in EFS-ADA LV treated patients, comparted to MND-ADA gRV treated patients.

Regarding metabolic recovery post-gene therapy, all patients are off PEG-ADA ERT. All show levels of dATP (which is one of the major toxic metabolites that accumulates in ADA deficiency) that are in the range that would be seen after a successful bone marrow transplant. Red blood cell (RBC) ADA levels were also measured (see FIG. 23). Prior to gene therapy, RBC ADA activity was low because PEG ADA only acts exogenously. Following gene therapy, the transduction of erythroid progenitors led to peripheral red blood cells that carry ADA. In the 6 patients in FIG. 23, the RBC level is either in the near normal range or at levels higher than the normal range. Despite in some patients the RBC ADA activity being 100 times or more greater than the normal range, no adverse effect on red blood cell numbers, haemoglobin levels or on other RBC parameters was observed.

No persistent T cell expansions linked to the GT was observed. Although P3 had a V-beta 13.1 T cell expansion, this was causally related to a primary CMV infection. This resolved with resolution of infection. P3 has also had a gamma delta T cell expansion which coincided with a primary EBV viremia but which subsequently resolved. LAM-PCR studies do not show any evidence for clonal expansion. Indeed, vector integration analysis in P3 demonstrated a highly polyclonal profile in T cells and also in the gamma delta expansion.

In addition, both expression of ADA and activity of ADA in PBMCs was strikingly increased (over 20 times in cases; $p<0.0001$) in human patients treated with GT using the EFS-ADA LV comparted to human patients treated with the MND-ADA-gammaRV construct. This significant change in ADA expression and activity, normalised for VCN, was sustained over a period of at least one year in human patients. This highly surprising and significant improvement seen when using the EFS-ADA LV rather than the MND-ADA-gammaRV construct, would not have been predicted (see FIGS. 24A-24D).

In summary, during the course of the clinical trial, no suspected unexpected serious adverse reactions occurred. All patients are alive and have remained off enzyme replacement therapy. All patients tolerated Busulfan conditioning without any significant toxicity. P1 to P6 have been evaluated and showed significant T cell recovery following gene therapy. Four of the six evaluable patients have stopped IgG replacement. All patients remain metabolically detoxified and there has been no evidence of persistent T cell clonal expansion. A highly significant and surprising sustained increase in both ADA expression and activity was observed when the LV construct was used in GT clinical trials.

REFERENCES

Adams, A. and Harkness, R. A. (1976) "Adenosine deaminase activity in thymus and other human tissues" *Clin. Exp. Immunol.* 26, 647-649

Altschul et al. (1990) "Basic local alignment search tool" *J Mol BIol* 215:403-410

Altschul et al. (1993) "A protein alignment scoring system sensitive at all evolutionary distances" *J Mol Evol* 36:290-300

Antoine, C (2003) "Long-term survival and transplantation of haemopoietic stem cells for immunodeficiencies: report of the European experience 1968-99" *Lancet* 361, 553-560.

Ariga et al. (2001) "T-cell lines from 2 patients with adenosine deaminase (ADA) deficiency showed the restoration of ADA activity resulted from the reversion of an inherited mutation" *Blood* 97, 2896-2899.

Aiuti et al. (2009)"Gene therapy for immunodeficiency due to adenosine deaminase deficiency" *N Engl J Med.* 360: 447-458

Aiuti et al. (2007) "Multilineage hematopoietic reconstitution without clonal selection in ADA-SCID patients treated with stem cell gene therapy" *J Clin Invest.* 117: 2233-2240

Apasov et al. (2001) "Adenosine deaminase deficiency increases thymic apoptosis and causes defective T cell receptor signalling" *J Clin Invest* 108:131-141

Arredondo-Vega, F. X. et al. (1998) "Adenosine deaminase deficiency: genotype-phenotype correlations based on expressed activity of 29 mutant alleles" *Am. J. Hum. Genet.* 63, 1049-1059

Bartelink et al. (2012) "Body weight-dependent pharmacokinetics of busulfan in paediatric haematopoietic stem cell transplantation patients: towards individualized dosing" *Clin Pharmacokinet.* 51:331-45

Benveniste, P. and Cohen, A (1995) "p53 expression is required for thymocyte apoptosis induced by adenosine deaminase deficiency" *Proc. Natl. Acad. Sci. U.S.A.* 92, 8373-8377.

Benveniste et al. (1995) "Interference with thymocyte differentiation by an inhibitor of S-adenosylhomocysteine hydrolase" *J. Immunol.* 155, 536-544.

Blackburn et al. (1998) "Adenosine deaminase-deficient mice generated using a two-stage genetic engineering strategy exhibit a combined immunodeficiency" *J Biol Chem.* 273:5093-5100

Blaese et al. "T lymphocyte-directed gene therapy for ADA-SCID: initial trial results after 4 years" *Science* 270:475-480

Bollinger et al. (1996) "Brief report: hepatic dysfunction as a complication of adenosine deaminase deficiency" *N. Engl. J. Med.* 334, 1367-1371.

Booth et al. (2006) "Management options for adenosine deaminase deficiency; proceedings of the EBMT satellite workshop" *Clin Immunol.* 123:139-147.

Bordignon (1995) "Gene therapy in peripheral blood lymphocytes and bone marrow for ADA-immunodeficient patients" *Science* 270, 470-475.

Borkowsky et al. (1980) "Adenosine deaminase deficiency without immunodeficiency: clinical and metabolic studies" *Pediatr. Res.* 14, 885-889.

Bortug et al. (2010) "Stem-cell gene therapy for the Wiskott-Aldrich syndrome" *N Engl J Med.* 363:1918-1927

Candotti et al. (2009) "Gene therapy for adenosine deaminase-deficient severe combined immune deficiency: clinical comparison of retroviral vectors and treatment plans" *Blood* 120:3635-3646

Carson et al. (1977) "Lymphospecific toxicity in adenosine deaminase deficiency and purine nucleoside phosphorylase deficiency: possible role of nucleoside kinase(s)" *Proc. Natl. Acad. Sci. U. S. A* 74, 5677-5681

Cederbaum et al. (1976) "The chondro-osseous dysplasia of adenosine deaminase deficiency with severe combined immunodeficiency" *J. Pediatr.* 89, 737-742

Chaffee et al. (1992) "IgG antibody response to polyethylene glycol-modified adenosine deaminase in patients with adenosine deaminase deficiency" *J. Clin. Invest.* 89, 1643-1651

Chan et al. (2005) "Long-term efficacy of enzyme replacement therapy for adenosine deaminase (ADA)-deficient Severe Combined Immunodeficiency (SCID)" *Clin. Immunol.* 117, 133-143

Daddona et al. (1983) "Adenosine deaminase deficiency with normal function" *J. Clin. Invest.* 483-492

Devereux et al. (1984) "A comprehensive set of sequence analysis programs for the VAX" *Nucleic Acids Res.* 12:387-395

Dinjens et al. (1989) "Distribution of adenosine deaminas complexing protein (ADCP) in human tissues" *J. Histochem. Cytochem.* 37, 1869-1875

Dong et al. (1997) "Determination of adenosine deaminase binding domain on CD26 and its immunoregulatory effect on T cell activation" *J. Immunol.* 159, 6070-6076.

Dooley et al. (1987) "First trimester diagnosis of adenosine deaminase deficiency" *Prenat. Diagn.* 7, 561-565.

Dull et al. (1998) "A third-generation lentivirus vector with a conditional packaging system" *J Virol* 72:8463-8471.

Fischer et al. (1997) "Naturally occurring primary deficiencies of the immune system" *Annu. Rev. Immunol.* 15, 93-124.

Fox et al. (1984) "Ta1, a novel 105 KD human T cell activation antigen defined by a monoclonal antibody" *J. Immunol.* 133, 1250-1256

Gaspar et al. (2006) "Successful reconstitution of immunity in ADA-SCID by stem cell gene therapy following cessation of PEG-ADA and use of mild preconditioning" *Mol Ther* 14: 505-513

Gaspar et al. (2009) "How I treat ADA deficiency" *Blood* 114:3524-3532

Gaspar et al. (2011) "Hematopoietic stem cell gene therapy for adenosine deaminase-deficient severe combined immunodeficiency leads to long-term immunological recovery and metabolic correction" *Sci Transl Med.* 3:97ra80

Giblett et al. (1972). "Adenosinedeaminase deficiency in two patients with severely impaired cellular immunity" *Lancet* 2, 1067-1069.

Hacein-Bey-Abina et al. (2008) "Insertional oncogenesis in 4 patients after retrovirus-mediated gene therapy of SCID-X1" *J Clin Invest.* 118:3132-3142

Hacein-Bey-Abina et al. "LMO2-associated clonal T cell proliferation in two patients after gene therapy for SCID-X1" *Science* 302:415-419

Henikoff and Henikoff (1992) "Amino acid substitution matrices from protein blocks" *PNAS* 15:10915-9

Hershfield et al. (1979) "In vivo inactivation of erythrocyte S-adenosylhomocysteine hydrolase by 2'-deoxyadenosine in adenosine deaminase-deficient patients" *J. Clin. Invest.* 63, 807-811.

Hershfield et al. (1998) "Adenosine deaminase deficiency: clinical expression, molecular basis, and therapy" *Semin Hematol* 35:291-298

Hershfield M, and Mitchell B. (1995) "Immunodeficiency disease caused by adenosine deaminase deficiency and purine nucleoside phosphorylase deficiency" *Metabolic basis of inherited disease.* New York: McGraw-Hill Hershfield, M. S. (2004) "Combined immune deficiencies due to purine enzyme defects. In Immunologic Disorders in Infants and Children" E (Philadelphia: W.B. Saunders), pp. 480-504.

Hirschhorn et al. (1980) "Amerioration of neurologic abnormalities after "enzyme replacement" in adenosine deaminase deficiency" *N. Engl. J. Med.* 303, 377-380.

Hirschhorn, R. (1993) "Overview of biochemical abnormalities and molecular genetics of adenosine deaminase deficiency" *Pediatr. Res.* 33, S35-41.

Hirschhorn et al. (1996) "Spontaneous in vivo reversion to normal of an inherited mutation in a patient with adenosine deaminase deficiency" *Nat. Genet.* 13, 290-295.

Hoogerbrugge et al. (1996). "Bone marrow gene transfer in three patients with adenosine deaminase deficiency" *Gene Therapy* 179-183.

Howe et al. (2008) "Insertional mutagenesis combined with acquired somatic mutations causes leukemogenesis following gene therapy of SCID-X1 patients" *J Clin Invest.* 118:3143-3150

Husain (2007) "Burkitt's lymphoma in a patient with adenosine deaminase deficiency-severe combined immunodeficiency treated with polyethylene glycol-adenosine deaminase" *J. Pediatr* 151, 93-95.

Ingolia, D. E et al. (1986) Molecular cloning of the murine adenosine deaminase gene from a genetically enriched source: identification and characterization of the promoter region. *Mol. Cell Biol.* 6, 4458-4466.

Jhanwar et al. (1989) "Localization of human adenosine deaminase (ADA) gene sequences to the q12----q13.11 region of chromosome 20 by in situ hybridization" *Cytogenet. Cell Genet.* 50, 168-171.

Kadonaga et al. (1987) "Isolation of cDNA encoding transcription factor Spl and functional analysis of the DNA binding domain" *Cell* 51, 1079-1090

Karlin and Altschul (1993) "Applications and statistics for multiple high-scoring segments in molecular sequences" *PNAS* 15:5873-7

Kaufman et al. (2005) "Cerebral lymphoma in an adenosine deaminase-deficient patient with severe combined immunodeficiency receiving polyethylene glycol-conjugated adenosine Deaminase" *Pediatrics* 116, e876-e879.

Kohn (1998) "T lymphocytes with a normal ADA gene accumulate after transplantation of transduced autologous umbilical cord blood CD34+ cells in ADA-deficient SCID neonates" *Nat. Med.* 4, 775-780.

Lee, N et al. (1984) "Mechanisms of deoxyadenosine toxicity in human lymphoid cells in vitro: relevance to the therapeutic use of inhibitors of adenosine deaminase" *Br. J. Haematol.* 56, 107-119.

Macchi et al. (1995) "Mutations of Jak-3 gene in patients with autosomal severe combined immune deficiency (SCID)" *Nature* 377, 65-68.

Marwaha et al. (2000) "Extreme thrombocytosis in response to PEG-ADA: early therapeutic and risk indicator" *Clin. Pediatr.* (Phila) 39, 183-186.

Markert et al. (1988). "Adenosine deaminase (ADA) deficiency due to deletion of the ADA gene promoter and first exon by homologous recombination between two Alu elements" *J. Clin. Invest.* 81, 1323-1327.

Migchielson et al. (1996) "Adenosine-deaminase-deficient mice die perinatally and exhibit liver-cell degeneration, atelectasis and small intestinal cell death" *Nat. Genet.* 10, 279-287

Mohandas et al. (1980) "Regional mapping of ADA and ITP on human chromosome 20: cytogenetic and somatic cell studies in an X/20 translocation. Cytogenet" *Cell Genet.* 26, 28-35.

Morgan et al. (1987) "Heterogeneity of biochemical, clinical and immunological parameters in severe combined immunodeficiency due to adenosine deaminase deficiency" *Clin. Exp. Immunol.* 70, 491-499

Morrison et al. (1993). A marker for neoplastic progression of human melanocytes is a cell surface ectopeptidase. *J. Exp. Med.* 177, 1135-1143.

Moshous, D et al. (2001) "Artemis, a novel DNA double-strand break repair/V(D)J recombination protein, is mutated in human severe combined immune deficiency" *Cell* 105, 177-186.

Noguchi et al. (1993) "Interleukin-2 receptor gamma chain mutation results in X-linked severe combined immunodeficiency in humans" *Cell* 73:147-57

Ott et al. (2006) "Correction of X-linked chronic granulomatous disease by gene therapy, augmented by insertional activation of MDS1-EVI1, PRDM16 or SETBP1" *Nat Med.* 12:401-409

Ozsahin et al. (1997) "Adenosine deaminase deficiency in adults" *Blood* 89, 2849-2855.

Petersen et al. (1987) "New assignment of the adenosine deaminase gene locus to chromosome 20q13×11 by study of a patient with interstitial deletion 20q" *J. Med. Genet.* 24, 93-96.

Philip et al. (1980) "Regional assignment of the ADA locus on 20q13.2 leads to qter by gene dosage studies." *Cytogenet. Cell Genet.* 27, 187-189

Polmar, S. H. (1978). "Enzyme replacement and other biochemical approaches to the therapy of adenosine deaminase deficiency" *Ciba. Found. Symp.* 213-230.

Puel et al. (1998) "Defective IL7R expression in T(−)B(+) NK(+) severe combined immunodeficiency" *Nat. Genet.* 20, 394-397.

Ratech et al. (1985) "Pathologic findings in adenosine deaminase-deficient severe combined immunodeficiency. I. Kidney, adrenal, and chondro-osseous tissue alterations" *Am. J. Pathol.* 120, 157-169.

Revy et al. (2006). "Cernunnos-XLF, a recently identified nonhomologous end-joining factor required for the development of the immune system" *Curr. Opin. Allergy Clin. Immunol* 6, 416-420.

Richard, E et al. (2000) "The binding site of human adenosine deaminase for CD26/Dipeptidyl peptidase IV: the Arg142Gln mutation impairs binding to cd26 but does not cause immune deficiency" *J. Exp. Med.* 192, 1223-1236.

Rieux-Laucat et al. (2006) "Inherited and somatic CD3zeta mutations in a patient with T-cell deficiency" *N. Engl. J. Med.* 354, 1913-1921.

Sanchez et al. (2007) "Carrier frequency of a nonsense mutation in the adenosine deaminase (ADA) gene implies a high incidence of ADA-deficient severe combined immunodeficiency (SCID) in Somalia and a single, common haplotype indicates common ancestry" *Ann. Hum. Genet.* 71, 336-347.

Schambach et al. (2006) "Woodchuck hepatitis virus posttranscriptional regulatory element deleted from X protein and promoter sequences enhances retroviral vector titer and expression" *Gene Ther* 13:641-645

Schambach (2000) "Context dependence of different modules for posttranscriptional enhancement of gene expression from retroviral vectors" *Mol Ther* 2: 435-445.

Schrader et al. (1990) Characterization of the adenosine deaminase-adenosine deaminase complexing protein binding reaction. *J. Biol. Chem.* 265, 19312-19318.

Shultz et al. (2005) "Human lymphoid and myeloid cell development in NOD/LtSz-scid IL2R gamma null mice engrafted with mobilized human hemopoietic stem cells" *J Immunol* 174:6477-6489.

SenGupta et al. (1985) "A flow cytometric method for the detection of adenosine deaminase in mononuclear cells" *J. Immunol. Methods* 80, 155-162.

Shovlin et al. (1994) "Adult onset immunodeficiency caused by inherited adenosine deaminase deficiency" *J. Immunol.* 153, 2331-2339.

Soudais, C et al. (1993) "Independent mutations of the human CD3-epsilon gene resulting in a T cell receptor/CD3 complex immunodeficiency" *Nat. Genet.* 3, 77-81.

Stein et al. (2010) "Genomic instability and myelodysplasia with monosomy 7 consequent to EVI1 activation after gene therapy for chronic granulomatous disease" *Nat Med.* 16:198-204

Stephan et al. (1996) "A typical X-linked severe combined immunodeficiency due to possible spontaneous reversion of the genetic defect in T cells" *N. Engl. J. Med.* 335, 1563-1567.

Takeda et al. (1991) "Effects of deoxyadenosine on ribonucleotide reductase in adenosine deaminase-deficient lymphocytes" *J. Inherit. Metab. Dis.* 14, 87-95.

Tanaka et al. (1996). "Sensorineural deafness in siblings with adenosine deaminase deficiency" *Brain Dev.* 18, 304-306.

Thrasher et al. (2005) "Failure of SCID-X1 gene therapy in older patients" *Blood* 105, 4255-4257.

Tischfield et al. (1974) "Assignment of a gene for adenosine deaminase to human chromosome 20" *Hum. Hered.* 24, 1-11.

Titman et al. (2008). Cognitive and behavioural abnormalities in children after hematopoietic stem cell transplantation for severe congenital immunodeficiencies. *Blood* 112, 3907-3913.

Trotta, P. P. (1982) "Identification of a membrane adenosine deaminase binding protein from human placenta" *Biochemistry* 21, 4014-4023.

Van der Weyden, M. B. and Kelley, W. N. (1976) "Human adenosine deaminase. Distribution and properties" *J. Biol. Chem.* 251, 5448-5456.

van, L. J (2007) "Transfer of autologous gene-modified T cells in HIV-infected patients with advanced immunodeficiency and drug-resistant virus" *Mol. Ther* 15:1024-1033.

Valerio et al. (1983) "Isolation of cDNA clones for human adenosine deaminase" *Gene* 25, 231-240

Zychlinski et al. (2008) "Physiological promoters reduce the genotoxic risk of integrating gene vectors" *Mol Ther* 16:718-25

```
Sequence Information
the sequence of human codon optimised ADA cDNA sequence.
                                                       SEQ ID NO: 1
ATGGCCCAGACCCCCGCCTTCGACAAGCCCAAGGTGGAGCTGCACGTGCACCTGGACGGCAGCAT

CAAGCCTGAGACCATCCTCTACTACGGCAGGCGGAGAGGCATCGCCCTGCCCGCCAACACAGCGA

GGGCCTGCTGAACGTGATCGGCATGGACAAGCCCCTGACCCTGCCCGACTTCCTGGCCAAGTTCGA

CTACTACATGCCCGCCATCGCCGGCTGCCGGGAGGCCATCAAGCGGATCGCCTACGAGTCGTGGA

GATGAAGGCCAAGGAAGGCGTGGTGTACGTGGAAGTGCGGTACAGCCCCCACCTGCTGGCCAACA

GCAAGGTGGAACC\CATCCCCTGGAACCAGGCCGAGGGCGACCTGACCCCCGACGAGTGGTGGCT

CTGGTCGGCCAGGGGCTGCAGGAAGGCGAGCGGGACTTCGGCGTGAAGGCCCGGTCCATCCTGTG

CTGCATGCGGCACCAGCCCAACTGGTCCCCCAAGGTGGTGGAGCTGTGCAAGAGTACCAGCAGCA

GACCGTGGTGGCCATCGACCTGGCCGGCGATGAGACCATCCCCGGCTCCAGCCTGCTCCCCGGCCA

CGTGCAGGCCTACCAGGAAGCCGTCAAGAGCGGCATCCACCGGACCGTGACGCCGGCGAAGTGGG

CAGCGCCGAGGTGGTGAAAGAAGCCGTGGACATCCTGAAAACCGAGCGGCTGGGCCACGGCTACC

ACACCCTGGAAGATCAGGCCCTGTACAACCGGCTGCGGCAAGAAAAATGCACTTCGAGATCTGCC

CCTGGTCCAGCTACCTGACCGGCGCCTGGAAGCCCGACACCGAGCACGCCGTGATCCGGCTGAAG

AACGACCAGGCCAACTACAGCCTGAACACCGACGACCCCCTGACTTCAAGAGCACCCTGGACACC

GACTACCAGATGACCAAGCGGGACATGGGCTTCACCGAGGAAGAGTTCAAGCGGCTGAACATCAA

CGCCGCCAAGAGCAGCTTCCTGCCCGAGGACGAGAAGCGGAGCTGCTGGACCTGCTGTACAAGGC

CTACGGCATGCCCCCTAGCGCCAGCGCCGGACAGAACCTG the sequence of the LV EFS ADA lentiviral vector from the
junction marker.
                                                       SEQ ID NO: 2
ACGCGCCCTGTAGCGGCGCATTAAGCGCGGCGGGTGTGGTGGTTACGCGCAGCGTGACCGCTACA

CTTGCCAGCGCCCTAGCGCCCGCTCCTTTCGCTTTCTTCCCTTCCTTTCTCGCCACGTTCGCGGCTTT

CCCCGTCAAGCTCTAAATCGGGGGCTCCCTTTAGGGTTCCGATTTAGTGCTTTACGGCACCTCGAC
```

-continued

```
CCCAAAAAACTTGATTAGGGTGATGGTTCACGTAGTGGGCCATCGCCCTGATAGAGGTTTTTCGCC
CTTTGACGTTGGAGTCCACGTTCTTTAATAGTGGACTCTTGTTCCAAACTGGAACAACACTCAACC
CTATCTCGGTCTATTCTTTTGATTTATAAGGGATTTTGCCGATTTCGGCCATTGGTTAAAAATGAG
CTGATTTAACAAAAATTTAACGCGAATTTTAACAAAATATTAACGCTTACAATTTAGGTGGCACTT
TTCGGGGAAATGTGCGCGGAACCCCTATTTGTTTATTTTTCTAATACATTCAAATATGTATCCGCTC
ATGAGACAATAACCCTGATAAATGCTTCAATAATAGCACCTAGATCAAGAGACAGGATGAGGATC
GTTTCGCATGATTGAACAAGATGGATTGCACGCAGGTTCCCGGCCGCTTGGGTGGAGAGGCTATTC
GGCTATGACTGGGCACAACAGACAATCGGCTGCTCTGATGCCGCCGTGTTCCGGCTGTCAGCGCAG
GGGCGCCCGGTTCTTTTTGTCAAGACCGACCTGTCGGTGCCCTGAATGAACTGCAAGACGAGGCAG
CGCGGCTATCGTGGCTGGCCACGACGGGCGTTCCTTGCGCAGCTGTGCTCGACGTTGTCACTGAAG
CGGGAAGGGACTGGCTGCTATTGGGCGAATGCCGGGGCAGGATCTCCTGTCATCTCACCTTGCTCC
TGCCGAGAAAGTATCCATCATGGCTGATGCAATGCGGCGGCTGCATACGCTTGATCCGGCTACCTG
CCCATTCGACCACCAAGCGAAACACGCATCGAGCGAGCACGTACTCGGATGGAAGCCGGTCTTGT
CGATCAGGATGATCTGGACGAAGAGCATCAGGGGCTCGCGCCAGCCGAACTGTTCGCCAGGCTCA
AGGCGAGCATGCCCGACGGCGGGATCTCGTCGTGACCCATGGCGATGCCTGCTTGCCGAATATCAT
GGTGGAAAATGGCCGCTTTTCTGGATTCATCGACTGTGGCCGGCTGGGTGTGGCGGACCGCTATCA
GGACATAGCGTTGGCTCCCGTGATATTGCTGAAGAGCTTGGCGGCGAATGGGCTGACCGCTTCCTC
GTGCTTTACGGTATCGCCGCTCCCGATTCGCAGCGCATCGCCTTCTATCGCCTTCTTGACGAGTTCT
TCTGAATTATAACGCTTACAATTTCCTGATGCGGTATTTTCTCCTTACGCATCTGTGCGGTATTTCA
CACCGCATCAGGTGGCACTTTTCGGGGAAATGTGCGCGGAACCCCTATTTGTTTATTTTTCTAAATA
CATCAAATATGTATCCGCTCATGACCAAAATCCCTTAACGTGAGTTTTCGTTCCACTGAGCGTCAG
ACCCCGTAGAAAAGATCAAAGGATCTTCTTGAGATCCTTTTTTTCTGCGCGTAATCTGCTGCTTCAA
ACAAAAAAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTTCTTCTAGTGTAGCCGTGTTAGGCC
ACCACTTCAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACGGATAAGGCGC
AGCGGTCGGGCTGAACGGGGGGTCGTGCACACAGCCCAGCTTGGAGCGAACGACCTACACCGAA
CTGAGATACCTACAGCGTGAGCTATGAGAAAGCGCCACGCTTCCCGAAGGAGAAAGGCGGACAG
GTATCCGGTAAGCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCATTTTTGTGATGCTCGTC
AGGGGGGCGGAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATTACCGCCTTTG
AGTGAGCTGATACCGCTCCCGCAGCCGAACGACCGAGCGCAGCGAGTCAGTGAGCGAGGAAGCG
GAAGAGCGCCCAATACGCAAACCGCCTCTCCCCGCGCGTTGGCCGATTCATTAATGCAGCTGGCAC
GACAGGTTTCCCGACGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGTGAGCGGATAA
CAATTTCACACGGAAACAGCTATGACCATGATTACGCCAAGCGCGCAATTAACCCTCACTAAAGG
GAACAAAAGCTGGAGCTGCAAGCTTGGCCATTGCATACGTTGTATCCATATCATAATATGTACATT
TATATTGCTCATGTCCAACATTACCGCCATGTTGACATTGATTATTGACTAGTTATTAATAGTAATC
AATTACGGGGTCATTAGTTCATAGCCCATATATGGAGTTCCGCGTTACATAACTTACGGTAAATGG
CCGCCTGGCTGACCGCCCAACGACCCCCGCCCATTGACGTCAATAATGACGTATGTTCCCATAGTA
```

-continued

```
ACGCCAATAGGGACTTTCCATTGACGTCAATGGGTGGAGTATTTACGGTAAACTGCCCACTTGCAG

TACATCAAGTGTATCATATGCCAAGTACGCCCCCTATTGACGTCAATGACGGTAAATGGCCCGCCT

GGCATTATGCCCAGTACATGACCTTATGGGACTTTCCTACTTGGCAGTACATCTACGATTAGTCATC

GCTATTACCATGGTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACAAAATCAACGGGACT

TTCCAAAATGTCGTAACAACTCCGCCCCATTGACGCAAATGGGCGGTAGGCGTGTACGGTGGGAG

GTCTATATAAGCAGAGCTCGTTTAGTGAACCGGGGTCTCTCTGGTTAACCAGATCTGAGCCTGGGA

GCTCTCTGGCTAACTAGGGAACCCACTGCTTAAGCCTCAATAAAGCTTGCCTTGAGTGCTTCAAGT

AGTGTGTGCCCGTCTGTTGTGTGACTCTGGTAACTAGAGATCCTCAGACCCTTTTAGTCAGTGTGG

AAAATCTCTAGCAGTGGCGCCCGAACAGGGACTTGAAAGCGAAAGGGAAACCAGAGGAGCTCTCT

CGACGCAGGACTCGGCTTGCTGAAGCGCGCACGGCAAGGGCGAGGGGCGGCGACTGGTGAGTAC

GCCAAAAATTTTGACTAGCGGAGGCTAGAAGGAGAGAGATGGGTGCGAGAGCGTCAGTATTAAGC

GGGGGAGAATTAGATCGCGATGGGAAAAAATTCGGTAAGGCCAGGGGGAAAGAAAAAATATAAA

TTAAAACATATAGTATGGGCAAGCAGGGAGCTAGAACGATTCGCAGTTAATCCTGGCCTGTTAGA

AACATCAGAAGGCTGTAGACAAATACTGGGACAGTACAACCATCCCTTCAGACAGGATCAGAAGA

ACTTAGATCATTATATAATACAGTAGCAACCCTCTATTGTGTGCATCAAAGGATAGAGATAAAAGA

CACCAAGGAAGCTTTAGACAAGATAGAGGAGAGCAAAACAAAGTAAGACCACCGCACAGCAAG

CGGCCGCTGATCTTCAGACCTGGAGGAGGAGATATGAGGGACAATTGGAGAAGTGAATTATATAA

ATATAAAGTAGTAAAAATTGAACCATTAGAGTAGCACCCACCAAGGCAAAGAGAAGAGTGGTGC

AGAGAGAAAAAGAGCAGTGGGAATAGGAGCTTTGTTCCTTGGGTTCTTGGGAGCAGCAGGAAGC

ACTATGGGCGCAGCGTCAATGACGCTACGGTACAGGCCAGACAATTATTGTCTGGTATAGTGCAG

CAGCAGAACAATTTGCTGAGGGCTATTGAGGCGCAACAGCATCTGTTGCAACTCACAGTCTGGGG

CATCAAGCAGCTCCAGGCAAGAACCTGGCTGTGGAAAGATACCTAAAGGATCAACAGCTCCTGGG

GATTTGGGGTTGCTCTGGAAAACTCATTTGCACCACTGCTGTGCCTTGGAATGCTAGTTGGAGTAA

TAAATCTCTGGAACAGATTGGAATCACACGACCTGGATGGAGTGGGACAGAGAAATTAACAATTA

CACAAGCTTAATACACTCCTTAATTGAAGAATCGCAAAACCAGCAAGAAAAGAATGAACAAGAAT

TATTGGAATTAGATAATGGGCAAGTTTGTGGAATTGGTTTAACATAACAAATTGGCTGTGGTATAT

AAAATTATTCATAATGATAGTAGGAGGCTTGGTAGGTTTAAGAATAGTTTTTGCTGTACTTTCTATA

GTGAATAGAGTTAGGCAGGGATATTCACCATTATCGTTTCAGACCCACCTCCCAACCCCGAGGGGA

CCCGACAGGCCCGAAGGAATAGAAGAAGAAGGGGAGAGAGAGACAGAGACAGATCCATTCGATT

AGTGAACGGATCTCGACGGTATCGGTTAACTTTTAAAAGAAAAGGGGGATTGGGGGTACAGTG

CAGGGGAAAGAATAGTAGACATAATAGCAAAGACATACAAACTAAAGAATTACAAAAACAAATT

ACAAAATTCAAAATTTTATCGATTGGCTCCGGTGCCCGTCAGTGGGCAGAGCGCACATCGCCCACA

GTCCCCGAGAAGTTGGGGGAGGGGTCGCAATTGAACCGGTGCCTAGAGAAGGTGGCGCGGGGT

AAACTGGGAAAGTGATGTCGTGTACTGGCTCCGCCTTTTTCCCGAGGGTGGGGGAGAACCGTATAT

AAGTGCAGTAGTCGCCGTGAACGTCTTTTTCGCAACGGGTTTGCCGCCAGAACACAGGTGTCGTGA

CGCGGGATCCAGCGCTGCGGCCGCGCCACCATGGCCCAGACCCCGCCTTCGACAAGCCCAAGGT

GGAGCTGCACGTGCACCTGGCGGCAGCATCAAGCCTGAGACCATCCTCTACTACGGCAGGCGGAG

AGGCATCGCCCTGCCCGCCAACACAGCCGAGGGCCTGCTGAACGTGATCGGCATGGACAAGCCCC

TGACCCTGCCCGACTTCTGGCCAAGTTCGACTACTACATGCCCGCCATCGCCGGCTGCCGGGAGGC
```

-continued

```
CATCAAGCGGATCGCCTACGAGTTCGTGGAGATGAAGGCCAAGGAAGGCGTGGTGTACGTGGAAG
TGCGGTACAGCCCCACCTGCTGGCCAACAGCAAGGTGGAACCCATCCCCTGGAACCAGGCCGAGG
GCGACCTGACCCCCGACGAGGTGGTGGCTCTGGTCGGCCAGGGGCTGCAGGAAGGCGAGCGGGAC
TTCGGCGTGAGGCCCGGTCCATCCTGTGCTGCATGCGGCACCAGCCCAACTGGTCCCCCAAGGTGG
TGGAGCTGTGCAAGAAGTACCAGCAGCAGACCGTGGTGGCCATCGACCTGGCCGGCGATGAGACC
ATCCCCGCTCCAGCCTGCTCCCCGGCCACGTGCAGGCCTACCAGGAAGCCGTCAAGAGCGGCATC
CACCGGACCGTGCACGCCGGCGAAGTGGGCAGCGCCGAGGTGGTGAAAGAAGCCGTGGACATCCT
GAAACCGAGCGGCTGGGCCACGGCTACCACACCCTGGAAGATCAGGCCCTGTACAACCGGCTGCG
GCAAGAAAACATGCACTTCGAGATCTGCCCCTGGTCCAGCTACCTGACCGGCGCCTGGAAGCCCG
CACCGAGCACGCCGTGATCCGGCTGAAGAACGACCAGGCCAACTACAGCCTGAACACCGACGACC
CCCTGATCTTCAAGAGCACCCTGGACACCGACTACCAGATGACCAAGCGGGACATGGGCTTCCCG
AGGAAGAGTTCAAGCGGCTGAACATCAACGCCGCCAAGAGCAGCTTCCTGCCCGAGGACGAGAA
GCGGGAGCTGCTGGACCTGCTGTACAAGGCCTACGGCATGCCCCCTAGCGCCAGCGCCGGCAGAA
CCTGTGATGAGTCGACAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGTATTGCTTCCCG
TATGGCTTTCATTTTCTCCTCCTTGTATAAATCCTGGTTGCTGTCTCTTTATGAGGAGTTGTGGCCCG
TTGTCAGGCAACGTGGCGTGGTGTGCACTGTGTTTGCTGACGCAACCCCACTGGTTGGGCATTGC
CACCACCTGTCAGCTCCTTTCCGGGACTTTCGCTTTCCCCCTCCCTATTGCCACGGCGGAACTCATC
GCCGCCTGCCTTGCCCGCTGCTGGACAGGGGCTCGGCTGTTGGCACTGACAATTCCGTGGTGTTGT
CGGGGAAATCATCGTCCTTTCCTTGGCTGCTCGCCTGTGTTGCCACCTGGATTCTGCGCGGGACGTC
CTTCTGCTACGTCCCTTCGGCCCTCAATCCAGCGGCCTTCCTTCCCGCGGCCTGCTGCCGGCTCTGC
GGCCTCTTCCGCGTCTTCGCCTTCGCCCTCAGACGAGTCGGATCTCCCTTTGGGCCGCCTCCCCGCC
TGGAATTCGAGCTCGGTACCTTTAAGACAATGACTTACAAGGCAGCTGTAGATCTTAGCCACTTTT
TAAAAGAAAAGGGGGGACTGGAAGGGCTAATTCACTCCCAACGAAGACAAGATCTGCTTTTTGCT
TGTACTGGGTCTCTCTGGTTAGACAGATCTGAGCCTGGGAGCTCTCTGGCTAACTAGGGAACCCAC
TGCTTAAGCCTCAATAAAGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTAGCAGTAGTAGTTCATG
TCATCTATTATTCAGTATTTATAACTTGCAAAGAAATGAATATCAGAGAGTGAGAGGAACTTGTTT
ATTGCAGCTTATAATGGTTACAAATAAAGCAATAGCATCACAAATTTCACAAATAAAGCATTTTTT
CACTGCATTCTAGTTGTGGTTTGTCCAAACTCATCAATGTATCTTATCATGTCTGGCTCTAGCTATC
CCGCCCCTAACTCCGCCCATCCCGCCCCTAACTCCGCCCAGTTCCGCCCATTCTCCGCCCATGGCTG
ACTAATTTTTTTTATTTATGCAGAGGCCGAGGCCGCCTCGGCCTCTGAGCTATTCCAGAAGTAGTG
AGGAGGCTTTTTTGGAGGCCTAGGGACGTACCCAATTCGCCCTATAGTGAGTCGATTACGCGCGCT
CACTGGCCGTCGTTTTACAACGTCGTGACTGGGAAAACCCTGGCGTTACCCAACTTAATCGCCTTG
CAGCACATCCCCCTTTCGCCAGCTGGCGTAATAGCGAAGAGGCCCGCACGATCGCCCTTCCCAACA
GTTGCGCAGCCTGAATGGCGAATGGG
``` the full length elongation factor 1 alpha sequence.

SEQ ID NO: 3

```
TTAAAGCTTAAAATTCATTTATTGTAGTGAGCAAGTTTGTAATGAATACCAGCAGGTGGTGCTCAA
GCCACAGTTGTCTAAGACACTGGGTTTCACAGGAAGTTAATCTCAATCTCAGTATATGCAAGTAAA
CTGACTCATTCCTGCTTCCAGTGGGAACAATTTTTCAGTTAAATCTTGCTTCCTTGCATGTCAAGAA
TTCTCTACTGGTAAATCTTACAGGTGTCAACTTTCATTATCAGGGCATCTATTGGCCATCTATTAAA
```

-continued

```
GGCCTTACCTGTTTTTTCTGTCATCCAGCAAATCTTAGACTATTTACTTGTGTAAACATTAGATAGC
AAAGAAACTAAGGACAAAAATCTCTAGTTCAATTTAGACTTGATACCTCAGAGCACTGGCTGATG
GGAAGGCATTTTATCTAATTCAGACTCAGATGAGGGAAAACGATAACACTTCATTACAGACTTGTC
TATGGCCAATTCAAGTACCTTTGAATCTTGAGCAATACACATTGCCAGTCACTTTAAGAGGCCTTA
TCTCTTGGGCTGCTTTAACTCCTGCTTAGCATGTCCTTAAGAACACATGTCCTGGCCAGGCATGGTG
GCTCATGCCTGTAATTCCAGCACTTTAGGAGGCCGAGGCGATCACCTAAGGTCAGGAGTTTGAGAC
CAGCCTGACCAACATGGAAAAACCTCATCTCTATTAAAAACACCAAATTAGCACATGCCTGTAATC
CCAGCTACTTGGGAGGCTGAAGTAGGAGAATTGCTTGAACCCATGAGGAGGAGATTGCAGTGAGA
TTTTGCCATTGCATTCTAGCCTGGGCAACAAGAACTCCATCTTAAAAAAAATTTTAAAAACCATC
ACACAAACAGAAAGCATGTCCTTTAATTTTACCTATCCTTCAAACTTAAGCAAAAATTTTCCTTTTA
TAACCAAAAAAAACCTTTAGACACTTTTACATATGGGAGGTCAGGCACAGTGGCTCATGCCTGTA
ATCCCAGCAGGAAGATCGCGAAAAGCATTTTTCAAATGCACAAATGCTTAAAGATTCAGGAGTAA
GTGGGCTATTACACCTGTTAAGCCTATTACCATGTAGTTTCATTCCTAGTGACCAAGTAGACAAAC
TGCTAATTATCAAAGCATAAAAGGTATTAGACTCTGCAGGAGAAAAGCAATGTAGATTAGTCTAA
TTTTATAGCTACTTCAAATTGCCATCTTTTTCTATTAGAACCTTGTTCCTATTCTGAATAGCACTCAA
TAGAACTTGTGAAACCATCAAACTGGCATAAAGCTTACTCCACTGACTTCAAAATGGACCCTTCCA
CTCATAGGGTGTACACTAGCCACTACACTTATTTCTTATGTCATGGCAAATAGTCAACTTTCACTGC
CCAGTCATTTTAACCCACGTTTCAACATGCACATCCCAGTAATTTGGAAACATTTTGTTTCCAAAGA
TTCACTTAACATTGGTTTAGCAACATGAAGCTTTCTATGCAACACAAGGACTCAGTTTTTGGCCTGT
TTTAGTGACAGGCAATCAGCAACATGCTGCATTTCTCTCCAGTGTTGTAATCAAAGCAACCCTCCC
ATAGCTTTAAATGATATTCCTTCCCCTTCCAATTATGTGGGGGAAAACAACCCTATTCTCCACCCA
GAAGTGTTAACTCAAGAATTACATTTTCAAGAAGTTTCCAGATTCGTAAAACCAGAATTAGATGTC
TTTCACCTAAATGTCTCGGTGTTGACCAAAGGAACACACAGGTTTCTCATTTAACTTTTTTAATGGG
TCTCAAAATTCTGTGACAAATTTTTGGTCAAGTTGTTTCCATTAAAAAGTACTGATTTTAAAAACTA
ATAACTTAAAACTGCCACACGCAAAAAAGAAAACCAAAGTGGTCCACAAAACATTCTCCTTTCCTT
CTGAAGGTTTTACGATGCATTGTTATCATTAACCAGTCTTTTACTACTAAACTTAAATGGCCAATTG
AAACAAACAGTTCTGAGACCGTTCTTCCACCACTGATTAAGAGTGGGGTGGCAGGTATTAGGGAT
AATATTCATTTAGCCTTCTGAGCTTTCTGGGCAGACTTGGTGACCTTGCCAGCTCCAGCAGCCTTCT
TGTCCACTGCTTTGATGACACCCACCGCAACTGTCTGTCTCATATCACGAACAGCAAAGCGACCTA
TTAAAAAAAAGTTAATTATTACCCAAAGTACTGTTCAGTTGTATTTTTCATCTTTAACACAACTTT
TTTACATTTAAGTAGTCATCCTTACCCAAAGGTGGATAGTCTGAGAAGCTCTCAACACACATGGGC
TTGCCAGGAACCATATCAACAATGGCAGCATCACCAGACTTCAAGAATTTAGGGCCATCTTCCAGC
TTTTTACCAGAACGGCGATCAATCTTTTCCTTCAGCTCAGCAAACTTGCATGCAATGTGAGCCGTGT
GGCAATCCAATACAGGGGCATAGCCGGCGCTTATTTGGCCTGGATGGTTCAGGATAATCACCTTGG
AAAAAAGATTTGCGTTCAGTGCAAATCCAAAGTCTCAAATGACTTTAGCCTCTGCAGTAAGTTAAT
GTTACTTTAAATTGTTACCTGAGCAGTGAAGCCAGCTGCTTCCATTGGTGGGTCATTTTTGCTGTCA
CCAGCAACGTTGCCACGACGAACATCCTTGACAGACACATTCTTGACATTGAAGCCCACATTGTCC
CCAGGAAGAGCTTCACTCAAAGCTTCATGGTGCATTTCGACAGATTTTACTTCCGTTGTAACGTTG
ACTGGAGCAAAGGTGACCACCATACCGGGTTTGAGAACACCAGTCTCCACTCGGCCAACAGGAAC
AGTACCAATACCTAAAAATATTTACAGCATACTAAATACCTATGAAGGCAGACAGTACTCTATCAA
```

```
CTCAAATTCAACTTTGTTTACAGCCAACTTACCACCAATTTTGTAGACATCCTGGAGAGGCAGGCG

CAAGGGCTTGTCAGTTGGACGAGTTGGTGGTAGGATGCAGTCCAGAGCCTCAAGCAGCGTGGTTC

CACTGGCATTGCCATCCTTACGGGTGACTTTCCATCCCTTGAACCAAGGCATCTGAAACACAAGCA

TGCCAATTTGTGTAAGCATGAAATCGCCATTCCCAGAGCTTTTTAACAATGGTCTTGAAAGCCACT

TACGTTAGCACTTGGCTCCAGCATGTTGTCACCATTCCAACCAGAAATTGGCACAAATGCTACTGT

GTCGGGGTTGTAGCCAATTTTCTTAATGTAAGTGCTGACTTCCTTAACAATTTCCTCATATCTCTTC

TGGCTGTAGGGTGGCTCAGTGGAATCCATTTTGTTAACACCGACAATTAGTTGTTTCACACCCAGT

GTGTAAGCCAGAAGGGCATGCTCTCGGGTCTGCCCATTCTTGGAGATACCAGCTTCAAATTCACCA

ACACCAGCAGCAACAATCAGGACAGCACAGTCAGCCTTTAAAGAAAGCAAAGACATATCCCTGTC

AACTCTCCAAATGACAAAACCAGTGTACAAAGCAAGCCTTTTGGGATAAAGAAACCTAGAATTAT

TAATCCCACCAACCTGAGATGTCCCTGTAATCATGTTTTTGATAAAGTCTCTGTGTCCTGGGGCATC

AATGATAGTCACATAGTACTTGCTGGTCTCAAATTTCCACAAGGAGATATCAATGGTGATACCACG

TTCACGCTCAGCTTTCAGTTTATCCAAGACCCAGGCATACTTGAAGGAGCCCTTTCCCATCTGTAA

GGATTAAGAGTCTTTACTTGGTTACTAAAACACAAACTCCAGCTTCAATTTCCTTGTCCCCAGCCCT

TAATTGGCAGTTTCCACTTTACAACTCCAAGTCCAAAGTGATTTTAGTCACTTTGGGTTACAGAAG

CAACCAAAAATCAAACTTTTATAAGTAGGATCTTAACTATTAACATCCAAATCTACTCACTAGCAA

TACGATTACAGAAGTCACCAAAAGCAAATTATTTCATAAGTAAGGTCTTAACTATTAGCATTCAG

ATCTAAACCACTCACTAGTTCTGGGGAAATCACCTAATGATTCTGCTGGTAAAACTCATTTTAGTT

GATCTTTCCCTTTCTGGTATTAAACATACCTCAGCAGCCTCCTTCTCAAATTTTTCAATGGTTCTTTT

GTCGATGCCACCGCATTTATAGATCAGATGGCCAGTAGTGGTGGACTTGCCCGAATCTACGTGTCC

AATGACGACAATGTTGATATGAGTCTTTTCCTTTCCCATTTTGGCTTTTAGGGGTAGTTTTCACGAC

ACCTGAAATGGAAGAAAAAAACTTTGAACCACTGTCTGAGGCTTGAGAATGAACCAAGATCCAAA

CTCAAAAAGGGCAAATTCCAAGGAGAATTACATCAAGTGCCAAGCTGGCCTAACTTCAGTCTCCA

CCCACTCAGTGTGGGAAACTCCATCGCATAAAACCCCTCCCCCCAACCTAAAGACGACGTACTCC

AAAAGCTCGAGAACTAATCGAGGTGCCTGGACGGCGCCCGGTACTCCGTGGAGTCACATGAAGCG

ACGGCTGAGGACGGAAAGGCCCTTTTCCTTTGTGTGGGTGACTCACCCGCCCGCTCTCCCGAGCGC

CGCGTCCTCCATTTTGAGCTCCCTGCAGCAGGGCCGGGAAGCGGCCATCTTTCCGCTCACGCAACT

GGTGCCGACCGGGCCAGCCTTGCCGCCCAGGGCGGGGCGATACACGGCGGCGCGAGGCCAGGCA

CCAGAGCAGGCCGGCCAGCTTGAGACTACCCCCGTCCGATTCTCGGTGGCCGCGCTCGCAGGCCCC

GCCTCGCCGAACATGTGCGCTGGGACGCACGGGCCCCGTCGCCGCCCGCGGCCCCAAAAACCGAA

ATACCAGTGTGCAGATCTTGGCCCGCATTTACAAGACTATCTTGCCAGAAAAAAAGCGTCGCAGC

AGGTCATCAAAAATTTTAAATGGCTAGAGACTTATCGAAAGCAGCGAGACAGGCGCGAAGGTGCC

ACCAGATTCGCACGCGGCGGCCCCAGCGCCCAGGCCAGGCCTCAACTCAAGCACGAGGCGAAGGG

GCTCCTTAAGCGCAAGGCCTCGAACTCTCCCACCCACTTCCAACCCGAAGCTCGGGATCAAGAATC

ACGTACTGCAGCCAGGGGCGTGGAAGTAATTCAAGGCACGCAAGGGCCATAACCCGTAAAGAGG

CCAGGCCCGCGGGAACCACACACGGCACTTACCTGTGTTCTGGCGGCAAACCCGTTGCGAAAAAG
``` the EFS sequence (i.e. the EF1 a sequence used in the vector.

SEQ ID NO: 4

```
GGCTCCGGTGCCCGTCAGTGGGCAGAGCGCACATCGCCCACAGTCCCCGAGAAGTTGGGGGGAGG

GGTCGGCAATTGAACCGGTGCCTAGAGAAGGTGGCGCGGGGTAAACTGGGAAAGTGATGTCGTGT

ACTGGCTCCGCCTTTTTCCCGAGGGTGGGGGAGAACCGTATATAAGTGCAGTAGTCGCCGTGAACG

TTCTTTTTCGCAACGGGTTTGCCGCCAGAACACAGGTGTCGTGACGC
``` the sequence of the sense qPCR primer for the HIV psi region
specific for the packaging region of LVs.
                                                     SEQ ID NO: 5
ACCTGAAAGCGAAAGGGAAAC the sequence of the antisense qPCR primer for the HIV psi region
specific for the packaging region of LVs.
                                                     SEQ ID NO: 6
CGCACCCATCTCTCTCCTTCT the sequence of the qPCR probe for the HIV psi region.
                                                     SEQ ID NO: 7
FAM-AGCTCTCTCGACGCAGGACTCGGC-TAMRA the sequence of the sense qPCR primer for GFP.
                                                     SEQ ID NO: 8
CTGCTGCCCGACAACCA the sequence of the antisense qPCR primer for GFP.
                                                     SEQ ID NO: 9
GAACTCCAGCAGGACCATGTG the sequence of the qPCR probe for GFP.
                                                     SEQ ID NO: 10
FAM-CCCTGAGCAAAGACCCCAACGAGA-TAMRA the sequence of the sense qPCR primer for the human ADA gene.
                                                     SEQ ID NO: 11
GGTCCATCCTGTGCTGCAT the sequence of the antisense qPCR primer for human ADA
gene.
                                                     SEQ ID NO: 12
CGGTCTGCTGCTGGTACTTCTT the sequence of the qPCR probe for the human ADA gene.
                                                     SEQ ID NO: 13
FAM-CCAGCCCAACTGGTCCCCCAAG-TAMRA the sequence of the sense qPCR primer for SDC4.
                                                     SEQ ID NO: 14
CAGGGTCTGGGAGCCAAGT the sequence of the antisense qPCR primer for SDC4.
                                                     SEQ ID NO: 15
GCACAGTGCTGGACATTGACA the sequence of the qPCR probe for SDC4.
                                                     SEQ ID NO: 16
HEX-CCCACCGAACCCAAGAAACTAGAGGAGAAT-IOWA BLACK FQ

---

The invention claimed is:

1. A method of treating adenosine deaminase severe combined immunodeficiency (ADA-SCID) in a human patient in need thereof, comprising administering a therapeutically effective amount of a composition comprising a host human hematopoietic stem cell (HSC) or a cell population of human HSCs to the blood and/or bone marrow of said patient, wherein said host cell or cell population contains a vector or expression cassette comprising a transgene encoding a human adenosine deaminase (hADA) operably linked to a regulator region comprising an elongation factor 1-alpha short isoform (EFS) promoter; wherein said transgene is expressed in peripheral blood mononuclear cells (PBMCs) of said patient and wherein the transgene expression is elevated for at least 6 months after administration of the composition and is elevated relative to expression of a transgene encoding said hADA operably linked to a MND promoter when normalized per vector copy number.

2. The method of claim 1, wherein:
(a) the vector or expression cassette is present at a copy number of 1, 2, 3, 4, 5, 6, 7, 8, 9 or 10 copies per single cell; or
(b) the vector or expression cassette is present at a median copy number of from 0.5 to 6 in said cell population.

3. The method of claim 1, wherein said vector is a self-inactivating lentiviral vector comprising said transgene operably linked to said EFS promoter, wherein said vector further comprises a woodchuck hepatitis post-transcriptional regulatory element (wPRE) element.

4. The method of claim 1, wherein the transgenes are codon-optimized for expression in a human cell.

5. The method of claim 1, wherein the vector is a self-inactivating human immunodeficiency virus 1 (HIV-1) lentiviral vector.

6. The method of claim 1, wherein the transgene encoding the hADA operably linked to the regulatory region comprising the EFS promoter has a sequence of SEQ ID NO: 1 or a variant thereof having at least 95% sequence identity to SEQ ID NO: 1.

7. The method of claim 1, wherein the cell population further comprises peripheral blood stem cells (PBSCs).

8. The method of claim 1, wherein said host cell or cell population is isolated prior to pre-stimulation in medium supplemented with Flt3L, IL-3, TPO and SCF.

9. The method of claim 1, wherein expression of hADA and/or metabolic activity of hADA is corrected to levels present in a human that does not have ADA-SCID or levels above those found in a human that does not have ADA-SCID.

10. The method of claim 3, wherein expression of hADA and/or activity of hADA is higher than expression of hADA and/or activity of hADA in a patient with ADA-SCID that received the transgene encoding hADA operably linked to the regulatory region comprising the EFS promoter delivered by a gamma retroviral vector present at the same average copy number as the lentiviral vector.

11. The method of claim 9, wherein the expression of hADA and/or activity of hADA is corrected in the PMBC and/or red blood cells.

12. The method of claim 1, wherein at least one immunological defect associated with ADA-SCID is corrected in said patient.

13. The method of claim 12, wherein the CD3 count, CD4 count, CD8 count, naïve T cell count, T-cell receptor excision circles (TREC) levels and/or immunoglobulin levels are corrected.

14. The method of claim 1, wherein expression of the transgene encoding the hADA operably linked to the EFS promoter is sustained for at least 12, 24, or 48 months post-administration of the composition.

15. The method of claim 1, wherein the host cell or cell population is derived from the same patient, an individual who is related to the patient, or an individual who is a tissue type match for the patient.

16. The method of claim 1, wherein the host cell or cell population is derived from an individual with a different genetic background from the patient to which it is administered.

17. The method of claim 1, wherein: (a) the vector or expression cassette comprises a lentivirus genome; and (b) the transgene encoding hADA operably linked to the EFS promoter is flanked by a long terminal repeat (LTR) and a central polypurine tract (cPPT) at the 5' end and a wPRE sequence and a LTR lacking a U3 region at the 3' end.

18. The method of claim 1, wherein the composition further comprises a pharmaceutically acceptable excipient.

19. The method of claim 5, where the host cell or cell population is made by a method comprising introducing into said host cell or cell population a self-inactivating HIV-1 vector, wherein said vector encodes hADA under the control of an EFS promoter, and wherein the vector comprises a wPRE element.

20. The method of claim 19, wherein the HIV-1 vector comprises the sequence of SEQ ID NO: 2 or a variant thereof having at least 85% identity to SEQ ID NO: 2.

21. The method of claim 19, comprising isolating the cell or cell population from a human.

22. The method of claim 21, further comprising culturing the isolated cell or cell population.

23. The method of claim 22, wherein the isolated cell or cell population is derived from the same patient, an individual who is related to the patient, an individual who is a tissue type match for the patient, or an individual with a different genetic background from the patient to which the composition is administered.

* * * * *

SEQUENCE LISTING

<160> NUMBER OF SEQ ID NOS: 16

<210> SEQ ID NO 1
<211> LENGTH: 1081
<212> TYPE: DNA
<213> ORGANISM: Artificial Sequence
<220> FEATURE:
<223> OTHER INFORMATION: HUMAN CODON OPTIMISED ADA CDNA SEQUENCE

<400> SEQUENCE: 1
atggcccaga cccccgcctt cgacaagccc aaggtggagc tgcacgtgca cctggacggc     60
agcatcaagc tgagaccat cctctactac ggcaggcgga gaggcatcgc cctgcccgcc    120
aacacagcga gggcctgctg aacgtgatcg gcatggacaa gccctgacc ctgcccgact    180 tcctggccaa gttcgactac tacatgcccg ccatcgccgg ctgccgggag gccatcaagc    240
ggatcgccta cgagtcgtgg agatgaaggc caaggaaggc gtggtgtacg tggaagtgcg    300
gtacagcccc cacctgctgg ccaacagcaa ggtggaaccc atccccctgga accaggccga    360

```
gggcgacctg accccgacg agtggtggct ctggtcggcc aggggctgca ggaaggcgag      420
cgggacttcg gcgtgaaggc ccggtccatc ctgtgctgca tgcggcacca gcccaactgg      480
tcccccaagg tggtggagct gtgcaagagt accagcagca gaccgtggtg gccatcgacc      540
tggccggcga tgagaccatc cccggctcca gcctgctccc cggccacgtg caggcctacc      600
aggaagccgt caagagcggc atccaccgga ccgtgacgcc ggcgaagtgg gcagcgccga      660
ggtggtgaaa gaagccgtgg acatcctgaa aaccgagcgg ctgggccacg gctaccacac      720
cctggaagat caggccctgt acaaccggct gcggcaagaa aaatgcactt cgagatctgc      780
ccctggtcca gctacctgac cggcgcctgg aagcccgaca ccgagcacgc cgtgatccgg      840
ctgaagaacg accaggccaa ctacagcctg aacaccgacg acccctgac ttcaagagca      900 ccctggacac cgactaccag atgaccaagc gggacatggg cttcaccgag aagagttca      960 agcggctgaa catcaacgcc gccaagagca gcttcctgcc cgaggacgag aagcggagct     1020
gctggacctg ctgtacaagg cctacggcat gcccctagc gccagcgccg acagaacct     1080 g                                                                   1081

<210> SEQ ID NO 2
<211> LENGTH: 7847
<212> TYPE: DNA
<213> ORGANISM: Artificial Sequence
<220> FEATURE:
<223> OTHER INFORMATION: LV EFS ADA LENTIVIRAL VECTOR FROM THE JUNCTION
      MARKER

<400> SEQUENCE: 2
acgcgccctg tagcggcgca ttaagcgcgg cgggtgtggt ggttacgcgc agcgtgaccg       60
ctacacttgc cagcgcccta gcgcccgctc ctttcgcttt cttcccttcc tttctcgcca      120
cgttcgcggc tttccccgtc aagctctaaa tcggggctc cctttagggt tccgatttag      180
tgctttacgg cacctcgacc ccaaaaaact tgattagggt gatggttcac gtagtgggcc      240
atcgccctga tagaggtttt tcgcccttttg acgttggagt ccacgttctt taatagtgga      300
ctcttgttcc aaactggaac aacactcaac cctatctcgg tctattcttt tgatttataa      360
gggattttgc cgatttcggc cattggttaa aaaatgagct gatttaacaa aaatttaacg      420
cgaattttaa caaatatta acgcttacaa ttaggtggc acttttcggg gaaatgtgcg      480
cggaacccct atttgtttat ttttctaata cattcaaata tgtatccgct catgagacaa      540
taaccctgat aaatgcttca ataatagcac ctagatcaag agacaggatg aggatcgttt      600
cgcatgattg aacaagatgg attgcacgca ggttccggc gcttgggtg gagaggctat      660 tcggctatga ctgggcacaa cagacaatcg gctgctctga tgccgccgtg ttccggctgt      720
cagcgcaggg gcgcccggtt ctttttgtca gaccgacct gtcggtgccc tgaatgaact      780
gcaagacgag gcagcgcggc tatcgtggct ggccacgacg ggcgttcctt gcgcagctgt      840
gctcgacgtt gtcactgaag cgggaaggga ctggctgcta ttgggcgaat gccggggcag      900
gatctcctgt catctcacct tgctcctgcc gagaaagtat ccatcatggc tgatgcaatg      960
cggcggctgc atacgcttga tccggctacc tgcccattcg accaccaagc gaaacacgca     1020
tcgagcgagc acgtactcgg atggaagccg gtcttgtcga tcaggatgat ctggacgaag     1080
agcatcaggg gctcgcgcca gccgaactgt tcgccaggct caaggcgagc atgcccgacg     1140
gcgggatctc gtcgtgaccc atggcgatgc ctgcttgccg aatatcatgg tggaaaatgg     1200
ccgcttttct ggattcatcg actgtggccg gctgggtgtg gcggaccgct atcaggacat     1260
```

```
agcgttggct cccgtgatat tgctgaagag cttggcggcg aatgggctga ccgcttcctc    1320
gtgctttacg gtatcgccgc tcccgattcg cagcgcatcg ccttctatcg ccttcttgac    1380
gagttcttct gaattataac gcttacaatt tcctgatgcg gtattttctc cttacgcatc    1440
tgtgcggtat ttcacaccgc atcaggtggc acttttcggg gaaatgtgcg cggaacccct    1500
atttgtttat ttttctaaat acatcaaata tgtatccgct catgaccaaa atcccttaac    1560
gtgagttttc gttccactga gcgtcagacc ccgtagaaaa gatcaaagga tcttcttgag    1620
atcctttttt tctgcgcgta atctgctgct tcaaacaaaa aaaccaccgc taccagcggt    1680
ggtttgtttg ccggatcaag agctaccaac tctttttccg aaggtaactg gcttcagcag    1740
agcgcagata ccaaatactg ttcttctagt gtagccgtgt taggccacca cttcaagaac    1800
tctgtagcac cgcctacata cctcgctctg ctaatcctgt taccagtggc tgctgccagt    1860
ggcgataagt cgtgtcttac cgggttggac tcaagacgat agttaccgga taaggcgcagc   1920
ggtcgggctg aacggggggg tcgtgcacac agcccagctt ggagcgaacg acctacaccg    1980
aactgagata cctacagcgt gagctatgag aaagcgccac gcttcccgaa ggagaaaggc    2040
ggacaggtat ccggtaagcg gcagggtcgg aacaggagag cgcacgaggg agcttccagg    2100
gggaaacgcc tggtatcttt atagtcctgt cgggtttcgc cacctctgac ttgagcgtca    2160
ttttgtgat gctcgtcagg ggggcggagc ctatggaaaa acgccagcaa cgcggccttt     2220
ttacggttcc tggccttttg ctggcctttt gctcacatgt tctttcctgc gttatcccct    2280
gattctgtgg ataaccgtat taccgccttt gagtgagctg ataccgctcc cgcagccgaa    2340
cgaccgagcg cagcgagtca gtgagcgagg aagcggaaga gcgcccaata cgcaaaccgc    2400
ctctccccgc gcgttggccg attcattaat gcagctggca cgacaggttt cccgacggaa    2460
agcgggcagt gagcgcaacg caattaatgt gagttagctc actcattagg caccccaggc    2520
tttacacttt atgcttccgg ctcgtatgtt gtgtggaatt gtgagcggat aacaatttca    2580
cacggaaaca gctatgacca tgattacgcc aagcgcgcaa ttaaccctca ctaaagggaa    2640
caaaagctgg agctgcaagc ttggccattg catacgttgt atccatatca taatatgtac    2700
atttatattg ctcatgtcca acattaccgc catgttgaca ttgattattg actagttatt    2760
aatagtaatc aattacgggg tcattagttc atagcccata tatggagttc cgcgttacat    2820
aacttacggt aaatggccgc ctggctgacc gcccaacgac ccccgcccat tgacgtcaat    2880
aatgacgtat gttcccatag taacgccaat agggactttc cattgacgtc aatgggtgga    2940
gtatttacgg taaactgccc acttgcagta catcaagtgt atcatatgcc aagtacgccc    3000
cctattgacg tcaatgacgg taaatggccc gcctggcatt atgcccagta catgacctta    3060
tgggactttc ctacttggca gtacatctac gattagtcat cgctattacc atggtgatgc    3120
ggttttggca gtacatcaat gggcgtggat agcggtttga ctcacgggga tttccaagtc    3180
tccaccccat tgacgtcaat gggagtttgt tttggcacaa atcaacggga ctttccaaa     3240
atgtcgtaac aactccgccc cattgacgca atgggcggt aggcgtgtac ggtgggaggt     3300
ctatataagc agagctcgtt tagtgaaccg gggtctctct ggttaaccag atctgagcct    3360
gggagctctc tggctaacta gggaacccac tgcttaagcc tcaataaagc ttgccttgag    3420
tgcttcaagt agtgtgtgcc cgtctgttgt gtgactctgg taactagaga tcctcagacc    3480
ctttttagtca gtgtggaaaa tctctagcag tggcgcccga acagggactt gaaagcgaaa    3540
gggaaaccag aggagctctc tcgacgcagg actcggcttg ctgaagcgcg cacggcaagg    3600
gcgaggggcg gcgactggtg agtacgccaa aaattttgac tagcggaggc tagaaggaga   3660
```

```
gagatgggtg cgagagcgtc agtattaagc gggggagaat tagatcgcga tgggaaaaaa    3720
ttcggtaagg ccaggggaa agaaaaaata taaattaaaa catatagtat gggcaagcag    3780
ggagctagaa cgattcgcag ttaatcctgg cctgttagaa acatcagaag gctgtagaca    3840
aatactggga cagtacaacc atcccttcag acaggatcag aagaacttag atcattatat    3900
aatacagtag caaccctcta ttgtgtgcat caaaggatag agataaaaga caccaaggaa    3960
gctttagaca agatagagga gagcaaaaca aaagtaagac caccgcacag caagcggccg    4020
ctgatcttca gacctggagg aggagatatg agggacaatt ggagaagtga attatataaa    4080
tataaagtag taaaaattga accattagag tagcacccac caaggcaaag agaagagtgg    4140
tgcagagaga aaaaagagca gtgggaatag gagctttgtt ccttgggttc ttgggagcag    4200
caggaagcac tatgggcgca gcgtcaatga cgctacggta caggccagac aattattgtc    4260
tggtatagtg cagcagcaga acaatttgct gagggctatt gaggcgcaac agcatctgtt    4320
gcaactcaca gtctgggca tcaagcagct ccaggcaaga acctggctgt ggaaagatac    4380
ctaaaggatc aacagctcct ggggatttgg ggttgctctg gaaaactcat ttgcaccact    4440
gctgtgcctt ggaatgctag ttggagtaat aaatctctgg aacagattgg aatcacacga    4500
cctggatgga gtgggacaga gaaattaaca attacacaag cttaatacac tccttaattg    4560
aagaatcgca aaaccagcaa gaaaagaatg aacaagaatt attggaatta gataatgggc    4620
aagtttgtgg aattggttta acataacaaa ttggctgtgg tatataaaat tattcataat    4680
gatagtagga ggcttggtag gtttaagaat agttttgct gtactttcta tagtgaatag    4740
agttaggcag ggatattcac cattatcgtt tcagacccac ctcccaaccc cgaggggacc    4800
cgacaggccc gaaggaatag aagaagaagg ggagagagag acagagacag atccattcga    4860
ttagtgaacg gatctcgacg gtatcggtta acttttaaaa gaaaaggggg gattgggggg    4920
tacagtgcag gggaaagaat agtagacata atagcaaaga catacaaact aaagaattac    4980
aaaaacaaat tacaaaattc aaaattttat cgattggctc cggtgcccgt cagtgggcag    5040
agcgcacatc gcccacagtc cccgagaagt tgggggagg ggtcgcaatt gaaccggtgc    5100
ctagagaagg tggcgcgggg taaactggga aagtgatgtc gtgtactggc tccgcctttt    5160
tcccgagggt gggggagaac cgtatataag tgcagtagtc gccgtgaacg tcttttttcgc    5220 aacgggtttg ccgccagaac acaggtgtcg tgacgcggga tccagcgctg cggccgcgcc    5280
accatggccc agacccccgc cttcgacaag cccaaggtgg agctgcacgt gcacctggcg    5340
gcagcatcaa gcctgagacc atcctctact acggcaggcg gagaggcatc gccctgcccg    5400
ccaacacagc cgagggcctg ctgaacgtga tcggcatgga caagcccctg accctgcccg    5460
acttctggcc aagttcgact actacatgcc cgccatcgcc ggctgccggg aggccatcaa    5520
gcggatcgcc tacgagttcg tggagatgaa ggccaaggaa ggcgtggtgt acgtggaagt    5580
gcggtacagc cccacctgct ggccaacagc aaggtggaac ccatcccctg gaaccaggcc    5640
gagggcgacc tgaccccgga cgaggtggtg gctctggtcg gccaggggct gcaggaaggc    5700
gagcgggact cggcgtgag gcccggtcca tcctgtgctg catgcggcac cagcccaact    5760
ggtcccccaa ggtggtggag ctgtgcaaga agtaccagca gcagaccgtg gtggccatcg    5820
acctggccgg cgatgagacc atccccgctc cagcctgctc cccggccacg tgcaggccta    5880
ccaggaagcc gtcaagagcg gcatccaccg gaccgtgcac gccggcgaag tgggcagcgc    5940
cgaggtggtg aaagaagccg tggacatcct gaaaccgagc ggctgggcca cggctaccac    6000
```

```
acctggaag atcaggccct gtacaaccgg ctgcggcaag aaaacatgca cttcgagatc      6060
tgccctggt ccagctacct gaccggcgcc tggaagcccg caccgagcac gccgtgatcc      6120
ggctgaagaa cgaccaggcc aactacagcc tgaacaccga cgacccctg atcttcaaga     6180
gcaccctgga caccgactac cagatgacca gcgggacat gggcttcccg aggaagagtt     6240
caagcggctg aacatcaacg ccgccaagag cagcttcctg cccgaggacg agaagcggga    6300
gctgctggac ctgctgtaca aggcctacgg catgccccct agcgccagcg ccggcagaac    6360
ctgtgatgag tcgacaatca acctctggat tacaaaattt gtgaaagatt gactggtatt    6420
cttaactatg ttgctccttt tacgctatgt ggatacgctg ctttaatgcc tttgtatcat    6480
gtattgcttc ccgtatggct ttcatttct cctccttgta taaatcctgg ttgctgtctc     6540
tttatgagga gttgtggccc gttgtcaggc aacgtggcgt ggtgtgcact gtgtttgctg    6600
acgcaacccc actggttggg gcattgccac cacctgtcag ctcctttccg ggactttcgc    6660
tttcccccte cctattgcca cggcggaact catcgccgcc tgccttgccc gctgctggac    6720
agggctcgg ctgttggcac tgacaattcc gtggtgttgt cggggaaatc atcgtccttt     6780
ccttggctgc tcgcctgtgt tgccacctgg attctgcgcg gacgtccctt ctgctacgtc    6840
ccttcggccc tcaatccagc ggccttcctt ccgcgcgcct gctgccggct ctgcggcctc    6900
ttccgcgtct tcgccttcgc cctcagacga tcggatctc cctttgggcc gcctccccgc     6960
ctggaattcg agctcggtac cttaagaca atgacttaca aggcagctgt agatcttagc     7020
cacttttaa aagaaaggg gggactggaa gggctaattc actcccaacg aagacaagat      7080
ctgcttttg cttgtactgg gtctctctgg ttagacagat ctgagcctgg gagctctctg     7140
gctaactagg gaacccactg cttaagcctc aataaagctt gccttgagtg cttcaagtag   7200
tgtgtgcccg tctgttgtgt gactctggta actagagatc cctcagaccc ttttagtcag    7260
tgtggaaaat ctctagcagt agtagttcat gtcatctatt attcagtatt tataacttgc    7320
aaagaaatga atatcagaga gtgagaggaa cttgtttatt gcagcttata atggttacaa    7380
ataaagcaat agcatcacaa atttcacaaa taaagcattt ttcactgca ttctagttgt     7440
ggttgtcca aactcatcaa tgtatcttat catgtctggc tctagctatc ccgcccctaa     7500
ctccgcccat cccgcccta actccgccca gttccgccca ttctccgccc atggctgact    7560
aattttttt atttatgcag aggccgaggc cgcctcggcc tctgagctat tccagaagta    7620
gtgaggaggc ttttttggag gcctagggac gtacccaatt cgccctatag tgagtcgatt    7680
acgcgcgctc actggccgtc gttttacaac gtcgtgactg ggaaaaccct ggcgttaccc    7740
aacttaatcg ccttgcagca catcccctt tcgccagctg gcgtaatagc gaagaggccc    7800
gcacgatcgc ccttcccaac agttgcgcag cctgaatggc gaatggg               7847
```

<210> SEQ ID NO 3
<211> LENGTH: 5283
<212> TYPE: DNA
<213> ORGANISM: Artificial Sequence
<220> FEATURE:
<223> OTHER INFORMATION: FULL LENGTH ELONGATION FACTOR 1 ALPHA SEQUENCE

<400> SEQUENCE: 3

```
ttaaagctta aaattcattt attgtagtga gcaagtttgt aatgaatacc agcaggtggt      60
gctcaagcca cagttgtcta agacactggg tttcacagga agttaatctc aatctcagta    120
tatgcaagta aactgactca ttcctgcttc cagtgggaac aattttttcag ttaaatcttg    180
cttccttgca tgtcaagaat tctctactgg taaatcttac aggtgtcaac tttcattatc    240
```

```
agggcatcta ttggccatct attaaaggcc ttacctgttt tttctgtcat ccagcaaatc    300
ttagactatt tacttgtgta aacattagat agcaaagaaa ctaaggacaa aaatctctag    360
ttcaatttag acttgatacc tcagagcact ggctgatggg aaggcatttt atctaattca    420
gactcagatg agggaaaacg ataacacttc attacagact tgtctatggc caattcaagt    480
acctttgaat cttgagcaat acacattgcc agtcacttta agaggcctta tctcttgggc    540
tgctttaact cctgcttagc atgtccttaa gaacacatgt cctggccagg catggtggct    600
catgcctgta attccagcac tttaggaggc cgaggcgatc acctaaggtc aggagtttga    660
gaccagcctg accaacatgg aaaaacctca tctctattaa aaacaccaaa ttagcacatg    720
cctgtaatcc cagctacttg ggaggctgaa gtaggagaat tgcttgaacc catgaggagg    780
agattgcagt gagattttgc cattgcattc tagcctgggc aacaagaact ccatcttaaa    840
aaaaaatttt aaaaaccatc acacaaacag aaagcatgtc ctttaatttt acctatcctt    900
caaacttaag caaaaatttt cctttttataa ccaaaaaaaa acctttagac acttttacat    960
atgggaggtc aggcacagtg gctcatgcct gtaatcccag caggaagatc gcgaaaagca   1020
tttttcaaat gcacaaatgc ttaaagattc aggagtaagt gggctattac acctgttaag   1080
cctattacca tgtagtttca ttcctagtga ccaagtagac aaactgctaa ttatcaaagc   1140
ataaaaggta ttagactctg caggagaaaa gcaatgtaga ttagtctaat tttatagcta   1200
cttcaaattg ccatcttttt ctattagaac cttgttccta ttctgaatag cactcaatag   1260
aacttgtgaa accatcaaac tggcataaag cttactccac tgacttcaaa atggacccTT   1320
ccactcatag ggtgtacact agccactaca cttatttctt atgtcatggc aaatagtcaa   1380
cttTCactgc ccagtcattt taacccacgt ttcaacatgc acatcccagt aatttggaaa   1440
cattttgttt ccaaagattc acttaacatt ggtttagcaa catgaagctt tctatgcaac   1500
acaaggactc agttttTggc ctgttttagt gacaggcaat cagcaacatg ctgcatttct   1560
ctccagtgtt gtaatcaaag caaccctccc atagctttaa atgatattcc ttccccttcc   1620
aattatgtgg ggggaaaaca accctattct ccacccagaa gtgttaactc aagaattaca   1680
ttttcaagaa gtttccagat tcgtaaaacc agaattagat gtctttcacc taaatgtctc   1740
ggtgttgacc aaaggaacac acaggtttct catttaactt ttttaatggg tctcaaaatt   1800
ctgtgacaaa ttttTggtca agttgtttcc attaaaagt actgatttTa aaactaata   1860 acttaaaact gccacacgca aaaagaaaa ccaaagtggt ccacaaaaca ttctcctttc   1920
cttctgaagg ttttacgatg cattgttatc attaaccagt cttttactac taaacttaaa   1980
tggccaattg aaacaaacag ttctgagacc gttcttccac cactgattaa gagtggggtg   2040
gcaggtatta gggataatat tcatttagcc ttctgagctt tctgggcaga cttggtgacc   2100
ttgccagctc cagcagcctt cttgtccact gctttgatga cacccaccgc aactgtctgt   2160
ctcatatcac gaacagcaaa gcgacctatt aaaaaaaaag ttaattatta cccaaagtac   2220
tgttcagttg tattttTcat ctttaacaca actttTttac atttaagtag tcatccttac   2280
ccaaaggtgg atagtctgag aagctctcaa cacacatggg cttgccagga accatatcaa   2340
caatggcagc atcaccagac ttcaagaatt tagggccatc ttccagcttt ttaccagaac   2400
ggcgatcaat cttttccttc agctcagcaa acttgcatgc aatgtgagcc gtgtggcaat   2460
ccaatacagg ggcatagccg gcgcttattt ggcctggatg gttcaggata atcaccttgg   2520
aaaaaagatt tgcgttcagt gcaaatccaa agtctcaaat gactttagcc tctgcagtaa   2580
```

```
gttaatgtta ctttaaattg ttacctgagc agtgaagcca gctgcttcca ttggtgggtc    2640
atttttgctg tcaccagcaa cgttgccacg acgaacatcc ttgacagaca cattcttgac    2700
attgaagccc acattgtccc caggaagagc ttcactcaaa gcttcatggt gcatttcgac    2760
agattttact tccgttgtaa cgttgactgg agcaaaggtg accaccatac cgggtttgag    2820
aacaccagtc tccactcggc aacaggaac agtaccaata cctaaaaata tttacagcat    2880
actaaatacc tatgaaggca gacagtactc tatcaactca aattcaactt tgtttacagc    2940
caacttacca ccaattttgt agacatcctg gagaggcagg cgcaagggct tgtcagttgg    3000
acgagttggt ggtaggatgc agtccagagc ctcaagcagc gtggttccac tggcattgcc    3060
atccttacgg gtgactttcc atcccttgaa ccaaggcatc tgaaacacaa gcatgccaat    3120
ttgtgtaagc atgaaatcgc cattcccaga gcttttaac aatggtcttg aaagccactt    3180
acgttagcac ttggctccag catgttgtca ccattccaac cagaaattgg cacaaatgct    3240
actgtgtcgg ggttgtagcc aattttctta atgtaagtgc tgacttcctt aacaatttcc    3300
tcatatctct tctggctgta gggtggctca gtggaatcca ttttgttaac accgacaatt    3360
agttgtttca cacccagtgt gtaagccaga agggcatgct ctcgggtctg cccattcttg    3420
gagataccag cttcaaattc accaacacca gcagcaacaa tcaggacagc acagtcagcc    3480
tttaaagaaa gcaaagacat atccctgtca actctccaaa tgacaaaacc agtgtacaaa    3540
gcaagccttt tgggataaag aaacctagaa ttattaatcc caccaacctg agatgtccct    3600
gtaatcatgt ttttgataaa gtctctgtgt cctggggcat caatgatagt cacatagtac    3660
ttgctggtct caaatttcca caaggagata tcaatggtga taccacgttc acgctcagct    3720
ttcagtttat ccaagaccca ggcatacttg aaggagccct ttcccatctg taaggattaa    3780
gagtctttac ttggttacta aaacacaaac tccagcttca atttccttgt ccccagccct    3840
taattggcag tttccacttt acaactccaa gtccaaagtg attttagtca ctttgggtta    3900
cagaagcaac caaaaatcaa acttttataa gtaggatctt aactattaac atccaaatct    3960
actcactagc aatacgatta cagaagtcac caaaagcaaa attatttcat aagtaaggtc    4020
ttaactatta gcattcagat ctaaaccact cactagttct ggggaaatca cctaatgatt    4080
ctgctggtaa aactcatttt agttgatctt tccctttctg gtattaaaca tacctcagca    4140
gcctccttct caaattttc aatggttctt ttgtcgatgc caccgcattt atagatcaga    4200
tggccagtag tggtggactt gcccgaatct acgtgtccaa tgacgacaat gttgatatga    4260
gtcttttcct ttcccatttt ggcttttagg ggtagttttc acgacacctg aaatggaaga    4320
aaaaaacttt gaaccactgt ctgaggcttg agaatgaacc aagatccaaa ctcaaaaagg    4380
gcaaattcca aggagaatta catcaagtgc caagctggcc taacttcagt ctccacccac    4440
tcagtgtggg gaaactccat cgcataaaac ccctccccc aacctaaaga cgacgtactc    4500
caaaagctcg agaactaatc gaggtgcctg acggcgccc ggtactccgt ggagtcacat    4560
gaagcgacgg ctgaggacgg aaaggccctt ttcctttgtg tgggtgactc acccgcccgc    4620
tctcccgagc gccgcgtcct ccattttgag ctccctgcag cagggccggg aagcggccat    4680 cttccgctc acgcaactgg tgccgaccgg gccagccttg ccgccagg cggggcgata    4740 cacggcggcg cgaggccagg caccagagca ggccggccag cttgagacta ccccgtccg    4800 attctcggtg gccgcgctcg caggcccgc ctcgccgaac atgtgcgctg ggacgcacgg    4860
gccccgtcgc cgcccgcggc cccaaaaacc gaaataccag tgtgcagatc ttggcccgca    4920
tttacaagac tatcttgcca gaaaaaaagc gtcgcagcag gtcatcaaaa attttaaatg    4980
```

```
gctagagact tatcgaaagc agcgagacag gcgcgaaggt gccaccagat tcgcacgcgg    5040
cggccccagc gcccaggcca ggcctcaact caagcacgag gcgaaggggc tccttaagcg    5100
caaggcctcg aactctccca cccacttcca acccgaagct cgggatcaag aatcacgtac    5160
tgcagccagg ggcgtggaag taattcaagg cacgcaaggg ccataacccg taagagggcc    5220
aggcccgcgg gaaccacaca cggcacttac ctgtgttctg gcggcaaacc cgttgcgaaa    5280
aag                                                                  5283

<210> SEQ ID NO 4
<211> LENGTH: 243
<212> TYPE: DNA
<213> ORGANISM: Artificial Sequence
<220> FEATURE:
<223> OTHER INFORMATION: THE EFS SEQUENCE (I.E. THE EF1A SEQUENCE USED
      IN THE VECTOR

<400> SEQUENCE: 4
ggctccggtg cccgtcagtg ggcagagcgc acatcgccca cagtccccga gaagttgggg    60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtgtcgtga    240
cgc                                                                  243

<210> SEQ ID NO 5
<211> LENGTH: 21
<212> TYPE: DNA
<213> ORGANISM: Artificial Sequence
<220> FEATURE:
<223> OTHER INFORMATION: SENSE QPCR PRIMER FOR THE HIV PSI REGION
      SPECIFIC FOR THE PACKAGING REGION OF LVS

<400> SEQUENCE: 5
acctgaaagc gaaagggaaa c                                              21

<210> SEQ ID NO 6
<211> LENGTH: 21
<212> TYPE: DNA
<213> ORGANISM: Artificial Sequence
<220> FEATURE:
<223> OTHER INFORMATION: ANTISENSE QPCR PRIMER FOR THE HIV PSI REGION
      SPECIFIC FOR THE PACKAGING REGION OF LVS

<400> SEQUENCE: 6
cgcacccatc tctctccttc t                                              21

<210> SEQ ID NO 7
<211> LENGTH: 24
<212> TYPE: DNA
<213> ORGANISM: Artificial Sequence
<220> FEATURE:
<223> OTHER INFORMATION: QPCR PROBE FOR THE HIV PSI REGION
<220> FEATURE:
<221> NAME/KEY: misc_feature
<222> LOCATION: (1)..(1)
<223> OTHER INFORMATION: FAM-
<220> FEATURE:
<221> NAME/KEY: misc_feature
<222> LOCATION: (24)..(24)
<223> OTHER INFORMATION: -TAMRA

<400> SEQUENCE: 7
agctctctcg acgcaggact cggc                                           24
```

<210> SEQ ID NO 8
<211> LENGTH: 17
<212> TYPE: DNA
<213> ORGANISM: Artificial Sequence
<220> FEATURE:
<223> OTHER INFORMATION: SENSE QPCR PRIMER FOR GFP

<400> SEQUENCE: 8
ctgctgcccg acaacca                                                17

<210> SEQ ID NO 9
<211> LENGTH: 21
<212> TYPE: DNA
<213> ORGANISM: Artificial Sequence
<220> FEATURE:
<223> OTHER INFORMATION: ANTISENSE QPCR PRIMER FOR GFP

<400> SEQUENCE: 9
gaactccagc aggaccatgt g                                           21

<210> SEQ ID NO 10
<211> LENGTH: 24
<212> TYPE: DNA
<213> ORGANISM: Artificial Sequence
<220> FEATURE:
<223> OTHER INFORMATION: QPCR PROBE FOR GFP
<220> FEATURE:
<221> NAME/KEY: misc_feature
<222> LOCATION: (1)..(1)
<223> OTHER INFORMATION: FAM-
<220> FEATURE:
<221> NAME/KEY: misc_feature
<222> LOCATION: (24)..(24)
<223> OTHER INFORMATION: -TAMRA

<400> SEQUENCE: 10
ccctgagcaa agaccccaac gaga                                        24

<210> SEQ ID NO 11
<211> LENGTH: 19
<212> TYPE: DNA
<213> ORGANISM: Artificial Sequence
<220> FEATURE:
<223> OTHER INFORMATION: SENSE QPCR PRIMER FOR HUMAN ADA

<400> SEQUENCE: 11
ggtccatcct gtgctgcat                                              19

<210> SEQ ID NO 12
<211> LENGTH: 22
<212> TYPE: DNA
<213> ORGANISM: Artificial Sequence
<220> FEATURE:
<223> OTHER INFORMATION: ANTISENSE QPCR PRIMER FOR HUMAN ADA

<400> SEQUENCE: 12
cggtctgctg ctggtacttc tt                                          22

<210> SEQ ID NO 13
<211> LENGTH: 22
<212> TYPE: DNA
<213> ORGANISM: Artificial Sequence
<220> FEATURE:
<223> OTHER INFORMATION: QPCR PROBE FOR HUMAN ADA
<220> FEATURE:
<221> NAME/KEY: misc_feature
<222> LOCATION: (1)..(1)

```
<223> OTHER INFORMATION: FAM-
<220> FEATURE:
<221> NAME/KEY: misc_feature
<222> LOCATION: (22)..(22)
<223> OTHER INFORMATION: -TAMRA

<400> SEQUENCE: 13
ccagcccaac tggtccccca ag                                              22

<210> SEQ ID NO 14
<211> LENGTH: 19
<212> TYPE: DNA
<213> ORGANISM: Artificial Sequence
<220> FEATURE:
<223> OTHER INFORMATION: SENSE QPCR PRIMER FOR SDC4

<400> SEQUENCE: 14
cagggtctgg gagccaagt                                                  19

<210> SEQ ID NO 15
<211> LENGTH: 21
<212> TYPE: DNA
<213> ORGANISM: Artificial Sequence
<220> FEATURE:
<223> OTHER INFORMATION: ANTISENSE QPCR PRIMER FOR SDC4

<400> SEQUENCE: 15
gcacagtgct ggacattgac a                                               21

<210> SEQ ID NO 16
<211> LENGTH: 30
<212> TYPE: DNA
<213> ORGANISM: Artificial Sequence
<220> FEATURE:
<223> OTHER INFORMATION: QPCR PROBE FOR SDC4
<220> FEATURE:
<221> NAME/KEY: misc_feature
<222> LOCATION: (1)..(1)
<223> OTHER INFORMATION: HEX-
<220> FEATURE:
<221> NAME/KEY: misc_feature
<222> LOCATION: (30)..(30)
<223> OTHER INFORMATION: -IOWA BLACK FQ

<400> SEQUENCE: 16
cccaccgaac ccaagaaact agaggagaat                                      30
```